United States Patent
Ng et al.

(10) Patent No.: US 6,335,441 B1
(45) Date of Patent: Jan. 1, 2002

(54) 5β-CYANO-SUBSTITUTED STEROID COMPOUNDS

(75) Inventors: John S. Ng, Chicago; Chin Liu, Vernon Hills, both of IL (US); Dennis K. Anderson, St. Charles; Jon P. Lawson, Glencoe, both of MO (US); Bernhard Erb, Gipf-Oberfrick (CH); Joseph Wieczorek, Cary, IL (US); Sastry A. Kunda, Chesterfield, MO (US); Leo J. Letendre, Manchester, MO (US); Mark J. Pozzo, Chesterfield, MO (US); Yuen-Lung L. Sing, St. Louis, MO (US); Edward E. Yonan, Carol Stream, IL (US)

(73) Assignee: G.D. Searle & Co., Chicago, IL (US)

( * ) Notice: Subject to any disclaimer, the term of this patent is extended or adjusted under 35 U.S.C. 154(b) by 0 days.

(21) Appl. No.: 09/583,158

(22) Filed: May 30, 2000

Related U.S. Application Data

(62) Division of application No. 09/246,908, filed on Feb. 9, 1999, now Pat. No. 6,180,780, which is a division of application No. 08/763,910, filed on Dec. 11, 1996, now Pat. No. 5,981,744.
(60) Provisional application No. 60/008,455, filed on Dec. 11, 1995.

(51) Int. Cl.$^7$ .............................. C07J 53/00; C07J 71/00

(52) U.S. Cl. ..................... 540/23; 540/15; 552/510

(58) Field of Search ...................... 540/15, 23; 552/510

(56) References Cited

U.S. PATENT DOCUMENTS

| | | | |
|---|---|---|---|
| 3,053,856 A | 9/1962 | Payne et al. | 260/348.5 |
| 3,120,515 A * | 2/1964 | Christiansen | 260/239.5 |
| 3,200,113 A * | 8/1965 | Christiansen et al. | 260/239.5 |
| 3,300,489 A | 1/1967 | Holden | 260/239.57 |
| 3,413,288 A | 11/1968 | Greger | 260/239.57 |
| 3,759,791 A | 9/1973 | Marsheck | 195/51 G |
| 3,897,417 A | 7/1975 | Warnant et al. | 260/239.57 |
| 3,972,878 A | 8/1976 | Schirmann et al. | 260/240 G |
| 4,118,488 A | 10/1978 | Philippson et al. | 424/238 |
| 4,270,994 A | 6/1981 | Behling | 204/78 |
| 4,559,332 A | 12/1985 | Grob et al. | 514/175 |
| 5,565,588 A | 10/1996 | Batist et al. | 552/610 |
| 5,616,742 A | 4/1997 | Fu et al. | 552/595 |

FOREIGN PATENT DOCUMENTS

| | | |
|---|---|---|
| DE | 2404947 | 8/1974 |
| DE | 2443746 | 3/1975 |
| DE | 2349022 | 4/1975 |
| DE | 2932925 | 2/1980 |
| EP | 0122232 A1 | 10/1984 |
| EP | 0123734 A1 | 11/1984 |
| EP | 0165902 A1 | 12/1985 |

OTHER PUBLICATIONS

Christiansen et al., "The reaction of steroidal 4,6–dien–3–ones." Steroids, vol. 1, pp. 620–627, 1963.*

Aria, L. et al., "Epoxidation of Alkenes With Trichloroacetonitrile/Hydrogen Peroxide In A Neutral Biphasic Solvent System", *J. Org. Chem.*, vol. 48, pp. 888–890, 1983.

Carruthers, N. et al., "Synthesis Of Corticoids From 9α–Hydroxyandrost–4–ene–8,17–dione", *J. Org. Chem.*, vol. 57, pp. 961–965, 1992.

DeGasparo, M. et al., "Antialdosterones: Incidence And Prevention Of Sexual Side Effects", *J. Steroid Biochem*, vol. 32, No. 13, pp. 223–227, 1989.

Gabriel, S., "Condensationsproducte aus Phtalsaureanhydrid", *Ber.*, pp. 1389–1396, 1884.

Nagata, W. et al., "Angular–Substituted Polycyclic Compounds. I. Cyanation Of Δ–Cholesten–3–one", *Journal Of Organic Chemistry*, vol. 26, pp. 2413–2420, 1961.

Nagata, W. et al., "Hydrocyanation, VI. Application Of The New Hydrocyanation Methods To Conjugate Hydrocyanation Of a,β–Unsaturated Ketones, Conjugated Dienones, And Conjugated Enamines And To Preparation Of α–Cyanohydrins", *J. Amer. Chem. Soc.*, vol. 94:13, pp. 4654–4672, 1972.

Ogata, Y. et al., "The Alkali Phosphate–Catalyzed Epoxidation And Oxidation By A Mixture Of Nitrile And Hydrogen Peroxide", Tetrahedron, vol. 20, pp. 2065–2068, 1964.

Payne, G. et al., "Reactions of Hydrogen Peroxide. VII. Alkali–Catalyzed Epoxidation and Oxidation Using A Nitrile As Co–reactant", *J. Org. Chem.*, vol. 26, pp. 659–663, 1961.

Turner, A.B. et al., "Applications Of High–potential Quinones. Part I. The Mechanism Of Dehydrogenation Of Steroidal Ketones By 2,3 Dichloro–5,6–dicyanobenzoquinone", *J. Chem. Soc.*, pp. 1720–1730, 1967.

(List continued on next page.)

*Primary Examiner*—Barbara P. Badio
(74) *Attorney, Agent, or Firm*—Scott A. Williams

(57) ABSTRACT

Novel 5β-cyano steroid compounds including compounds of Formula VII:

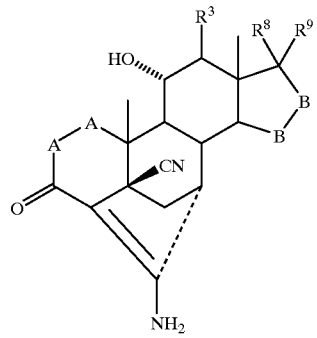

wherein A—A, B—B, $R^3$, $R^8$ and $R^9$ are as defined in the specification.

13 Claims, 5 Drawing Sheets

OTHER PUBLICATIONS de Gasparo, M. et al., "Three New Epoxy–Spirolactone Derivatives: Characterization in Vivo and in Vitro", The Journal Of Pharmacology And Experimental Therapeutics, vol. 240, No. 2, pp. 650–656, 1987.

Ogata, "The Kinetics Of The Phosphate/Catalyzed Epoxidation Of Styrenes With A Mixture Of Nitrile & Hydrogen Peroxide", Bull. Chem. Soc. Of Japan, vol. 38, No. 2, pp. 194–1999, 1965.

Grob J. et al., "Steroidal, Aldosterone Antagonists Increased Selectivity of 9α, 11–Epoxy Derivatives", *Helvetica Chimca Acta*, vol. 80, No. 2, pp. 566–585, Mar. 24, 1997.

Edward A. Brown, et al., "Steroidal Aldosterone Blockers VII", *J. Med. Chem.*, vol. 6, pp. 732–735, 1963.

Edward A. Brown, et al., "Steroidal Aldosterone Blockers III", *J. Org. Chem.*, vol. 25, No. 1, pp. 96–99, 1960.

PCT Search Report Issued for PCT/US96/20780 dated Sep. 22, 1997.

D.H. Peterson et al., "Microbiological Transformations of Steroids. VI. Preparation of 11α–Hydroxy–6–dehydroprogesterone", Journal Of The American Chemical Society, vol. 75, No. 2, pp. 419–421, Jan. 29, 1953.

R. Christiansen et al., "The Reaction Of Steroidal 4,6–dien–3–ones With Cyanide", Steroids, vol. 1, No. 6, pp. 620–627, Jun. 1963.

R.M. Weir et al., "7α–Carboalkoxy Steroidal Spirolactones As Aldosterone Antagonists", Journal of Medicinal Chemistry, vol. 18, No. 8, pp. 817–821, Aug. 1975.

C.M.P. Deshayes, "Utillisation De Modéles Mathématiques Pour l'optimisation En Fermentation. Applicatoins Aux Transformations Par Les Micro–organismes", Bulletine De La Societe Chimque De France 2 Partie—Chimie Organique, Biochimie, No. 1–2, pp. 24–34, May 18, 1979 (translation).

Database WPI, Section Ch, Week 8145, Derwent Publications, Ltd., London, GB; AN 81–82258D and JP 56 120 697 A (Mitsubishi Chem. Ind. Ltd.), Sep. 22, 1981.

Abstract 084228, "Hydroxylated Androstane Production From Sterols", Chemical Abstracts, vol. 100, No. 11, p. 430, Mar. 12, 1984 and JP 58 179 498 A (Danippon Ink and Chemicals, Inc.); Japan, Oct. 20, 1983.

D. Van Leusen et al., "Chemistry of Sulfonylmethyl Isocyanides. 33. Synthesis of 17–(isocyanotosylmethylene) Steroids: Precursors To Pregnane Derivatives" Recueil Des Travaux Chimiques Des Pays–Bas, vol. 110, No. 10, pp. 393–401, Oct. 1991.

L.H. Hellberg et al., "5α–Hydroxy–3α–Cholestanecarboxylic Lactone", *OPPI Briefs*, vol. 15, No. 3, pp. 154–156, 1983.

K. Nickisch et al., "Aldosterone Antagonists.3.Synthesis and Activities of Steroidal 7α–(Alkoxycarbonyl)–15,16–Methylene Spirolactones", *Journal of Medicinal* Chemistry, vol. 33, No. 2, pp. 509–513, Feb. 1990.

* cited by examiner

5β-CYANO-SUBSTITUTED STEROID COMPOUNDS

This application is a divisional application of U.S. application Ser. No. 09/246,908 filed Feb. 9, 1999, now U.S. Pat. No. 6,180,780, which is a divisional application of U.S. application Ser. No. 08/763,910 filed Dec. 11, 1996, now U.S. Pat. No. 5,981,744, which claims priority from U.S. Provisional Application Serial No. 60/008,455 filed Dec. 11, 1995.

BACKGROUND OF THE INVENTION

This invention relates to the novel processes for the preparation of 9,11-epoxy steroid compounds, especially those of the 20-spiroxane series and their analogs, novel intermediates useful in the preparation of steroid compounds, and processes for the preparation of such novel intermediates. Most particularly, the invention is directed to novel and advantageous methods for the preparation of methyl hydrogen 9,11α-epoxy-17α-hydroxy-3-oxopregn-4-ene-7α, 21-dicarboxylate, γ-lactone (eplerenone; epoxymexrenone).

Methods for the preparation of 20-spiroxane series compounds are described in U.S. Pat. No. 4,559,332. The compounds produced in accordance with the process of the '332 patent have an open oxygen containing ring E of the general formula:

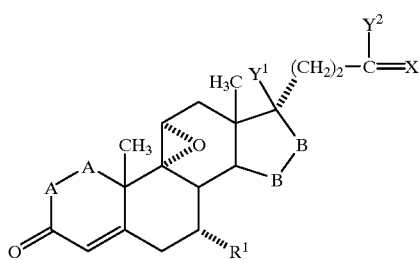

in which
—A—A— represents the group —CH$_2$—CH$_2$— or —CH=CH—,
R$^1$ represents an α-oriented lower alkoxycarbonyl or hydroxycarbonyl radical.
—B—B— represents the group —CH$_2$—CH$_2$— or an α- or β-oriented group

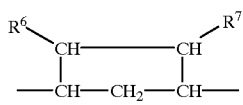

R$^6$ and R$^7$ being hydrogen
X represents two hydrogen atoms or oxo,
Y$^1$ and Y$^2$ together represent the oxygen bridge —O—, or
Y$^1$ represents hydroxy, and
Y$^2$ represents hydroxy, lower alkoxy or, if X represents H$_2$, also lower alkanoyloxy,
and salts of such compounds in which X represents oxo and Y$^2$ represents hydroxy, that is to say of corresponding 17β-hydroxy-21-carboxylic acids.

U.S. Pat. No. 4,559,332 describes a number of methods for the preparation of epoxymexrenone and related compounds of Formula IA. The advent of new and expanded clinical uses for epoxymexrenone create a need for improved processes for the manufacture of this and other related steroids.

SUMMARY OF THE INVENTION

The primary object of the present invention is the provision of improved processes for the preparation of epoxymexrenone, other 20-spiroxanes and other steroids having common structural features. Among the particular objects of the invention are: to provide an improved process that produces products of Formula IA and other related compounds in high yield; the provision of such a process which involves a minimum of isolation steps; and the provision of such a process which may be implemented with reasonable capital expense and operated at reasonable conversion cost.

Accordingly, the present invention is directed to a series of synthesis schemes for epoxymexrenone; intermediates useful in the manufacture of eplerenone; and syntheses for such novel intermediates.

The novel synthesis schemes are described in detail in the Description of Preferred Embodiments. Among the novel intermediates of this invention are those described immediately below.

A compound of Formula IV corresponds to the structure:

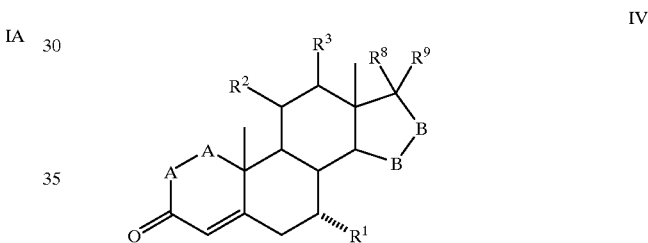

wherein:
—A—A— represents the group —CHR$^4$—CHR$^5$— or —CR$^4$=CR$^5$—
R$^3$, R$^4$ and R$^5$ are independently selected from the group consisting of hydrogen, halo, hydroxy, lower alkyl, lower alkoxy, hydroxyalkyl, alkoxyalkyl, hydroxy carbonyl, cyano, aryloxy,
R$^1$ represents an alpha-oriented lower alkoxycarbonyl or hydroxycarbonyl radical,
R$^2$ is an 11α-leaving group the abstraction of which is effective for generating a double bond between the 9- and 11-carbon atoms;
—B—B— represents the group —CHR$^6$—CHR$^7$— or an alpha- or beta-oriented group:

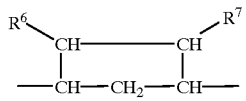

where R$^6$ and R$^7$ are independently selected from the group consisting of hydrogen, halo, lower alkoxy, acyl, hydroxyalkyl, alkoxyalkyl, hydroxycarbonyl, alkyl, alkoxycarbonyl, acyloxyalkyl, cyano, aryloxy, and
R$^8$ and R$^9$ are independently selected from the group consisting of hydrogen, halo, lower alkoxy, acyl, hydroxalkyl, alkoxyalkyl, hydroxycarbonyl, alkyl, alkoxycarbonyl, acyloxyalkyl, cyano, aryloxy, or $R^8$ and $R^9$ together comprise a carbocyclic or heterocyclic ring structure, or $R^8$ or $R^9$ together with $R^6$ or $R^7$ comprise a carbocyclic or heterocyclic ring structure fused to the pentacyclic D ring.

A compound of Formula IVA corresponds to Formula IV wherein $R^8$ and $R^9$ together with the ring carbon to which they are attached form the structure:

XXXIV $$Y^1\diagdown_{C(17)}\diagup^{Y^2}\cdots(CH_2)_2-O\overset{|}{=}X$$

where X, $Y^1$, $Y^2$ and C(17) are as defined above.

A compound of Formula IVB corresponds to Formula IVA wherein $R^8$ and $R^9$ together form the structure of Formula XXXIII:

XXXIII

Compounds of Formulae IVC, IVD and IVE, respectively, correspond to any of Formula IV, IVA, or IVB wherein each of —A—A— and —B—B— is —CH$_2$—CH$_2$—, $R^3$ is hydrogen, and $R^1$ is alkoxycarbonyl, preferably methoxycarbonyl. Compounds within the scope of Formula IV may be prepared by reacting a lower alkylsulfonylating or acylating reagent, or a halide generating agent, with a corresponding compound within the scope of Formula V.

A compound of Formula V corresponds to the structure:

V wherein —A—A—, —B—B—, $R^1$, $R^3$, $R^8$ and $R^9$ are as defined in Formula IV.

A compound of Formula VA corresponds to Formula V wherein $R^8$ and $R^9$ with the ring carbon to which they are attached together form the structure:

XXXIV $$Y^1\diagdown_{C(17)}\diagup^{Y^2}\cdots(CH_2)_2-O\overset{|}{=}X$$

where X, $Y^1$, $Y^2$ and C(17) are as defined above.

A compound of Formula VB corresponds to Formula VA wherein $R^8$ and $R^9$ together form the structure of Formula XXXIII:

XXXIII

Compounds of Formulae VC, VD and VE, respectively, correspond to any of Formula V, VA, or VB wherein each of —A—A— and —B—B— is —CH$_2$—CH$_2$—, $R^3$ is hydrogen, and $R^1$ is alkoxycarbonyl, preferably methoxycarbonyl. Compounds within the scope of Formula V may be prepared by reacting an alkali metal alkoxide with a corresponding compound of Formula VI.

A compound of Formula VI corresponds to the structure:

VI wherein —A—A—, —B—B—, $R^3$, $R_8$ and $R^9$ are as defined in Formula IV.

A compound of Formula VIA corresponds to Formula VI wherein $R^8$ and $R^9$ together with the ring carbon to which they are attached form the structure:

XXXIV $$Y^1\diagdown_{C(17)}\diagup^{Y^2}\cdots(CH_2)_2-O\overset{|}{=}X$$

where X, $Y^1$, $Y^2$ and C(17) are as defined above.

A compound of Formula VIB corresponds to Formula VIA wherein $R^8$ and $R^9$ together form the structure of Formula XXXIII:

XXXIII

Compounds of Formulae VIC, VID and VIE, respectively, correspond to any of Formula VI, VIA, or VIB wherein each of —A—A— and —B—B— is —CH$_2$—CH$_2$—, and $R^3$ is hydrogen. Compounds of Formula VI, VIA, VIB and VIC are prepared by hydrolyzing a compound corresponding to Formula VII, VIIA, VIIB or VIIC, respectively.

A compound of Formula VII corresponds to the structure:

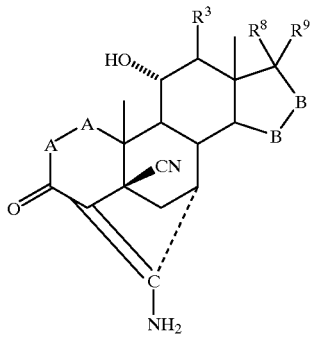

VII wherein —A—A—, —B—B—, $R^3$, $R^8$ and $R^9$ are as defined in Formula IV.

A compound of Formula VIIA corresponds to Formula VII wherein $R^8$ and $R^9$ together with the ring carbon to which they are attached form the structure:

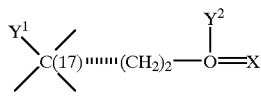

XXXIV where X, $Y^1$, $Y^2$ and C(17) are as defined above.

A compound of Formula VIIB corresponds to Formula VIIA wherein $R^8$ and $R^9$ together form the structure of Formula XXXIII:

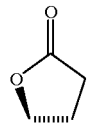

XXXIII

Compounds of Formulae VIIC, VIID and VIIE, respectively, correspond to any of Formula VII, VIIA, or VIIB wherein each of —A—A— and —B—B— is —CH$_2$—CH$_2$—, and $R^3$ is hydrogen. A compound within the scope of Formula VII may be prepared by cyanidation of a compound within the scope of Formula VIII.

A compound of Formula VIII corresponds to the structure:

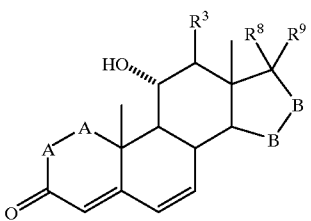

VIII wherein —A—A—, —B—B—, $R^3$, $R^8$ and $R^9$ are as defined in Formula IV.

A compound of Formula VIIIA corresponds to Formula VIII wherein $R^8$ and $R^9$ together with the ring carbon to which they are attached form the structure:

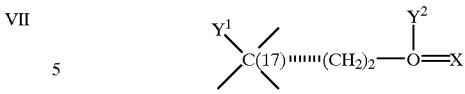

XXXIV where X, $Y^1$, $Y^2$ and C(17) are as defined above.

A compound of Formula VIIIB corresponds to Formula VIIIA wherein $R^8$ and $R^9$ together form the structure of Formula XXXIII:

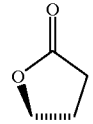

XXXIII

Compounds of Formulae VIIIC, VIIID and VIIIE, respectively, correspond to any of Formula VIII, VIIIA, or VIIIB wherein each of —A—A— and —B—B— is —CH$_2$—CH$_2$—, and $R^3$ is hydrogen. Compounds within the scope of Formula VIII are prepared by oxidizing a substrate comprising a compound of Formula XXX as described hereinbelow by fermentation effective for introducing an 11-hydroxy group into the substrate in α-orientation.

A compound of Formula XIV corresponds to the structure:

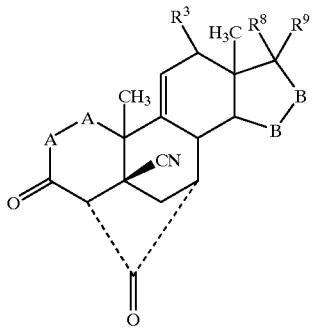

AXIV wherein —A—A—, —B—B—, $R^3$, $R^8$ and $R^9$ are as defined in Formula IV.

A compound of Formula XIVA corresponds to Formula XIV wherein $R^8$ and $R^9$ together with the ring carbon to which they are attached form the structure:

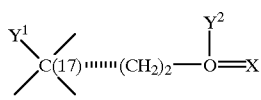

XXXIV where X, $Y^1$, $Y^2$ and C(17) are as defined above.

A compound of Formula XIV corresponds to Formula XIVA wherein $R^8$ and $R^9$ together with the ring carbon to which they are attached form the structure of Formula XXXIII:

XXXIII

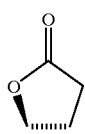

Compounds of Formulae XIVC, XIVD and XIVE, respectively, correspond to any of Formula XIV, XIVA, or XIVB wherein each of —A—A— and —B—B— is —CH$_2$—CH$_2$—, and R$^3$ is hydrogen. Compounds within the scope of Formula XIV can be prepared by hydrolysis of a corresponding compound within the scope of Formula XV.

A compound of Formula XV corresponds to the structure:

AXV

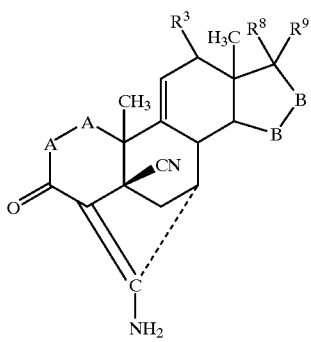

wherein —A—A—, —B—B—, R$^3$, R$^8$ and R$^9$ are as defined in Formula IV.

A compound of Formula XVA corresponds to Formula XV wherein R$^8$ and R$^9$ together with the ring carbon to which they are attached form the structure:

XXXIV

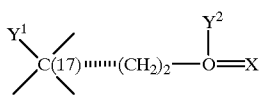

where X, Y$^1$, Y$^2$ and C(17) are as defined above.

A compound of Formula XVB corresponds to Formula XVA wherein R$^8$ and R$^9$ together with the ring carbon to which they are attached form the structure of Formula XXXIII:

XXXIII

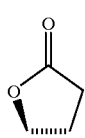

A compound of Formula XVC, XVD and XVE, respectively, correspond to any of Formula XV, XVA, or XVB wherein each of —A—A— and —B—B— is —CH$_2$—CH$_2$—, and R$^3$ is hydrogen. Compounds within the scope of Formula XV can be prepared by cyanidation of a corresponding compound within the scope of Formula XVI.

A compound of Formula XXI corresponds to the structure:

XXI

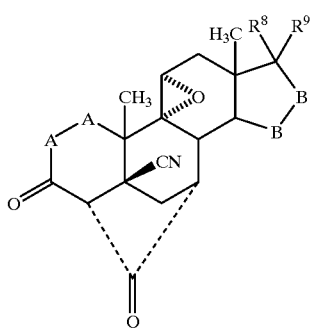

wherein —A—A—, —B—B—, R$^3$, R$^8$ and R$^9$ are as defined in Formula IV.

A compound of Formula XXIA corresponds to Formula XXI wherein R$^8$ and R$^9$ together with the ring carbon to which they are attached form the structure:

XXXIV

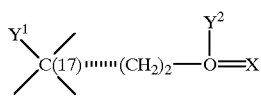

where X, Y$^1$, Y$^2$ and C(17) are as defined above.

A compound of Formula XXIB corresponds to Formula XXIA wherein R$^8$ and R$^9$ together form the structure of Formula XXXIII:

XXXIII

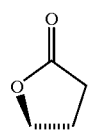

Compounds of Formulae XXIC, XXID and XXIE, respectively, correspond to any of Formula XXI, XXIA, or XXIB wherein each of —A—A— and —B—B— is —CH$_2$—CH$_2$—, and R$^3$ is hydrogen. Compounds within the scope of Formula XXI may be prepared by hydrolyzing a corresponding compound within the scope of Formula XXII.

A compound of Formula XXII corresponds to the structure:

XXII

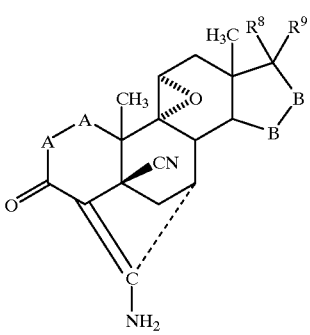

wherein —A—A—, —B—B—, R$^3$, R$^8$ and R$^9$ are as defined in Formula IV.

A compound of Formula XXIIA corresponds to Formula XXII wherein $R^8$ and $R^9$ together with the ring carbon to which they are attached form the structure:

XXXIV

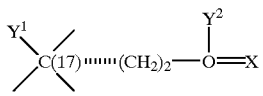

where X, $Y^1$, $Y^2$ and C(17) are as defined above.

A compound of Formula XXIIB corresponds to Formula XXIIA wherein $R^8$ and $R^9$ together form the structure of Formula XXXIII:

XXXIII

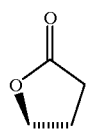

Compounds of Formulae XXIIC, XXIID and XXIIE, respectively, correspond to any of Formula XXII, XXIIA, or XXIIB wherein each of —A—A— and —B—B— is —CH$_2$—CH$_2$—, and $R^3$ is hydrogen. Compounds within the scope of Formula XXII may be prepared by cyanidation of a compound within the scope of Formula XXIII.

A compound of Formula XXIII corresponds to the structure:

XXIII

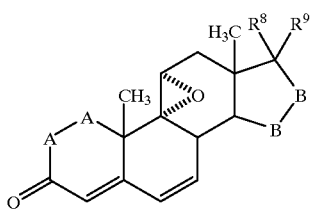

wherein —A—A—, —B—B—, $R^3$, $R^8$ and $R^9$ are as defined in Formula IV.

A compound of Formula XXIIIA corresponds to Formula XXIII wherein $R^8$ and $R^9$ together with the ring carbon to which they are attached form the structure:

XXXIV

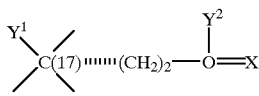

where X, $Y^1$, $Y^2$ and C(17) are as defined above.

A compound of Formula XXIIIB corresponds to Formula XXIIIA wherein $R^8$ and $R^9$ together form the structure of Formula XXXIII:

XXXIII

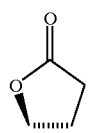

Compounds of Formulae XXIIIC, XXIIID and XXIIIE, respectively, correspond to any of Formula XXIII, XXIIIA, or XXIIIB wherein each of —A—A— and —B—B— is —CH$_2$—CH$_2$—, and $R^3$ is hydrogen. Compounds within the scope of Formula XXIII can be prepared by oxidation of a compound of Formula XXIV, as described hereinbelow.

A compound of Formula 104 corresponds to the structure:

104

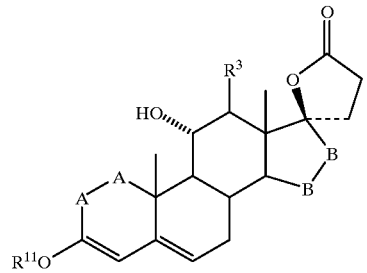

wherein —A—A—, —B—B—, and $R^3$ are as defined in Formula IV, and $R^{11}$ is $C_1$ to $C_4$ alkyl.

A compound of Formula 104A corresponds to Formula 104 wherein each of —A—A— and —B—B— is —CH$_2$—CH$_2$—, and $R^3$ is hydrogen. Compounds within the scope of Formula 104 may be prepared by thermal decomposition of a compound of Formula 103.

A compound of Formula 103 corresponds to the structure:

103

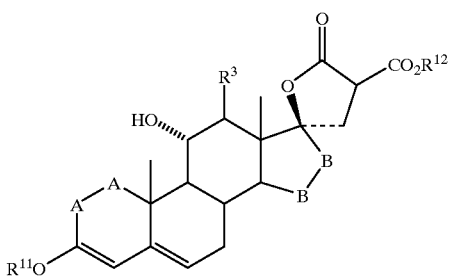

wherein —A—A—, —B—B—, $R^3$ and $R^{11}$ are as defined in Formula 104.

A compound of Formula 103A corresponds to is Formula 103 wherein each of —A—A— and —B—B— is —CH$_2$—CH$_2$—, and $R^3$ is hydrogen. Compounds within the scope of Formula 103 may be prepared by reaction of a corresponding compound of Formula 102 with a dialkyl malonate in the presence of a base such as an alkali metal alkoxide.

A compound of Formula 102 corresponds to the structure:

102

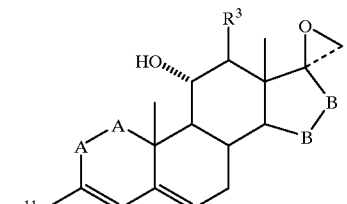

wherein —A—A—, —B—B—, $R^3$ and $R^{11}$ are as defined in Formula 104.

A compound of Formula 102A corresponds to Formula 102 wherein each of —A—A— and —B—B— is —CH$_2$—CH$_2$—, and $R^3$ is hydrogen. Compounds within the scope of Formula 102 may be prepared by reaction of a corresponding compound of Formula 101 with a trialkyl sulfonium compound in the presence of a base.

A compound of Formula 101 corresponds to the structure:

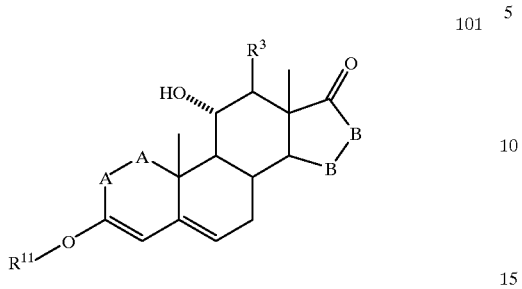

101 wherein —A—A—, —B—B—, $R^3$ and $R^{11}$ are as defined in Formula 104.

A compound of Formula 101A corresponds to Formula 101 wherein each of —A—A— and —B—B— is —CH$_2$—CH$_2$—, and $R^3$ is hydrogen. Compounds within the scope of Formula 101 may be prepared by reaction of 11α-hydroxyandrostene-3,17-dione or other compound of Formula XXXVI with a trialkyl orthoformate in the presence of an acid.

Based on the disclosure of specific reaction schemes as set out hereinbelow, it will be apparent which of these compounds have the greatest utility relative to a particular reaction scheme. Use of the compounds of this invention are useful as intermediates for epoxymexrenone and other steroids.

Other objects and features will be in part apparent and in part pointed out hereinafter.

BRIEF DESCRIPTION OF THE DRAWINGS

Corresponding reference characters indicate corresponding parts throughout the drawings.

DESCRIPTION OF THE PREFERRED EMBODIMENTS

Figure 1:
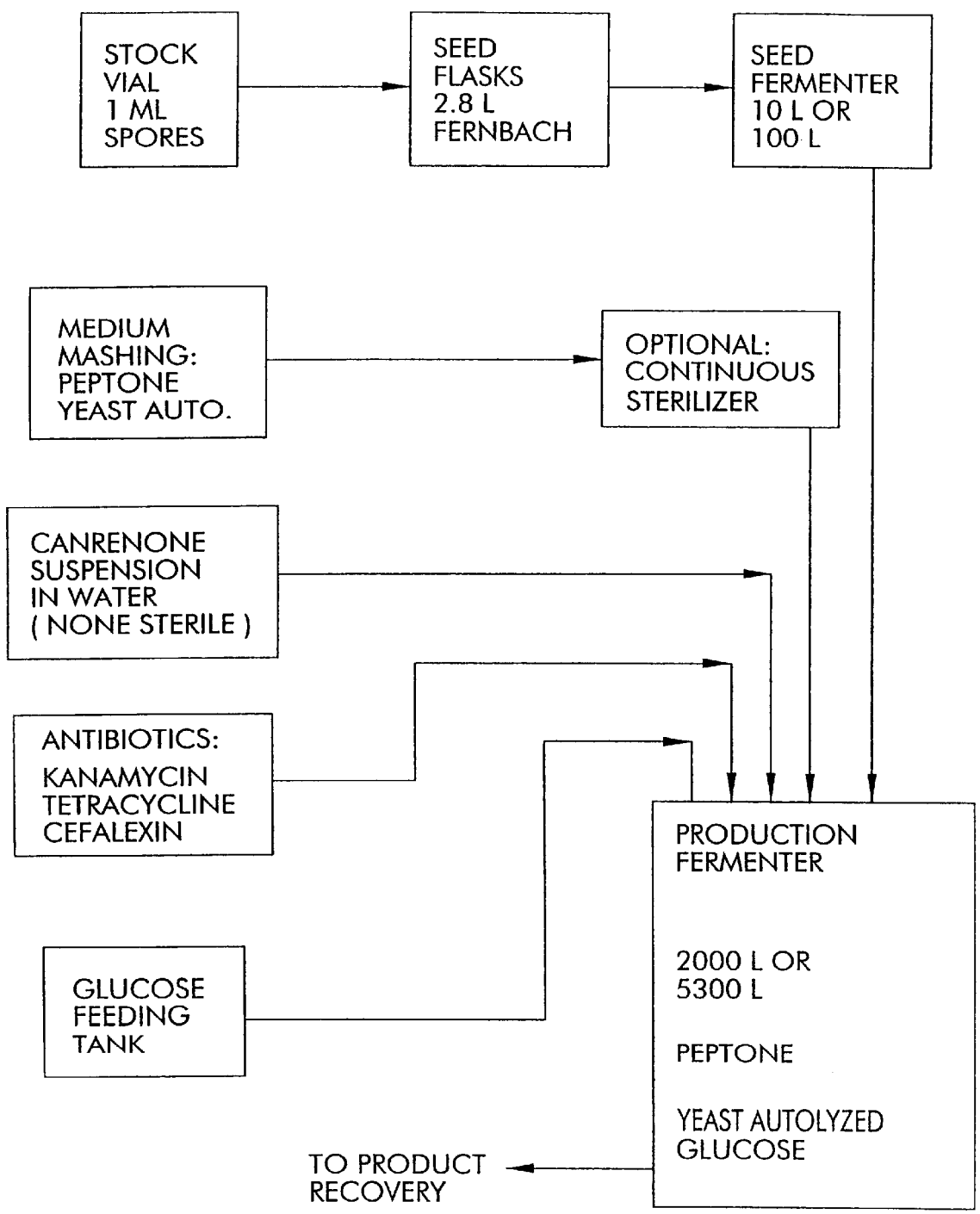
FIG. 1 is a schematic flow sheet of a process for the bioconversion of canrenone or a canrenone derivative to the corresponding 11α-hydroxy compound.

In accordance with the present invention, various novel process schemes have been devised for the preparation of epoxymexrenone and other compounds corresponding Formula I:

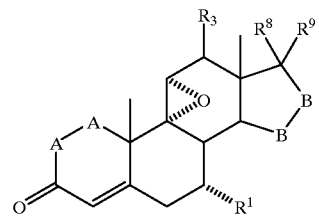

I wherein:
—A—A— represents the group —CHR$^4$—CHR$^5$— or —CR$^4$=CR$^5$—

$R^3$, $R^4$ and $R^5$ are independently selected from the group consisting of hydrogen, halo, hydroxy, lower alkyl, lower alkoxy, hydroxyalkyl, alkoxyalkyl, hydroxycarbonyl, cyano, aryloxy, $R^1$ represents an alpha-oriented lower alkoxycarbonyl or hydroxyalkyl radical, —B—B— represents the group —CHR$^6$—CHR$^7$— or an alpha- or beta-oriented group:

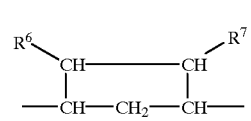

III where $R^6$ and $R^7$ are independently selected from the group consisting of hydrogen, halo, lower alkoxy, acyl, hydroxyalkyl, alkoxyalkyl, hydroxycarbonyl, alkyl, alkoxycarbonyl, acyloxyalkyl, cyano, aryloxy, and $R^8$ and $R^9$ are independently selected from the group consisting of hydrogen, halo, lower alkoxy, acyl, hydroxyalkyl, alkoxyalkyl, hydroxycarbonyl, alkyl, alkoxycarbonyl, acyloxyalkyl, cyano, aryloxy, or $R^8$ and $R^9$ together comprise a carbocyclic or heterocyclic ring structure, or $R^8$ or $R^9$ together with $R^6$ or $R^7$ comprise a carbocyclic or heterocyclic ring structure fused to the pentacyclic D ring.

Unless stated otherwise, organic radicals referred to as "lower" in the present disclosure contain at most 7, and preferably from 1 to 4, carbon atoms.

A lower alkoxycarbonyl radical is preferably one derived from an alkyl radical having from 1 to 4 carbon atoms, such as methyl, ethyl, propyl, isopropyl, butyl, isobutyl, sec.-butyl and tert.-butyl; especially preferred are methoxycarbonyl, ethoxycarbonyl and isopropoxycarbonyl. A lower alkoxy radical is preferably one derived from one of the above-mentioned $C_1$–$C_4$ alkyl radicals, especially from a primary $C_1$–$C_4$ alkyl radical; especially preferred is methoxy. A lower alkanoyl radical is preferably one derived from a straight-chain alkyl having from 1 to 7 carbon atoms; especially preferred are formyl and acetyl.

A methylene bridge in the 15,16-position is preferably β-oriented.

A preferred class of compounds that may be produced in accordance with the methods of the invention are the 20-spiroxane compounds described in U.S. Pat. No. 4,559,332, i.e., those corresponding to Formula IA:

IA

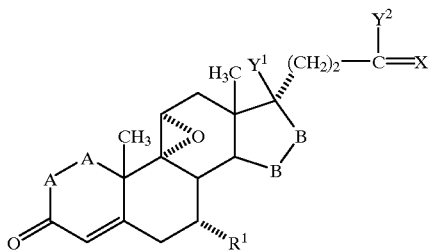

where:
—A—A— represents the group —$CH_2$—$CH_2$— or —CH=CH—,
—B—B— represents the group —$CH_2$—$CH_2$— or an alpha- or beta-oriented group of Formula IIIA:

IIIA

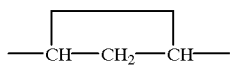

$R^1$ represents an alpha-oriented lower alkoxycarbonyl or hydroxycarbonyl radical,
X represents two hydrogen atoms, oxo or =S
$Y^1$ and $Y^2$ together represent the oxygen bridge —O—, or
$Y^1$ represents hydroxy, and
$Y^2$ represents hydroxy, lower alkoxy or, if X represents $H_2$, also lower alkanoyloxy, Preferably, 20-spiroxane compounds produced by the novel methods of the invention are those of Formula I in which $Y^1$ and $Y^2$ together represent the oxygen bridge —O—.

Especially preferred compounds of the formula I are those in which X represents oxo.

Of compounds of the 20-spiroxane compounds of Formula IA in which X represents oxo there are most especially preferred those in which $Y^1$ together with $Y^2$ represents the oxygen bridge —O—.

As already mentioned, 17β-hydroxy-21-carboxylic acid may also be in the form of their salts. There come into consideration especially metal and ammonium salts, such as alkali metal and alkaline earth metal salts, for example sodium, calcium, magnesium and, preferably, potassium, salts, and ammonium salts derived from ammonia or a suitable, preferably physiologically tolerable, organic nitrogen-containing base. As bases there come into consideration not only amines, for example lower alkylamines (such as triethylamine), hydroxy-lower alkylamines [such as 2-hydroxyethylamine, di-(2-hydroxyethyl)-amine or tri-(2-hydroxyethyl)-amine], cycloalkylamines (such as dicyclohexylamine) or benzylamines (such as benzylamine and N,N'-dibenzylethylenediamine), but also nitrogen-containing heterocyclic compounds, for example those of aromatic character (such as pyridine or quinoline) or those having an at least partially saturated heterocyclic ring (such as N-ethylpiperidine, morpholine, piperazine or N,N'-dimethylpiperazine).

Also included amongst preferred compounds are alkali metal salts, especially potassium salts, of compounds of the formula IA in which $R^1$ represents alkoxycarbonyl, with X representing oxo and each of $Y^1$ and $Y^2$ representing hydroxy.

Especially preferred compounds of the formula I and IA are, for example, the following:

9α,11α-epoxy-7α-methoxycarbonyl-20-spirox-4-ene-3,21-dione,

9α,11α-epoxy-7α-ethoxycarbonyl-20-spirox-4-ene-3,21-dione,

9α,11α-epoxy-7α-isopropoxycarbonyl-20-spirox-4-ene-3,21-dione, and the 1,2-dehydro analogue of each of the compounds, 9α,11α-epoxy-6α,7α-methylene-20-spirox-4-ene-3,21-dione, 9α,11α-epoxy-6β,7β-methylene-20-spirox-4-ene-3,21-dione, 9α,11α-epoxy-6β,7β;15β,16β-bismethylene-20-spirox-4-ene-3,21-dione, and the 1,2-dehydro analogue of each of these compounds, 9α,11α-epoxy-7α-methoxycarbonyl-17β-hydroxy-3-oxo-pregn-4-ene-21-carboxylic acid, 9α,11α-epoxy-7α-ethoxycarbonyl-17β-hydroxy-3-oxo-pregn-4-ene-21-carboxylic acid, 9α,11α-epoxy-7α-isopropoxycarbonyl-17β-hydroxy-3-oxo-pregn-4-ene-21-carboxylic acid, 9α,11α-epoxy-17β-hydroxy-6α,7α-methylene- 3-oxo-pregn-4-ene-21-carboxylic acid, 9α,11α-epoxy-17β-hydroxy-6β,7β-methylene-3-oxo-pregn-4-ene-21-carboxylic acid, 9α,11α-epoxy-17β-hydroxy-6β,7β;15β,16β-bismethylene-3-oxo-pregn-4-ene-21-carboxylic acid, and alkali metal salts, especially the potassium salt or ammonium of each of these acids, and also a corresponding 1,2-dehydro analogue of each of the mentioned carboxylic acids or of a salt thereof.

9α,11α-epoxy-15β,16β-methylene-3,21-dioxo-20-spirox-4-ene-7α-carboxylic acid methyl ester, ethyl ester and isopropyl ester, 9α,11α-epoxy-1565β,16β-methylene-3,21-dioxo-20-spiroxa-1,4-diene-7α-carboxylic acid methyl ester, ethyl ester and isopropyl ester, and also 9α,11α-epoxy-3-oxo-20-spirox-4-ene-7α-carboxylic acid methyl ester, ethyl ester and isopropyl ester, 9α,11α-epoxy-6β,6β-methylene-20-spirox-4-en-3-one, 9α,11α-epoxy-6β,7β;15β,16β-bismethylene-20-spirox-4-en-3-one, and also 9α,11α-epoxy,17β-hydroxy-17α(3-hydroxypropyl)-3-oxo-androst-4-ene-7α-carboxylic acid methyl ester, ethyl ester and isopropyl ester, 9α,11α-epoxy,17β-hydroxy-17α-(3-hydroxypropyl)-6α,7α-methylene-androst-4-en-3-one, 9α,11α-epoxy-17β-hydroxy-17α-(3-hydroxypropyl)-6β,7β-methylene-androst-4-en-3-one, 9α,11α-epoxy-17β-hydroxy-17α-(3-hydroxypropyl)-6β,7β;β15,16β-bismethylene-androst-4-en-3-one, including 17α-(3-acetoxypropyl) and 17α-(3-fromyloxypropyl) analogues of the mentioned androstane compounds, and also 1,2-dehydro analogues of all the mentioned compounds of the androst-4-en-3-one and 20-spirox-4-en-3-one series.

The chemical names of the compounds of the Formulae I and IA, and of analogue compounds having the same characteristic structural features, are derived according to current nomenclature in the following manner: for compounds in which $Y^1$ together with $Y^2$ represents —O—, from 20-spiroxane (for example a compound of the formula IA in which X represents oxo and $Y^1$ together with $Y^2$ represents —O— is derived from 20-spiroxan-21-one); for those in which each of $Y^1$ and $Y^2$ represents hydroxy and X represents oxo, from 17β-hydroxy-17α-pregnene-21-carboxylic acid; and for those in which each of $Y^1$ and $Y^2$ represents hydroxy and X represents two hydrogen atoms, from 17β-hydroxy-17α-(3-hydroxypropyl)-androstane. Since the cyclic and open-chain forms, that is to say lactones and 17β-hydroxy-21-carboxylic acids and their salts, respectively, are so closely related to each other that the latter may be considered merely as a hydrated form of the former, there is to be understood hereinbefore and hereinafter, unless specifically stated otherwise, both in end products of the formula I and in starting materials and intermediates of analogous structure, in each case all the mentioned forms together.

In accordance with the invention, several separate process schemes have been devised for the preparation of compounds of Formula I in high yield and at reasonable cost. Each of the synthesis schemes proceeds through the preparation of a series of intermediates. A number of these intermediates are novel compounds, and the methods of preparation of these intermediates are novel processes.

Scheme 1 (Starting With Canrenone or Related Material)

One preferred process scheme for the preparation of compounds of Formula I advantageously begins with canrenone or a related starting material corresponding to Formula XIII

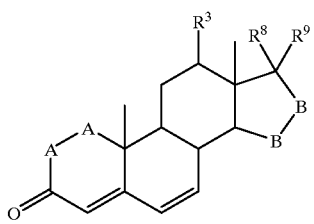

XIII wherein
—A—A— represents the group —CHR⁴—CHR⁵— or —CR⁴=CR⁵—

$R^3$, $R^4$ and $R^5$ are independently selected from the group consisting of hydrogen, halo, hydroxy, lower alkyl, lower alkoxy, hydroxyalkyl, alkoxyalkyl, hydroxycarbonyl, cyano, aryloxy, —B—B— represents the group —CHR⁶—CHR⁷— or an alpha- or beta-oriented group:

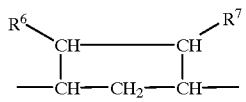

III where $R^6$ and $R^7$ are independently selected from the group consisting of hydrogen, halo, lower alkoxy, acyl, hydroxyalkyl, alkoxyalkyl, hydroxycarbonyl, alkyl, alkoxycarbonyl, acyloxyalkyl, cyano, aryloxy, and $R^8$ and $R^9$ are independently selected from the group consisting of hydrogen, halo, lower alkoxy, acyl, hydroxyalkyl, alkoxyalkyl, hydroxycarbonyl, alkyl, alkoxycarbonyl, acyloxyalkyl, cyano, aryloxy or $R^8$ and $R^9$ together comprise a carbocyclic or heterocyclic ring structure, or $R^8$ and $R^9$ together with $R^6$ or $R^7$ comprise a carbocyclic or heterocyclic ring structure fused to the pentacyclic D ring.

Figure 2:
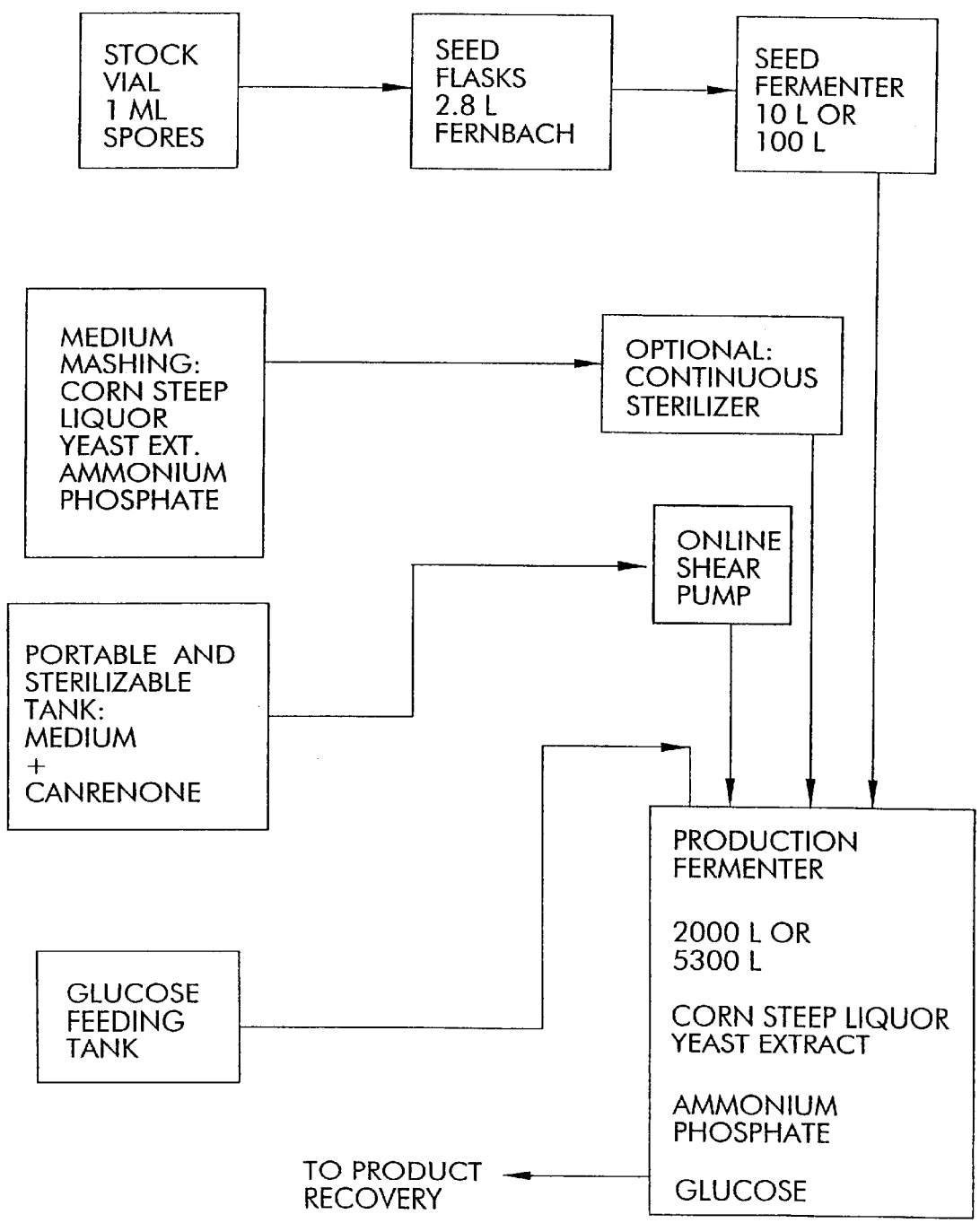
FIG. 2 is a schematic flow sheet of a preferred process for the bioconversion of 11-α-hydroxylation of canrenone and canrenone derivatives.

Using a bioconversion process of the type illustrated in FIGS. 1 and 2, an 11-hydroxy group of α-orientation is introduced in the compound of Formula XIII, thereby producing a compound of Formula VIII:

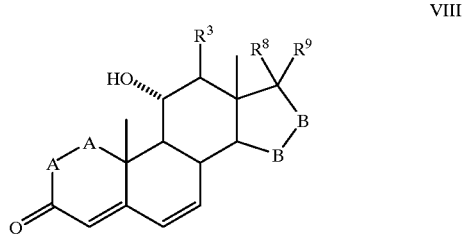

VIII where —A—A—, —B—B—, $R^3$, $R^8$ and $R^9$ are as defined above. Preferably, the compound of Formula XIII has the structure

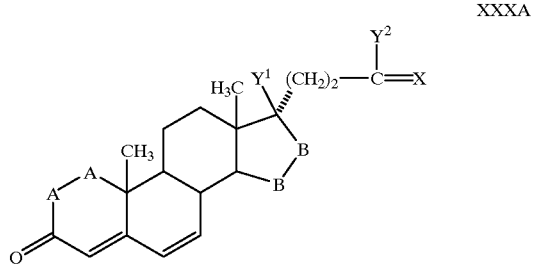

XXXA and the 11α-hydroxy product has the structure

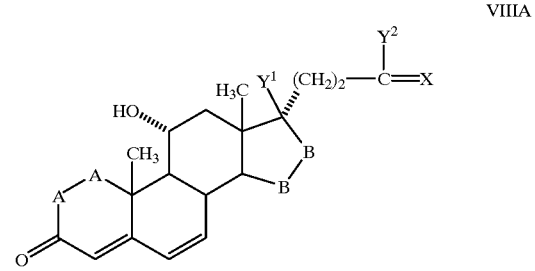

VIIIA in each of which

—A—A— represents the group —CH₂—CH₂— or —CH=CH—,

—B—B— represents the group —CH₂—CH₂— or an alpha- or beta-oriented group:

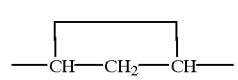

IIIA

X represents two hydrogen atoms, oxo or =S, $Y^1$ and $Y^2$ together represent the oxygen bridge —O—, or $Y^1$ represents hydroxy, and $Y^2$ represents hydroxy, lower alkoxy or, if X represents H₂, also lower alkanoyloxy, and salts of compounds in which X represents oxo and $Y^2$ represents hydroxy-, and the compound of Formula VIII produced in the reaction corresponds to Formula VIIIA

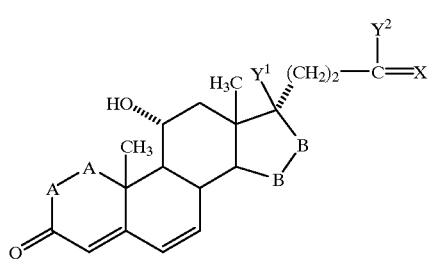

VIIIA wherein —A—A—, —B—B—, $Y^1$, $Y^2$, and X are as defined in Formula XXXA. More preferably, $R^8$ and $R^9$ together form the 20-spiroxane structure:

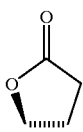

XXXIII

—A—A— and —B—B— are each —$CH_2$—$CH_2$—, and $R^3$ is hydrogen.

Among the preferred organisms that can be used in this hydroxylation step are *Aspergillus ochraceus* NRRL 405, *Aspergillus ochraceus* ATCC 18500, *Aspergillus niger* ATCC 16888 and ATCC 26693, *Aspergillus nidulans* ATCC 11267, *Rhizopus oryzae* ATCC 11145, *Rhizopus stolonifer* ATCC 6227b, *streptomyces fradiae* ATCC 10745, *Bacillus megaterium* ATCC 14945, *Pseudomonas cruciviae* ATCC 13262, and *Trichothecium roseum* ATCC 12543. Other preferred organisms include *Fusarium oxysporum* f.sp.*cepae* ATCC 11171 and *Rhizopus arrhizus* ATCC 11145.

Other organisms that have exhibited activity for this reaction include *Absidia coerula* ATCC 6647, *Absidia glauca* ATCC 22752, *Actinomucor elegans* ATCC 6476, *Aspergillus flavipes* ATCC 1030, *Aspergillus fumigatus* ATCC 26934, *Beauveria bassiana* ATCC 7159 and ATCC 13144, *Botryosphaeria obtusa* IMI 038560, *Calonectria decora* ATCC 14767, *Chaetomium cochliodes* ATCC 10195, *Corynespora cassiicola* ATCC 16718, *Cunninghamella blakesleeana* ATCC 8688a, *Cunninghamella echinulata* ATCC 3655, *Cunninghamella elegans* ATCC 9245, *Curvularia clavata* ATCC 22921, *Curvularia lunata* ACTT 12071, *Cylindrocarpon radicicola* ATCC 1011, *Epicoccum humicola* ATCC 12722, *Gongronella butleri* ATCC 22822, *Hypomyces chrysospermus*, *Mortierella isabellina* ATCC 42613, *Mucor mucedo* ATCC 4605, *Mucor griseo-cyanus* ATCC 1207A, *Myrothecium verrucaria* ATCC 9095, *Nocardia corallina*, *Paecilomyces carneus* ATCC 46579, *Penicillum patulum* ATCC 24550, *Pithomyces atro-olivaceus* IFO 6651, *Pithomyces cynodontis* ATCC 26150, *Pycnosporium sp.* ATCC 12231, *Saccharopolyspora erythrae* ATCC 11635, *Sepedonium chrysospermum* ATCC 13378, *Stachylidium bicolor* ATCC 12672, *Streptomyces hygroscopicus* ATCC 27438, *Streptomyces purpurascens* ATCC 25489, *Syncephalastrum racemosum* ATCC 18192, *Thamnostylum piriforme* ATCC 8992, *Thielavia terricola* ATCC 13807, and *Verticillium theobromae* ATCC 12474.

Additional organisms that may be expected to show activity for the 11a-hydroxylation include *Cephalosporium aphidicola* (Phytochemistry (1996), 42(2), 411–415), *Cochliobolus lunatas* (J. Biotechnol. (1995), 42(2), 145–150), *Tieghemella orchidis* (Khim.-Farm.Zh. (1986), 20(7), 871–876), *Tieghemella hyalospora* (Khim.-Farm.Zh. (1986), 20(7), 871–876), *Monosporium olivaceum* (Acta Microbiol. Pol., Ser. B. (1973), 5(2), 103–110), *Aspergillus ustus* (Acta Microbiol. Pol., Ser. B. (1973), 5(2), 103–110), *Fusarium graminearum* (Acta Microbiol. Pol., Ser. B. (1973), 5(2), 103–110), *Verticillium glaucum* (Acta Microbiol. Pol., Ser. B. (1973), 5(2), 103–110), and *Rhizopus nigricans* (J. Steroid Biochem. (1987), 28(2), 197–201).

Preparatory to production scale fermentation for hydroxylation of canrenone or other substrates of Formula XIII, an inoculum of cells is prepared in a seed fermentation system comprising a seed fermenter, or a series of two or more seed fermenters. A working stock spore suspension is introduced into the first seed fermenter, together with a nutrient solution for growth of cells. If the volume of inoculum desired or needed for production exceeds that produced in the first seed fermenter, the inoculum volume may be progressively and geometrically amplified by progression through the remaining fermenters in the seed fermentation train. Preferably, the inoculum produced in the seed fermentation system is of sufficient volume and viable cells for achieving rapid initiation of reaction in the production fermenter, relatively short production batch cycles, and high production fermenter activity. Whatever the number of vessels in a train of seed fermenters, the second and subsequent seed fermenters are preferably sized so that the extent of dilution at each step in the train is essentially the same. The initial dilution of inoculum in each seed fermenter can be approximately the same as the dilution in the production fermenter. Canrenone or other Formula XIII substrate is charged to the production fermenter along with inoculum and nutrient solution, and the hydroxylation reaction conducted there.

The spore suspension charged to the seed fermentation system is from a vial of working stock spore suspension taken from a plurality of vials constituting a working stock cell bank that is stored under cryogenic conditions prior to use. The working stock cell bank is in turn derived from a master stock cell bank that has been prepared in the following manner. A spore specimen obtained from an appropriate source, e.g., ATCC, is initially suspended in an aqueous medium such as, for example, saline solution, nutrient solution or a surfactant solution, (e.g., a nonionic surfactant such as Tween 20 at a concentration of about 0.001% by weight), and the suspension distributed among culture plates, each plate bearing a solid nutrient mixture, typically based on a non-digestible polysaccharide such as agar, where the spores are propagated. The solid nutrient mixture preferably contains between about 0.5% and about 5% by weight glucose, between about 0.05% and about 5% by weight of a nitrogen source, e.g., peptone, between about 0.05% and about 0.5% by weight of a phosphorus source, e.g., an ammonium or alkali metal phosphate such as dipotassium hydrogen phosphate, between about 0.25% and about 2.5% by weight yeast lysate or extract (or other amino acid source such as meat extract or brain heart infusion), between about 1% and about 2% by weight agar or other non-digestible polysaccharide. Optionally, the solid nutrient mixture may further comprise and/or contain between about 0.1% and about 5% by weight malt extract. The pH of the solid nutrient mixture is preferably between about 5.0 and about 7.0, adjusted as required by alkali metal hydroxide or orthophosphoric acid. Among useful solid growth media are the following:

| | | |
|---|---|---|
| 1. | Solid Medium #1: | 1% glucose, 0.25% yeast extract, 0.3% K$_2$HPO$_4$ and 2% agar (Bacto); pH adjusted to 6.5 with 20% NaOH. |
| 2. | Solid Medium #2: | 2% peptone (Bacto), 1% yeast extract (Bacto), 2% glucose and 2% agar (Bacto); pH adjusted to 5 with 10% H$_3$PO$_4$. |
| 3. | Solid Medium #3: | 0.1% peptone (Bacto), 2% malt extract (Bacto), 2% glucose and 2% agar (Bacto); pH as is 5.3. |
| 4. | Liquid Medium: | 5% blackstrap molasses, 0.5% cornsteep liquor, 0.25% glucose, 0.25% NaCl and 0.5% KH$_2$PO$_4$, pH adjusted to 5.8. |
| 5. | Difco Mycological agar (low pH). | |

The number of agar plates used in the development of a master stock cell bank can be selected with a view to future demands for master stock, but typically about 15 to about 30 plates are so prepared. After a suitable period of growth, e.g., 7 to 10 days, the plates are scraped in the presence of an aqueous vehicle, typically saline or buffer, for harvesting the spores, and the resulting master stock suspension is divided among small vials, e.g., one ml. in each of a plurality of 1.5 ml vials. To prepare a working stock spore suspension for use in research or production fermentation operations, the contents of one or more of these second generation master stock vials can be distributed among and incubated on agar plates in the manner described above for the preparation of master stock spore suspension. Where routine manufacturing operations are contemplated, as many as 100 to 400 plates may be used to generate second generation working stock. Each plate is scraped into a separate working stock vial, each vial typically containing one ml of the inoculum produced. For permanent preservation, both the master stock suspension and the second generation production inoculum are advantageously stored in the vapor space of a cryogenic storage vessel containing liquid N$_2$ or other cryogenic liquid.

In the process illustrated in FIG. 1, aqueous growth medium is prepared which includes a nitrogen source such as peptone, a yeast derivative or equivalent, glucose, and a source of phosphorus such as a phosphate salt. Spores of the microorganism are cultured in this medium in the seed fermentation system. The preferred microorganism is *Aspergillus ochraceus* NRRL 405 (ATCC 18500). The seed stock so produced is then introduced into the production fermenter together with the substrate of Formula XIII. The fermentation broth is agitated and aerated for a time sufficient for the reaction to proceed to the desired degree of completion.

The medium for the seed fermenter preferably comprises an aqueous mixture which contains: between about 0.5% and about 5% by weight glucose, between about 0.05% and about 5% by weight of a nitrogen source, e.g., peptone, between about 0.05% and about 0.5% by weight of a phosphorus source, e.g., an ammonium or alkali metal phosphate such as ammonium phosphate monobasic or dipotassium hydrogen phosphate, between about 0.25% and about 2.5% by weight yeast lysate or extract (or other amino acid source such as distiller's solubles), between about 1% and about 2% by weight agar or other non-digestible polysaccharide. A particularly preferred seed growth medium contains about 0.05% and about 5% by weight of a nitrogen source such as peptone, between about 0.25% and about 2.5% by weight of autolyzed yeast or yeast extract, between about 0.5% and about 5% by weight glucose, and between about 0.05% by weight and about 0.5% by weight of a phosphorus source such as ammonium phosphate monobasic. Especially economical process operations are afforded by the use of another preferred seed culture which contains between about 0.5% and about 5% by weight corn steep liquor, between about 0.25% and about 2.5% autolyzed yeast or yeast extract, between about 0.5% and about 5% by weight glucose and about 0.05% and about 0.5% by weight ammonium phosphate monobasic. Corn steep liquor is a particularly economical source of proteins, peptides, carbohydrates, organic acids, vitamins, metal ions, trace matters and phosphates. Mash liquors from other grains may be used in place of, or in addition to, corn steep liquor. The pH of the medium is preferably adjusted within the range of between about 5.0 and about 7.0, e.g., by addition of an alkali metal hydroxide or orthophosphoric acid. Where corn steep liquor serves as the source of nitrogen and carbon, the pH is preferably adjusted within the range of about 6.2 to about 6.8. The medium comprising peptone and glucose is preferably adjusted to a pH between.about 5.4 and about 6.2. Among useful growth media for use in seed fermentation:

1. Medium #1: 2% peptone, 2% yeast autolised (or yeast extract) and 2% glucose; pH adjusted to 5.8 with 20% NaOH.
2. Medium #2: 3% corn steep liquor, 1.5% yeast extract 0.3% ammonium phosphate monobasic and 3% glucose; pH adjusted to 6.5 with 20% NaOH.

Spores of the microorganism are introduced into this medium from a vial typically containing in the neighborhood of $10^9$ spores per ml. of suspension. Optimal productivity of seed generation is realized where dilution with growth medium at the beginning of a seed culture does not reduce the spore population density below about $10^7$ per ml. Preferably, the spores are cultured in the seed fermentation system until the packed mycelial volume (PMV) in the seed fermenter is at least about 20%, preferably 35% to 45%. Since the cycle in the seed fermentation vessel (or any vessel of a plurality which comprise a seed fermentation train) depends on the initial concentration in that vessel, it may be desirable to provide two or three seed fermentation stages to accelerate the overall process. However, it is preferable to avoid the use of significantly more than three seed fermenters in series, since activity may be compromised if seed fermentation is carried through an excessive number of stages. The seed culture fermentation is conducted under agitation at a temperature in the range of about 23° to about 37° C., preferably in range of between about 24° and about 28° C.

Culture from the seed fermentation system is introduced into a production fermenter, together with a production growth medium. In one embodiment of the invention, non-sterile canrenone or other substrate of Formula XIII serves as the substrate for the reaction. Preferably, the substrate is added to the production fermenter in the form of a 10% to 30% by weight slurry in growth medium. To increase the surface area available for 11α-hydroxylation reaction, the particle size of the Formula XIII substrate is reduced by passing the substrate through an off line micronizer prior to introduction into the fermenter. A sterile nutrient feed stock containing glucose, and a second sterile nutrient solution containing a yeast derivative such as autolyzed yeast (or equivalent amino acid formulation based on alternative sources such as distiller's solubles), are also separately introduced. The medium comprises an aqueous mixture containing: between about 0.5% and about 5% by weight glucose, between about 0.05% and about 5% by weight of a nitrogen source, e.g., peptone, between about 0.05% and about 0.5% by weight of a phosphorus source, e.g., an ammonium or alkali metal phosphate such as dipotassium hydrogen phosphate, between about 0.25% and about 2.5% by weight yeast lysate or extract (or other amino acid source such as distiller's solubles), between about 1% and about 2% by weight agar or other non-digestible polysaccharide. A particularly preferred production growth medium contains about 0.05% and about 5% by weight of a nitrogen source such as peptone, between about 0.25% and about 2.5% by weight of autolyzed yeast or yeast extract, between about 0.5% and about 5% by weight glucose, and between about 0.05% and about 0.5% by weight of a phosphorus source such as ammonium phosphate monobasic. Another preferred production medium contains between about 0.5% and about 5% by weight corn steep liquor, between about 0.25% and about 2.5% autolyzed yeast or yeast extract, between about 0.5% and about 5% by weight glucose and about 0.05% and about 0.5% by weight ammonium phosphate monobasic. The pH of the production fermentation medium is preferably adjusted in the manner described above for the seed fermentation medium, with the same preferred ranges for the pH of peptone/glucose based media and corn steep liquor based media, respectively. Useful bioconversion growth media are set forth below:

1. Medium #1: 2% peptone, 2% yeast autolised (or yeast extract) and 2% glucose; pH adjusted to 5.8 with 20% NaOH.
2. Medium #2: 1% peptone, 1% yeast autolised (or yeast extract) and 2% glucose; pH adjusted to 5.8 with 20% NaOH.
3. Medium #3: 0.5% peptone, 0.5% yeast autolised (or yeast extract) and 0.5% glucose; pH adjusted to 5.8 with 20% NaOH.
4. Medium #4: 3% corn steep liquor, 1.5% yeast extract 0.3% ammonium phosphate monobasic and 3% glucose; pH adjusted to 6.5 with 20% NaOH.
5. Medium #5: 2.55% corn steep liquor, 1.275% yeast extract 0.255% ammonium phosphate monobasic and 3% glucose; pH adjusted to 6.5 with 20% NaOH.
6. Medium #6: 2.1% corn steep liquor, 1.05% yeast extract 0.21% ammonium phosphate monobasic and 3% glucose; pH adjusted to 6.5 with 20% NaOH.

Non-sterile canrenone and sterile nutrient solutions are chain fed to the production fermenter in five to twenty, preferably ten to fifteen, preferably substantially equal, portions each over the production batch cycle. Advantageously, the substrate is initially introduced in an amount sufficient to establish a concentration of between about 0.1% by weight and about 3% by weight, preferably between about 0.5% and about 2% by weight, before inoculation with seed fermentation broth, then added periodically, conveniently every 8 to 24 hours, to a cumulative proportion of between about 1% and about 8% by weight. Where additional substrate is added every 8 hour shift, total addition may be slightly lower, e.g., 0.25% to 2.5% by weight, than in the case where substrate is added only on a daily basis. In the latter instance cumulative canrenone addition may need to be in the range 2% to about 8% by weight. The supplemental nutrient mixture fed during the fermentation reaction is preferably a concentrate, for example, a mixture containing between about 40% and about 60% by weight sterile glucose, and between about 16% and about 32% by weight sterile yeast extract or other sterile source of yeast derivative (or other amino acid source). Since the substrate fed to the production fermenter of FIG. 1 is non-sterile, antibiotics are periodically added to the fermentation broth to control the growth of undesired organisms. Antibiotics such as kanamycin, tetracycline, and cefalexin can be added without disadvantageously affecting growth and bioconversion. Preferably, these are introduced into the fermentation broth in a concentration, e.g., of between about 0.0004% and about 0.002% based on the total amount of the broth, comprising, e.g., between about 0.0002% and about 0.0006% kanamicyn sulfate, between about 0.0002% and about 0.006% tetracycline HCl and/or between about 0.001% and about 0.003% cefalexin, again based on the total amount of broth.

Typically, the production fermentation batch cycle is in the neighborhood of 80–160 hours. Thus, portions of each of the Formula XIII substrate and nutrient solutions are typically added every 2 to 10 hours, preferably every 4 to 6 hours. Advantageously, an antifoam is also incorporated in the seed fermentation system, and in the production fermenter.

Preferably, in the process of FIG. 1, the inoculum charge to the production fermenter is about 0.5 to about 7%, more preferably about 1 to about 2%, by volume based on the total mixture in the fermenter, and the glucose concentration is maintained between about 0.01% and about 1.0%, preferably between about 0.025% and about 0.5%, more preferably between about 0.05% and about 0.25% by weight with periodic additions that are preferably in portions of about 0.05% to about 0.25% by weight, based on the total batch charge. The fermentation temperature is conveniently controlled within a range of about 20° to about 37° C., preferably about 24° C. to about 28° C., but it may be desirable to step down the temperature during the reaction, e.g., in 2° C. increments, to maintain the packed mycelium volume (PMV) below about 60%, more preferably below about 50%, and thereby prevent the viscosity of the fermentation broth from interfering with satisfactory mixing. If the biomass growth extends above the liquid surface, substrate retained within the biomass may be carried out of the reaction zone and become unavailable for the hydroxylation reaction. For productivity, it is desirable to reach a PMV in the range of 30 to 50%, preferably 35% to 45%, within the first 24 hours of the fermentation reaction, but thereafter conditions are preferably managed to control further growth within the limits stated above. During reaction, the pH of the fermentation medium is controlled at between about 5.0 and about 6.5, preferably between about 5.2 and about 5.8, and the fermenter is agitated at a rate of between about 400 and about 800 rpm. A dissolved oxygen level of at least about 10% of saturation is achieved by aerating the batch at between about 0.2 and about 1.0 vvm, and maintaining the pressure in the head space of the fermenter at between about atmospheric and about 1.0 bar gauge, most preferably in the neighborhood of about 0.7 bar gauge. Agitation rate may also been increased as necessary to maintain minimum dissolved oxygen levels. Advantageously, the dissolved oxygen is maintained at well above 10%, in fact as high as 50% to promote conversion of substrate. Maintaining the pH in the range of 5.5±0.2 is also optimal for bioconversion. Foaming is controlled as necessary by addition of a common antifoaming agent. After all substrate has been added, reaction is preferably continued until the molar ratio of Formula VIII product to remaining unreacted Formula XIII substrate is at least about 9 to 1. Such conversion may be achieve within the 80–160 hour batch cycle indicated above.

It has been found that high conversions are associated with depletion of initial nutrient levels below the initial charge level, and by controlling aeration rate and agitation rate to avoid splashing of substrate out of the liquid broth.

Figure 3:
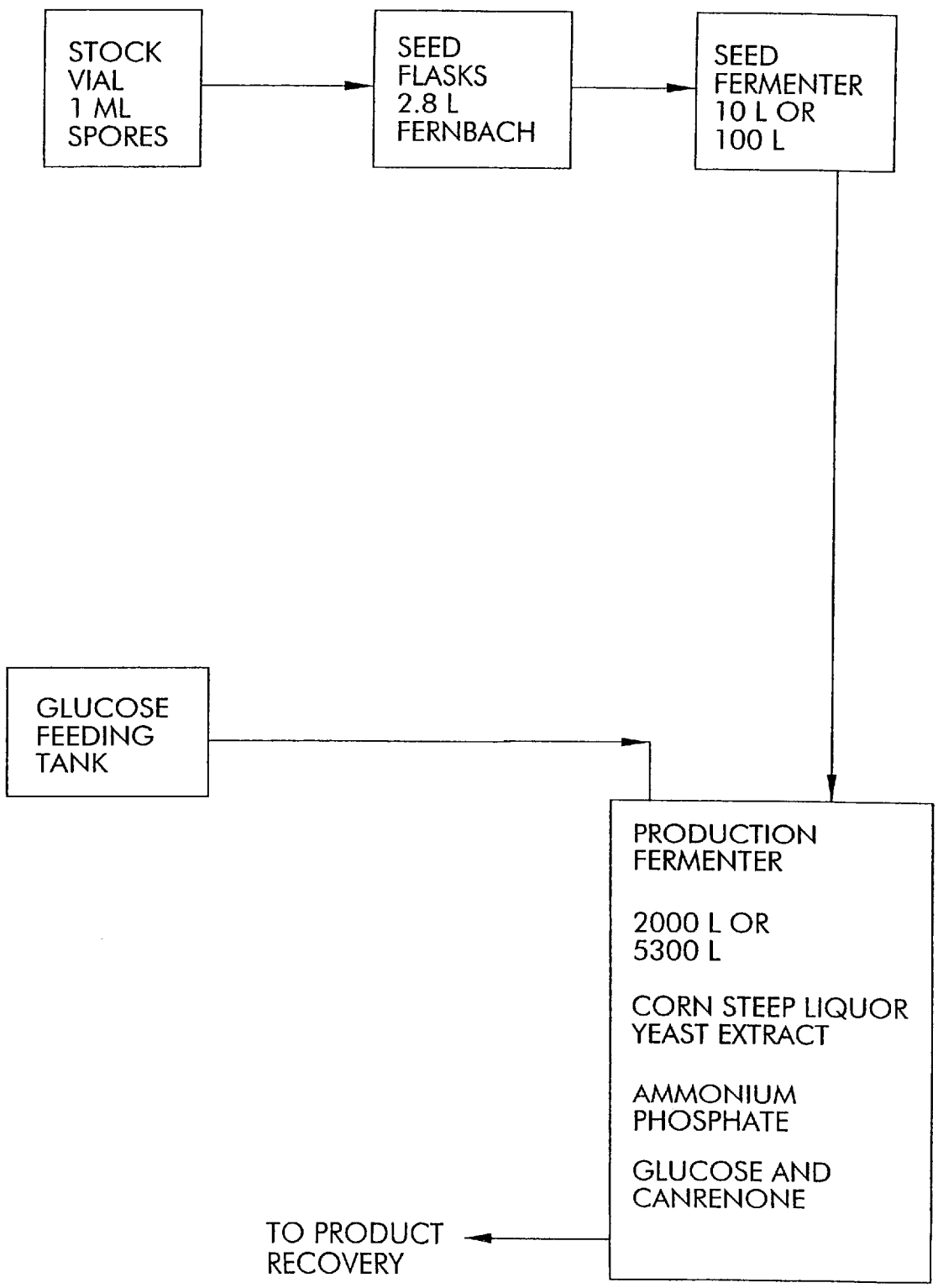
FIG. 3 is a schematic flow sheet of a particularly preferred process for the bioconversion of 11-α-hydroxylation of canrenone and canrenone derivatives.

In the process of FIG. 1, the nutrient level was depleted to and then maintained at no greater than about 60%, preferably about 50%, of the initial charge level; while in the processes of FIGS. 2 and 3, the nutrient level was reduced to and maintained at no greater than about 80%, preferably about 70%, of the initial charge level. Aeration rate is preferably no greater than one vvm, more preferably in the range of about 0.5 vvm; while agitation rate is preferably not greater than 600 rpm.

A particularly preferred process for preparation of a compound of Formula VIII is illustrated in FIG. 2. Again the preferred microorganism is Aspergillus ochraceus NRRL 405 (ATCC 18500). In this process, growth medium preferably comprises between about 0.5% and about 5% by weight corn steep liquor, between about 0.5% and about 5% by weight glucose, between about 0.1% and about 3% by weight yeast extract, and between about 0.05% and about 0.5% by weight ammonium phosphate. However, other production growth media as described herein may also be used. The seed culture is prepared essentially in the manner described for the process of FIG. 1, using any of the seed fermentation media described herein. A suspension of non-micronized canrenone or other Formula XIII substrate in the growth medium is prepared aseptically in a blender, preferably at a relatively high concentration of between about 10% and about 30% by weight substrate. Preferably, aseptic preparation may comprise sterilization or pasteurization of the suspension after mixing. The entire amount of sterile substrate suspension required for a production batch is introduced into the production fermenter at the beginning of the batch, or by periodical chain feeding. The particle size of the substrate is reduced by wet milling in an on-line shear pump which transfers the slurry to the production fermenter, thus obviating the need for use of an off line micronizer. Where aseptic conditions are achieved by pasteurization rather than sterilization, the extent of agglomeration may be insignificant, but the use of a shear pump may be desirable to provide positive control of particle size. Sterile growth medium and glucose solution are introduced into the production fermenter essentially in the same manner as described above. All feed components to the production fermenter are sterilized before introduction, so that no antibiotics are required.

Preferably, in operation of the process of FIG. 2, the inoculum is introduced into the production fermenter in a proportion of between about 0.5% and about 7%, the fermentation temperature is between about 20° and about 37° C., preferably between about 24° C. and about 28° C., and the pH is controlled between about 4.4 and about 6.5, preferably between about 5.3 and about 5.5, e.g., by introduction of gaseous ammonia, aqueous ammonium hydroxide, aqueous alkali metal hydroxide, or orthophosphoric acid. As in the process of FIG. 1, the temperature is preferably trimmed to control growth of the biomass so that PMV does not exceed 55–60%. The initial glucose charge is preferably between about 1% and about 4% by weight, most preferably 2.5% to 3.5% by weight, but is preferably allowed to drift below about 1.0% by weight during fermentation. Supplemental glucose is fed periodically in portions of between about 0.2% and about 1.0% by weight based on the total batch charge, so as to maintain the glucose concentration in the fermentation zone within a range of between about 0.1% and about 1.5% by weight, preferably between about 0.25% and about 0.5% by weight. Optionally, nitrogen and phosphorus sources may be supplemented along with glucose. However, because the entire canrenone charge is made at the beginning of the batch cycle, the requisite supply of nitrogen and phosphorus bearing nutrients can also be introduced at that time, allowing the use of only a glucose solution for supplementation during the reaction. The rate and nature of agitation is a significant variable. Moderately vigorous agitation promotes mass transfer between the solid substrate and the aqueous phase. However, a low shear impeller should be used to prevent degradation of the myelin of the microorganisms. Optimal agitation velocity varies within the range of 200 to 800 rpm, depending on culture broth viscosity, oxygen concentration, and mixing conditions as affected by vessel, baffle and impeller configuration. Ordinarily, a preferred agitation rate is in the range of 350–600 rpm. Preferably the agitation impeller provides a downward axially pumping function so as to assist in good mixing of the fermented biomass. The batch is preferably aerated at a rate of between about 0.3 and about 1.0 vvm, preferably 0.4 to 0.8 vvm, and the pressure in the head space of the fermenter is preferably between about 0.5 and about 1.0 bar gauge. Temperature, agitation, aeration and back pressure are preferably controlled to maintain dissolved oxygen in the range of at least about 10% by volume during the bioconversion. Total batch cycle is typically between about 100 and about 140 hours.

Although the principle of operation for the process of FIG. 2 is based on early introduction of substantially the entire canrenone charge, it will be understood that growth of the fermentation broth may be carried out before the bulk of the canrenone is charged. optionally, some portion of the canrenone can also be added later in the batch. Generally, however, at least about 75% of the sterile canrenone charge should be introduced into the transformation fermenter within 48 hours after initiation of fermentation. Moreover, it is desirable to introduce at least about 25% by weight canrenone at the beginning of the fermentation, or at least within the first 24 hours in order to promote generation of the bioconversion enzyme(s).

In a further preferred process as illustrated in FIG. 3, the entire batch charge and nutrient solution are sterilized in the production fermentation vessel prior to the introduction of inoculum. The nutrient solutions that may be used, as well as the preferences among them, are essentially the same as in the process of FIG. 2. In this embodiment of the invention, the shearing action of the agitator impeller breaks down the substrate agglomerates that otherwise tend to form upon sterilization. It has been found that the reaction proceeds satisfactorily if the mean particle size of the canrenone is less than about 200 $\mu$ and at least 75% by weight of the particles are smaller than 240 $\mu$. The use of a suitable impeller, e.g., a disk turbine impeller, at an adequate velocity in the range of 200 to 800 rpm, with a tip speed of at least about 400 cm/sec., has been found to provide a shear rate sufficient to maintain such particle size characteristics despite the agglomeration that tends to occur upon sterilization within the production fermenter. The remaining operation of the process of FIG. 3 is essentially the same as the process of FIG. 2. The processes of FIGS. 2 and 3 offer several distinct advantages over the process of FIG. 1. A particular advantage is the amenability to use of a low cost nutrient base such as corn steep liquor. But further advantages are realized in eliminating the need of antibiotics, simplifying feeding procedures, and allowing for batch sterilization of canrenone or other Formula XIII substrate. Another particular advantage is the ability to use a simple glucose solution rather than a complex nutrient solution for supplementation during the reaction cycle.

In processes depicted in FIGS. 1 to 3, the product of FIG. VIII is a crystalline solid which, together with the biomass, may be separated from the reaction broth by filtration or low speed centrifugation. Alternatively, the product can be extracted from the entire reaction broth with organic solvents. Product of Formula VIII is recovered by solvent extraction. For maximum recovery, both the liquid phase filtrate and the biomass filter or centrifuge cake are treated with extraction solvent, but usually ≧95% of the product is associated with the biomass. Typically, hydrocarbon, ester, chlorinated hydrocarbon, and ketone solvents may be used for extraction. A preferred solvent is a ethyl acetate. Other typically suitable solvents include toluene and methyl isobutyl ketone. For extraction from the liquid phase, it may be convenient to use a volume of solvent approximately equal to the volume of reaction solution which it contacts. To recover product the from the biomass, the latter is suspended in the solvent, preferably in large excess relative to the initial charge of substrate, e.g., 50 to 100 ml. solvent per gram of initial canrenone charge, and the resulting suspension preferably refluxed for a period of 20 minutes to several hours to assure transfer of product to the solvent phase from recesses and pores of the biomass. Thereafter, the biomass is removed by filtration or centrifugation, and the filter cake preferably washed with both fresh solvent and deionized water. Aqueous and solvent washes are then combined and the phases allowed to separate. Formula VIII product is recovered by crystallization from the solution. To maximize yield, the mycelium is contacted twice with fresh solvent. After settling to allow complete separation of the aqueous phase, product is recovered from the solvent phase. Most preferably, the solvent is removed under vacuum until crystallization begins, then the concentrated extract is cooled to a temperature of 0° to 20° C., preferably about 10° to about 15° C. for a time sufficient for crystal precipitation and growth, typically 8 to 12 hours.

The processes of FIG. 2, and especially that of FIG. 3, are particularly preferred. These processes operate at low viscosity, and are amenable to close control of process parameters such as pH, temperature and dissolved oxygen. Moreover, sterile conditions are readily preserved without resort to antibiotics.

The bioconversion process is exothermic, so that heat should be removed, using a jacketed fermenter or a cooling coil within the production fermenter. Alternatively, the reaction broth may be circulated through an external heat exchanger. Dissolved oxygen is preferably maintained at a level of at least about 5%, preferably at least about 10%, by volume, sufficient to provide energy for the reaction and assure conversion of the glucose to $CO_2$ and $H_2O$, by regulating the rate of air introduced into the reactor in response to measurement of oxygen potential in the broth. The pH is preferably controlled at between about 4.5 and about 6.5.

In each of the alternative processes for 11-hydroxylation of the substrate of Formula XIII, productivity is limited by mass transfer from the solid substrate to the aqueous phase, or the phase interface, where reaction is understood to occur. As indicated above, productivity is not significantly limited by mass transfer rates so long as the particle mean particle size of the substrate is reduced to less than about 300μ, and at least 75% by weight of the particles are smaller than 240μ. However, productivity of these processes may be further enhanced in certain alternative embodiments which provide a substantial charge of canrenone or other Formula XIII substrate to the production fermenter in an organic solvent. According to one option, the substrate is dissolved in a water-immiscible solvent and mixed with the aqueous growth medium inoculum and a surfactant. Useful water-immiscible solvents inlcude, for example, DMF, DMSO, $C_6$–$C_{12}$ fatty acids, $C_6$–$C_{12}$ n-alkanes, vegetable oils, sorbitans, and aqueous surfactant solutions. Agitation of this charge generates an emulsion reaction system having an extended interfacial area for mass transfer of substrate from the organic liquid phase to the reaction sites.

A second option is to initially dissolve the substrate in a water miscible solvent such as acetone, methylethyl ketone, methanol, ethanol, or glycerol in a concentration substantially greater than its solubility in water. By preparing the initial substrate solution at elevated temperature, solubility is increased, thereby further increasing the amount of solution form substrate introduced into the reactor and ultimately enhancing the reactor payload. The warm substrate solution is charged to the production fermentation reactor along with the relatively cool aqueous charge comprising growth medium and inoculum. When the substrate solution is mixed with the aqueous medium, precipitation of the substrate occurs. However, under conditions of substantial supersaturation and moderately vigorous agitation, nucleation is favored over crystal growth, and very fine particles of high surface area are formed. The high surface area promotes mass transfer between the liquid phase and the solid substrate. Moreover, the equilibrium concentration of substrate in the aqueous liquid phase is also enhanced in the presence of a water-miscible solvent. Accordingly, productivity is promoted.

Although the microorganism may not necessarily tolerate a high concentration of organic solvent in the aqueous phase, a concentration of ethanol, e.g., in the range of about 3% to about 5% by weight, can be used to advantage.

A third option is to solubilize the substrate in an aqueous cyclodextrin solution. Illustrative cyclodextrins include hydroxypropyl-β-cyclodextrin and methyl-β-cyclodextrin. The molar ratio of substrate:cyclodextrin can be about 1:1 to about 1:1.5, substrate:cyclodextrin. The substrate:cyclodextrin mixture can then be added aseptically to the bioconversion reactor.

11α-Hydroxycanrenone and other products of the 11α-hydroxylation process (Formulae VIII and VIIIA) are novel compounds, which may be isolated by filtering the reaction medium, and extracting the product from the biomass collected on the filtration medium. Conventional organic solvents, e.g., ethyl acetate, acetone, toluene, chlorinated hydrocarbons, and methyl isobutyl ketone may be used for the extraction. The product of Formula VIII may then be recrystallized from an organic solvent of the same type. The compounds of Formula VIII have substantial value as intermediates for the preparation of compounds of Formula I, and especially of Formula IA.

Preferably, the compounds of Formula VIII correspond to Formula VIIIA in which —A—A— and —B—B— are —$CH_2$—$CH_2$—, $R^3$ is hydrogen, lower alkyl or lower alkoxy, and $R^8$ and $R^9$ together constitute the 20-spiroxane ring:

XXXIII

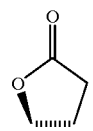

Further in accordance with the process of scheme 1, the compound of Formula VIII is reacted under alkaline conditions with a source of cyanide ion to produce an enamine compound of Formula VII

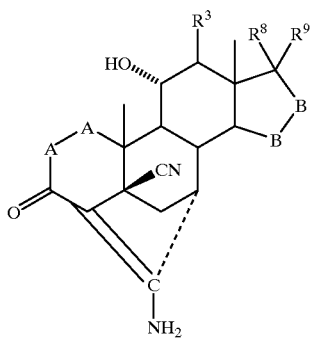

VII wherein —A—A—, $R^3$, —B—B—, $R^8$ and $R^9$ are as defined above. Where the substrate corresponds to Formula VIIIA, the product is of Formula VIIA

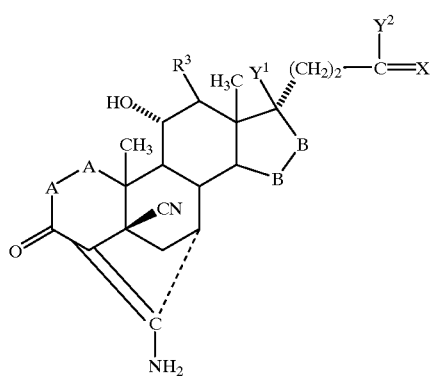

VIIA wherein —A—A—, —B—B—, $R^3$, $Y^1$, $Y^2$, and X are as defined in Formula XIII.

Cyanidation of the 11α-hydroxyl substrate of Formula VIII may be carried out by reacting it with a cyanide ion source such as a ketone cyanohydrin, most preferably acetone cyanohydrin, in the presence of a base and a alkali metal salt, most preferably LiCl. Alternatively, cyanidation can be effected without a cyanohydrin by using an alkali metal cyanide in the presence of an acid.

In the ketone cyanohydrin process, the reaction is conducted in solution, preferably using an aprotic polar solvent such as dimethylformamide or dimethyl sulfoxide. Formation of the enamine requires at least two moles of cyanide ion source per mole of substrate, and preferably a slight excess of the cyanide source is used. The base is preferably a nitrogenous base such as a dialkylamine, trialkylamine, alkanolamine, pyridine or the like. However, inorganic bases such as alkali metal carbonates or alkali metal hydroxides can also be used. Preferably, the substrate of Formula VIII is initially present in a proportion of between about 20 and about 50% by weight and the base is present in a proportion of between 0.5 to two equivalents per equivalent of substrate. The temperature of the reaction is not critical, but productivity is enhanced by operation at elevated temperature. Thus, for example, where triethylamine is used as the base, the reaction is advantageously conducted in the range of about 80° C. to about 90° C. At such temperatures, the reaction proceeds to completion in about 5 to about 20 hours. When diisopropylethyl amine is used as the base and the reaction is conducted at 105° C., the reaction is completed at 8 hours. At the end of the reaction period, the solvent is removed under vacuum and the residual oil dissolved in water and neutralized to pH 7 with dilute acid, preferably hydrochloric. The product precipitates from this solution, and is thereafter washed with distilled water and air dried. Liberated HCN may be stripped with an inert gas and quenched in an alkaline solution. The dried precipitate is taken up in chloroform or other suitable solvent, then extracted with concentrated acid, e.g., 6N HCl. The extract is neutralized to pH 7 by addition of an inorganic base, preferably an alkali metal hydroxide, and cooled to a temperature in the range of 0° C. The resulting precipitate is washed and dried, then recrystallized from a suitable solvent, e.g., acetone, to produce a product of Formula VII suitable for use in the next step of the process.

Alternatively, the reaction may be conducted in a aqueous solvent system comprising water-miscible organic solvent such as methanol or in a biphasic system comprising water and an organic solvent such as ethyl acetate. In this alternative, product may be recovered by diluting the reaction solution with water, and thereafter extracting the product using an organic solvent such as methylene chloride or chloroform, and then back extracting from the organic extract using concentrated mineral acid, e.g., 2N HCl. See U.S. Pat. No. 3,200,113.

According to a still further alternative, the reaction may be conducted in a water-miscible solvent such as dimethylformamide, dimethylacetamide, N-methyl, pyrolidone or dimethyl sulfoxide, after which the reaction product solution is diluted with water and rendered alkaline, e.g., by addition of an alkali metal carbonate, then cooled to 0° to 10° C., thereby causing the product to precipitate. Preferably, the system is quenched with an alkali metal hypohalite or other reagent effective to prevent evolution of cyanide. After filtration and washing with water, the precipitated product is suitable for use in the next step of the process.

According to a still further alternative, the enamine product of Formula VII may be produced by reaction of a substrate of Formula VIII in the presence of a proton source, with an excess of alkali metal cyanide, preferably NaCN, in an aqueous solvent comprising an aprotic water-miscible polar solvent such as dimethylformamide or dimethylacetamide. The proton source is preferably a mineral acid or $C_1$ to $C_5$ carboxylic acid, sulfuric acid being particularly preferred. Anomalously, no discrete proton source need be added where the cyanidation reagent is commercial LiCN in DMF.

Cyanide ion is preferably charged to the reactor in a proportion of between about 2.05 and about 5 molar equivalents per equivalent of substrate. The mineral acid or other proton source is believed to promote addition of HCN across the 4,5 and 6,7 double bonds, and is preferably present in a proportion of at least one mole equivalent per mole equivalent substrate; but the reaction system should remain basic by maintaining an excess of alkali metal cyanide over acid present. Reaction is preferably carried out at a temperature of at least about 75° C., typically 60° C. to 100° C., for a period of about 1 to about 8 hours, preferably about 1.5 to about 3 hours. At the end of the reaction period, the reaction mixture is cooled, preferably to about room temperature; and the product enamine is precipitated by acidifying the reaction mixture and mixing it with cold water, preferably at about ice bath temperature. Acidification is believed to close the 17-lactone, which tends to open under the basic conditions prevailing in the cyanidation. The reaction mixture is conveniently acidified using the same acid that is present during the reaction, preferably sulfuric acid. Water is preferably added in a proportion of between about 10 and about 50 mole equivalents per mole of product.

The compounds of Formula VII are novel compounds and have substantial value as intermediates for the preparation of compounds of Formula I, and especially of Formula IA. Preferably, the compounds of Formula VII correspond to Formula VIIA in which —A—A— and —B—B— are —CH$_2$—CH$_2$—, R$^3$ is hydrogen, lower alkyl or lower alkoxy, and R$^8$ and R$^9$ together constitute the 20-spiroxane ring:

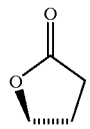

XXXIII

Most preferably the compound of Formula VII is 5'R(5'α), 7'β-20'-Aminohexadecahydro-11'β-hydroxy-10'α,13'α-dimethyl-3',5-dioxospiro[furan-2(3H),17'α(5'H)-[7,4]metheno[4H]cyclopenta[α]phenanthrene]-5'-carbonitrile.

In the next step of the Scheme 1 synthesis, the enamine of Formula VII is hydrolyzed to produce a diketone compound of Formula VI

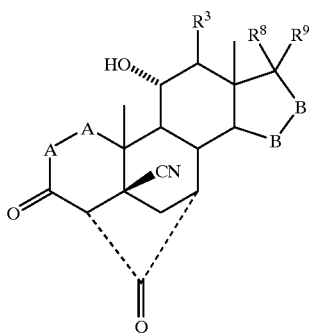

VI where —A—A—, R$^3$, —B—B—, R$^8$ and R$^9$ are as defined in Formula VIII. Any aqueous organic or mineral acid can be used for the hydrolysis. Hydrochloric acid is preferred. To enhance productivity, a water-miscible organic solvent, such as a lower alkanol, is preferably used as a cosolvent. The acid should be present in proportion of at least one equivalent per equivalent of Formula VII substrate. In an aqueous system, the enamine substrate VII can be substantially converted to the diketone of Formula VII in a period of about 5 hours at about 80° C. Operation at elevated temperature increases productivity, but temperature is not critical. Suitable temperatures are selected based on the volatility of the solvent system and acid.

Preferably, the enamine substrate of Formula VII corresponds to Formula VIIA

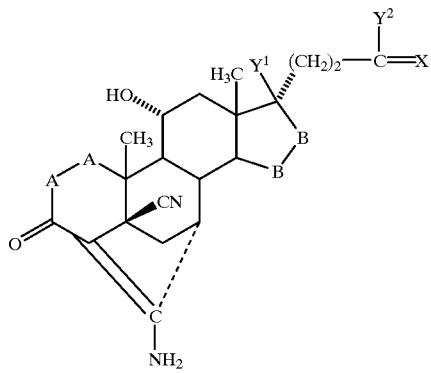

VIIA and the diketone product corresponds to Formula VIA

VIA in each of which —A—A—, —B—B—, Y$^1$, Y$^2$, and X are as defined in Formula VIIIA.

At the end of the reaction period, the solution is cooled to 0° and 25° C. to crystallize the product. The product crystals may be recrystallized from a suitable solvent such as isopropanol or methanol to produce a product of Formula VI suitable for use in the next step of the process; but recrystallization is usually not necessary. The products of Formula VI are novel compounds which have substantial value as intermediates for the preparation of compounds of Formula I, and especially of Formula IA. Preferably, the compounds of Formula VI correspond to Formula VIA in which —A—A— and —B—B— are —CH$_2$—CH$_2$—, R$^3$ is hydrogen, lower alkyl or lower alkoxy, and R$^8$ and R$^9$ together constitute the 20-spiroxane ring:

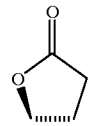

XXXIII

Most preferably, the compound of Formula VI is 4'S(4'α), 7'α-Hexadecahydro-11'α-hydroxy-10'β,13'β-dimethyl-3',5,20'-trioxospiro[furan-2(3H),17'β-[4,7]methano[17H]cyclopenta[α]phenanthrene]-5'β(2'H)-carbonitrile.

In a particularly preferred embodiment of the invention, the product enamine of Formula VII is produced from the compound of Formula VIII in the manner described above, and converted in situ to the diketone of Formula VI. In this embodiment of the invention, a formula VIII substrate is reacted with an excess of alkali metal cyanide in an aqueous solvent containing a proton source, or optionally an excess of ketone cyanohydrin in the presence of a base and LiCl, as described hereinabove. However, instead of cooling the reaction mixture, acidifying, and adding water in proportions calculated to cause precipitation of the enamine, substantial cooling of the reaction mixture is preferably avoided. Water and an acid, preferably a mineral acid such as sulfuric, are indeed added to mixture at the end of the cyanidation reaction, and the proportion of acid added is sufficient to neutralize excess alkali metal cyanide, which ordinarily requires introduction of at least one molar equivalent acid per mole of Formula VIII substrate, preferably between about 2 and about 5 mole equivalents per equivalent substrate. However, the temperature is maintained at high enough, and the dilution greater enough, so that substantial precipitation is avoided and hydrolysis of the enamine to the diketone is allowed to proceed in the liquid phase. Thus, the process proceeds with minimum interruption and high productivity. Hydrolysis is preferably conducted at a temperature of at least 80° C., more preferably in the range of about 90° C. to about 100° C., for a period of typically about 1 to about 10 hours, more preferably about 2 to about 5 hours. Then the reaction mixture is cooled, preferably to a temperature of between about 0° C. and about 15° C., advantageously in an ice bath to about 5° C. to about 10° C., for precipitation of the product diketone of Formula VI. The solid product may be recovered, as by filtration, and impurities removed by washing with water.

In the next step of the Scheme 1 synthesis, the diketone compound of Formula VI is reacted with a metal alkoxide to open up the ketone bridge between the 4 and 7 positions, cleave the bond between the carbonyl group and the 4-carbon, and form an α-oriented alkanoyloxycarbonyl substituent at the 7 position and eliminating cyanide at the 5-carbon. The product of this reaction is a hydroxyester compound corresponding to Formula V

V

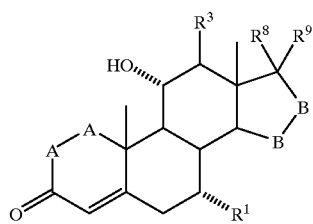

where —A—A—, $R^3$, —B—B—, $R^8$ and $R^9$ are as defined in Formula VIII, and $R^1$ is lower alkoxycarbonyl or hydroxycarbonyl. The metal alkoxide used in the reaction corresponds to the formula $R^{10}OM$ where M is alkali metal and $R^{10}$ corresponds to the alkoxy substituent of $R^1$. Yields of this reaction are most satisfactory when the metal alkoxide is K or Na methoxide, but other lower alkoxides can be used. A K alkoxide is particularly preferred. Phenoxides, other aryloxides may also be used, as well as arylsulfides. The reaction is conveniently carried out in the presence of an alcohol corresponding to the formula $R^{10}OH$ where $R^{10}$ is as defined above. Other conventional solvents may be used. Preferably, the Formula VI substrate is present in a proportion of between about 2% and about 12% by weight, more preferably at least about 6% by weight and $R^{10}OM$ is present in a proportion of between about 0.5 and about 4 moles per mole of substrate. Temperature is not critical but elevated temperature enhances productivity. Reaction time is typically between about 4 and about 24 hours, preferably about 4 to 16 hours. Conveniently, the reaction is carried out at atmospheric reflux temperature depending on the solvent used.

In the conversion of the diketone of Formula VI to the hydroxyester of Formula VI, by-product cyanide ion can react with the product to form 5-cyanoester. Because the equilibrium is more favorable at low concentrations, the reaction is preferably run at rather high dilution, e.g., as high as 40:1 for reaction with Na methoxide. It has been found that significantly higher productivity can be realized by use of K methoxide rather than Na methoxide, because a dilution in the range of about 20:1 is generally sufficient to minimize the extent of reverse cyanidation where K methoxide is the reagent.

In accordance with the invention, it has been further discovered that the reverse cyanidation reaction may be inhibited by taking appropriate chemical or physical measures to remove by-product cyanide ion from the reaction zone. Thus, in a further embodiment of the invention, the reaction of the diketone with alkali metal alkoxide may be carried out in the presence of an precipitating agent for cyanide ion such as, for example, a salt comprising a cation which forms an insoluble cyanide compound. Such salts may, for example, include zinc iodide, ferric sulfate, or essentially any halide, sulfate or other salt of an alkaline earth or transition metal that is more soluble than the corresponding cyanide. If zinc iodide is present in proportions in the range of about one equivalent per equivalent diketone substrate, it has been observed that the productivity of the reaction is increased substantially as compared to the process as conducted in the absence of an alkali metal halide.

Even where a precipitating agent is used for removal of cyanide ion, it remains preferable to run at fairly high dilution, but by use of a precipitating agent the solvent to diketone substrate molar ratio may be reduced significantly compared to reactions in the absence of such agent. Recovery of the hydroxyester of Formula V can be carried out according to either the extractive or non-extractive procedures described below.

Preferably, the diketone substrate of Formula VI corresponds to Formula VIA

VIA

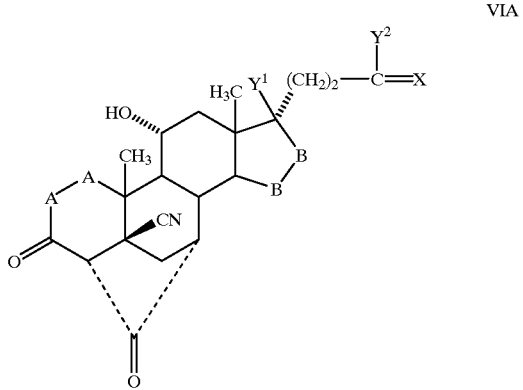

and the hydroxyester product corresponds to Formula VA

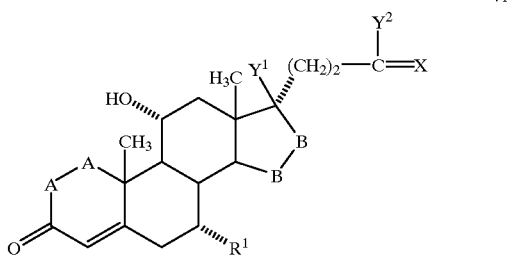

VA in each of which —A—A—, —B—B—, $Y^1$, $Y^2$, and X are as defined in Formula XIII and $R_1$ is as defined in Formula V.

The products of Formula V are novel compounds which have substantial value as intermediates for the preparation of compounds of Formula I, and especially of Formula IA. Preferably, the compounds of Formula V correspond to Formula VA in which —A—A— and —B—B— are —$CH_2$—$CH_2$—, $R^3$ is hydrogen, lower alkyl or lower alkoxy, and $R^8$ and $R^9$ together constitute the 20-spiroxane ring:

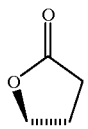

XXXIII

Most preferably, the compound of Formula V is Methyl Hydrogen 11α,17α-Dihydroxy-3-oxopregn-4-ene-7α,21-dicarboxylate, γ-Lactone.

The compound of Formula V may be isolated by acidifying the reaction solution, e.g., with concentrated HCl, cooling to ambient temperature, and extracting the product with an organic solvent such as methylene chloride or ethyl acetate. The extract is washed with an aqueous alkaline wash solution, dried and filtered, after which the solvent is removed. Alternatively, the reaction solution containing the product of Formula V may be quenched with concentrated acid. The product solution is concentrated, cooled to 0° to 25° C. and the product solid is isolated by filtration.

According to a preferred mode of recovery of the product of Formula V, methanol and HCN are removed by distillation after the conclusion of the reaction period, with water and acid being added before or during the distillation. Addition of water before the distillation simplifies operations, but progressive addition during the distillation allows the volume in the still to be maintained substantially constant. Product of Formula V crystallizes from the still bottoms as the distillation proceeds. This mode of recovery provides a high quality crystalline product without extraction operations.

In accordance with a further alternative, the reaction solution containing the product of Formula V may be quenched with mineral acid, e.g., 4N HCl, after which the solvent is removed by distillation. Removal of the solvent is also effective for removing residual HCN from the reaction product. It has been found that multiple solvent extractions for purification of the compound of Formula V are not necessary where the compound of Formula V serves as an intermediate in a process for the preparation of epoxymexrenone, as described herein. In fact, such extractions can often be entirely eliminated. Where solvent extraction is used for product purification, it is desirable to supplement the solvent washes with brine and caustic washes. But where the solvent extractions are eliminated, the brine and caustic washes are too. Eliminating the extractions and washes significantly enhances the productivity of the process, without sacrificing yield or product quality, and also eliminates the need for drying of the washed solution with a dessicant such as sodium sulfate. The crude 11α-hydroxy-7α-alkanoyloxycarbonyl product is taken up again in the solvent for the next reaction step of the process, which is the conversion of the 11-hydroxy group to a good leaving group at the 11 position thereby producing a compound of Formula IV:

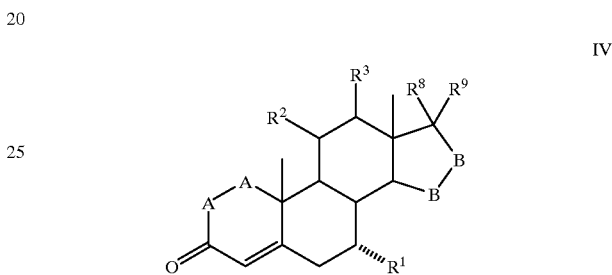

IV where —A—A—, $R^3$, —B—B—, $R_8$ and $R^9$ are as defined in Formula VIII, $R^1$ is as defined in Formula V, and $R^2$ is lower arylsulfonyloxy, alkylsulfonyloxy, acyloxy or halide. Preferably, the 11α-hydroxyl is esterified by reaction with a lower alkylsulfonyl halide, an acyl halide or an acid anhydride which is added to the solution containing the intermediate product of Formula V. Lower alkylsulfonyl halides, and especially methanesulfonyl chloride, are preferred. Alternatively, the 11-α hydroxy group could be converted to a halide by reaction of a suitable reagent such as thionyl bromide, thionyl chloride, sulfuryl chloride or oxalyl chloride. Other reagents for forming 11a-sulfonic acid esters include tosyl chloride, benzenesulfonyl chloride and trifluoromethanesulfonic anhydride. The reaction is conducted in a solvent containing a hydrogen halide scavenger such as triethylamine or pyridine. Inorganic bases such as K or Na carbonate can also be used. The initial concentration of the hydroxyester of Formula V is preferably between about 5% and about 50% by weight. The esterification reagent is preferably present in slight excess. Methylene chloride is a particularly suitable solvent for the reaction, but other solvents such as dichloroethane, pyridine, chloroform, methyl ethyl ketone, dimethoxyethane, methyl isobutyl ketone, acetone, other ketones, ethers, acetonitrile, toluene, and tetrahydrofuran can also be employed. The reaction temperature is governed primarily by the volatility of the solvent. In methylene chloride, the reaction temperature is preferably in the range of between about –10° C. and about 10° C.

Preferably, the hydroxyester substrate of Formula V corresponds to Formula VA

VA

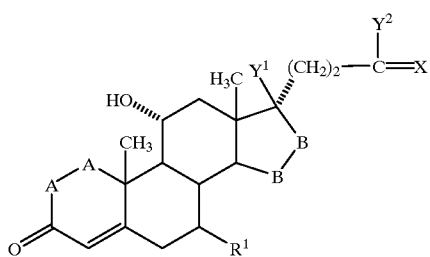

and the product corresponds to Formula IVA

IVA

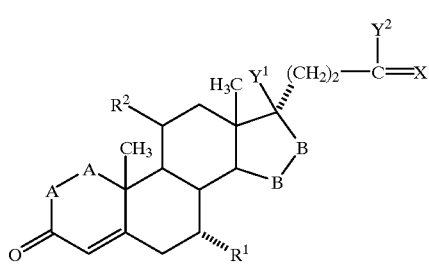

in each of which —A—A—, —B—B—, $Y^1$, $Y^2$, and X are as defined in Formula XIII, $R^1$ is lower alkanoyloxycarbonyl or hydroxycarbonyl, and $R^2$ is as defined in Formula IV.

The products of Formula IV are novel compounds which have substantial value as intermediates for the preparation of compounds of Formula I, and especially of Formula IA. Preferably, the compounds of Formula IV correspond to Formula VA in which —A—A— and —B—B— are —CH$_2$—CH$_2$—, $R^3$ is hydrogen, lower alkyl or lower alkoxy, and $R^8$ and $R^9$ together constitute the 20-spiroxane ring:

XXXIII

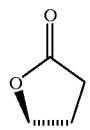

Most preferably, the compound of Formula IV is Methyl Hydrogen 17α-Hydroxy-11α-(methylsulfonyl)oxy-3-oxopregn-4-ene-7α,21-dicarboxylate, γ-Lactone.

If desired, the compound of Formula IV may be isolated by removal of the solvent. Preferably, the reaction solution is first washed with an aqueous alkaline wash solution, e.g., 0.5–2N NaoH, followed by an acid wash, e.g., 0.5–2N HCl. After removal of the reaction solvent, the product is recrystallized, e.g., by taking the product up in methylene chloride and then adding another solvent such as ethyl ether which lowers the solubility of the product of Formula IV, causing it to precipitate in crystalline form.

In the recovery of the product of Formula IV, or in preparation of the reaction solution for conversion of the Formula IV intermediate to the intermediate of Formula II as is further described hereinbelow, all extractions and/or washing steps may be dispensed with if the solution is instead treated with ion exchange resins for removal of acidic and basic impurities. The solution is treated first with an anion exchange resin, then with a cation exchange resin. Alternatively, the reaction solution may first be treated with inorganic adsorbents such as basic alumina or basic silica, followed by a dilute acid wash. Basic silica or basic alumina may typically be mixed with the reaction solution in a proportion of between about 5 and about 50 g per kg of product, preferably between about 15 and about 20 g per kg product. Whether ion exchange resins or inorganic adsorbents are used, the treatment can be carried out by simply slurrying the resin or inorganic adsorbent with the reaction solution under agitation at ambient temperature, then removing the resin or inorganic adsorbent by filtration.

In an alternative and preferred embodiment of the invention, the product compound of Formula IV is recovered in crude form as a concentrated solution by removal of a portion of the solvent. This concentrated solution is used directly in the following step of the process, which is removal of the 11α-leaving group from the compound of Formula IV, thereby producing an enester of Formula II:

II

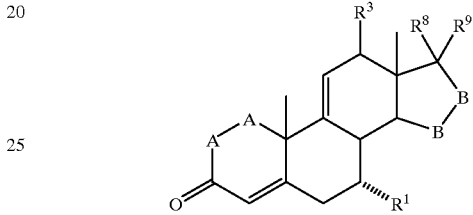

where —A—A—, $R^3$, —B—B—, $R^8$ and $R^9$ are as defined in Formula VIII, and $R^1$ is as defined in Formula V. For purposes of this reaction, the $R^2$ substituent of the compound of Formula IV may be any leaving group the abstraction of which is effective for generating a double bond between the 9- and 11-carbons. Preferably, the leaving group is a lower alkylsulfonyloxy or acyloxy substituent which is removed by reaction with an acid and an alkali metal salt. Mineral acids can be used, but lower alkanoic acids are preferred. Advantageously, the reagent for the reaction further includes an alkali metal salt of the alkanoic acid utilized. It is particularly preferred that the leaving group comprise mesyloxy and the reagent for the reaction comprise formic acid or acetic acid and an alkali metal salt of one of these acids or another lower alkanoic acid. Where the leaving group is mesyloxy and the removal reagent is formic acid and potassium formate a relatively high ratio of 9,11 to 11,12-olefin is observed. If free water is present during removal of the leaving group, impurities tend to be formed, particularly a 7,9-lactone

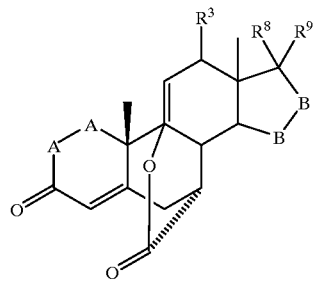

which is difficult to remove from the final product. Hence, acetic anhydride or other drying agent is used to remove the water present in formic acid. The free water content of the reaction mixture before reaction should be maintained at a level below about 0.5%, preferably below about 0.1% by weight, as measured by Karl Fischer analysis for water, based on total reaction solution. Although it is preferred that the reaction mixture be kept as dry as practicable, satisfactory results have been realized with 0.3% by weight water. Preferably, the reaction charge mixture contains between about 4% and about 50% by weight of the substrate of Formula IV in the alkanoic acid. Between about 4% and about 20% by weight of the alkali metal salt of the acid is preferably included. Where acetic anhydride is used as the drying agent, it is preferably present in a proportion of between about 0.05 moles and about 0.2 moles per mole of alkanoic acid.

It has been found that proportions of by-product 7,9-lactone and 11,12-olefin in the reaction mixture is relatively low where the elimination reagent comprises a combination of trifluoroacetic acid, trifluoroacetic anhydride and potassium acetate as the reagent for elimination of the leaving group and formation of the enester (9,11-olefin). Trifluoroacetic anhydride serves as the drying agent, and should be present in a proportion of at least about 3% by weight, more preferably at least about 15% by weight, most preferably about 20% by weight, based on the trifluoroacetic acid eliminating reagent.

Alternatively, the 11α-leaving groups from the compound of Formula IV, may be eliminated to produce an enester of Formula II by heating a solution of Formula IV in an organic solvent such as DMSO, DMF or DMA.

Further in accordance with the invention, the compound of Formula IV is reacted initially with an alkenyl alkanoate such as isopropenyl acetate in the presence of an acid such as toluene sulfonic acid or an anhydrous mineral acid such as sulfuric acid to form the 3-enol ester:

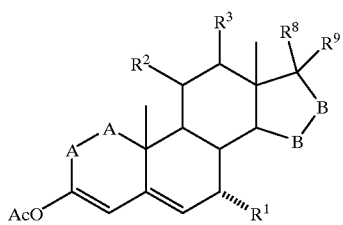

IV (Z)

of the compound of Formula IV. Alternatively, the 3 enol ester can be formed by treatment with an acid anhydrides and base such as acetic acid and sodium acetate. Further alternatives include treatment with ketene in the presence of an acid to produce IV(Z). The intermediate of Formula IV(Z) is thereafter reacted with an alkali metal formate or acetate in the presence of formic or acetic acid to produce the Δ-9,11 enol acetate of Formula IV(Y):

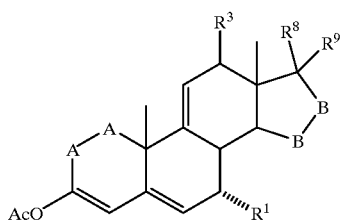

IV (Y)

which can then be converted to the enester of Formula II in an organic solvent, preferably an alcohol such as methanol, by either thermal decomposition of the enol acetate or reaction thereof with an alkali metal alkoxide. The elimination reaction is highly selective to the enester of Formula II in preference to the 11,12-olefin and 7,9-lactone, and this selectivity is preserved through conversion of the enol acetate to the enone.

Preferably, the substrate of Formula IV corresponds to Formula IVA

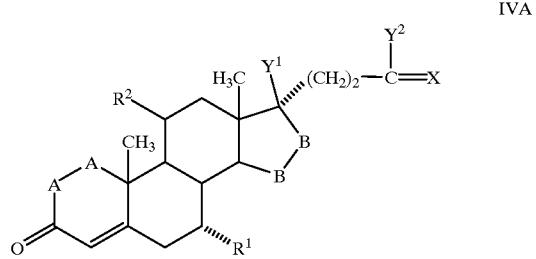

IVA and the enester product corresponds to Formula IIA

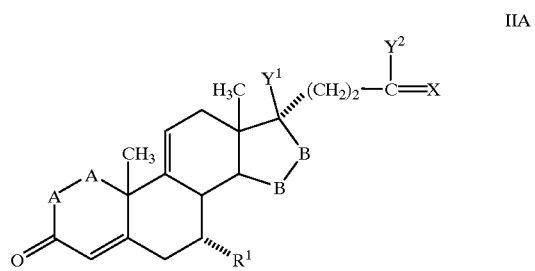

IIA in each of which —A—A—, —B—B—, $Y^1$, $Y^2$, and X are as defined in Formola XIII and $R^1$ is as defined in Formula V.

If desired, the compound of Formla II may be isolated by removing the solvent, taking up the solid product in cold water, and extracting with an organic solvent, such as ethyl acetate. After appropriate washing and drying steps, the product is recovered by removing the extraction solvent. The enester is then dissolved in a solvent appropriate for the conversion to the product of Formula I. Alternatively, the enester can be isolated by adding water to the concentrated product solution and filtering the solid product, thereby preferentially removing the 7,9-lactone. Conversion of the substrate of Formula II to the product of Formula IA may be conducted in the manner described in U.S. Pat. No. 4,559,332 which is expressly incorporated herein by reference, or more preferably by the novel reaction using a haloacetamide promoter as described below.

In another embodiment of the invention, the hydroxyester of Formula V may be converted to the enester of Formula II without isolation of the intermediate compound of Formula IV. In this method, the hydroxyester is taken up in a an organic solvent, such as methylene chloride; and either an acylating agent, e.g., methanesulfonyl chloride, or halogenating reagent, e.g., sulfuryl chloride, is added to the solution. The mixture is agitated and, where halogenation is involved, an HCl scavenger such as imidazole is added. Mixing of base with the solution is highly exothermic, and should therefore be conducted at a controlled rate with full cooling. After the base addition, the resulting mixture is warmed to moderate temperature, e.g., 0° C. to room temperature or slightly above, and reacted for a period of typically 1 to 4 hours. After reaction is complete, the solvent is stripped, preferably under high vacuum (e.g., 24" to 28" Hg) conditions at −10° to +15° C., more preferably about 0° to about 5° C., to concentrate the solution and remove excess base. The substrate is then redissolved in an organic solvent, preferably a halogenated solvent such as methylene chloride for conversion to the enester.

The leaving group elimination reagent is preferably prepared by mixing an organic acid, an organic acid salt and a drying agent, preferably formic acid, alkali metal formate and acetic anhydride, respectively, in a dry reactor. Addition of acetic anhydride is exothermic and results in release of CO, so the addition rate must be controlled accordingly. To promote the removal of water, the temperature of this reaction is preferably maintained in the range of 60° to 90° C., most preferably about 65° to about 75° C. This reagent is then added to the product solution of the compound of Formula IV to effect the elimination reaction. After 4–8 hours, the reaction mixture is preferably heated to a temperature of at least about 85° C., but not above about 95° C. until all volatile distillate has been removed, and then for an additional period to complete the reaction, typically about 1 to 4 hours. The reaction mixture is cooled, and after recovery by standard extraction techniques, the enester may be recovered as desired by evaporating the solvent.

It has further been found that the enester of Formula II may be recovered from the reaction solution by an alternative procedure which avoids the need for extraction steps following the elimination reaction, thereby providing savings in cost, improvement in yield and/or improvement in productivity. In this process, the enester product is precipitated by dilution of the reaction mixture with water after removal of formic acid. The product is then isolated by filtration. No extractions are required.

According to a further alternative for conversion of the hydroxyester of Formula V to the enester of Formula II without isolation of the compound of Formula IV, the 11α-hydroxy group of the Formula V hydroxyester is replaced by halogen, and the Formula II enester is then formed in situ by thermal dehydro halogenation. Replacement of the hydroxy group by halogen is effected by reaction with sulfuryl halide, preferably sulfuryl chloride, in the cold in the presence of a hydrogen halide scavenger such as imidazole. The hydroxyester is dissolved in a solvent such as tetrahydrofuran and cooled to 0° C. to −70° C. The sulfuryl halide is added and the reaction mixture is warmed to moderate temperature, e.g., room temperature, for a time sufficient to complete the elimination reaction, typically 1 to 4 hours. The process of this embodiment not only combines two steps into one, but eliminates the use of: a halogenated reaction solvent; an acid (such as acetic); and a drying reagent (acetic anhydride or sodium sulfate). Moreover, the reaction does not require refluxing conditions, and avoids the generation of by-product CO which results when acetic acid is used as a drying reagent.

In accordance with a particularly preferred embodiment of the invention, the diketone compound of Formula VI can be converted to epoxymexrenone or other compound of Formula I without isolating any intermediate in purified form. In accordance with this preferred process, the reaction solution containing the hydroxyester is quenched with a strong acid solution, cooled to ambient temperature and then extracted with an appropriate extraction solvent. Advantageously, an aqueous solution of inorganic salt, e.g., 10% by weight saline solution, is added to the reaction mixture prior to the extraction. The extract is washed and dried by azeotropic distillation for removal of the methanol solvent remaining from the ketone cleavage reaction.

The resulting concentrated solution containing between about 5% and about 50% by weight compound of Formula V is then contacted in the cold with an acylating or alkylsulfonylating reagent to form the sulfonic ester or dicarboxylic acid ester. After the alkylsulfonation or carboxylation reaction is complete the reaction solution is passed over an acidic and then a basic exchange resin column for the removal of basic and acidic impurities. After each pass, the column is washed with an appropriate solvent, e.g., methylene chloride, for the recovery of residual sulfonic or dicarboxylic ester therefrom. The combined eluate and wash fractions are combined and reduced, preferably under vacuum, to produce a concentrated solution containing the sulfonic ester or dicarboxylic ester of Formula IV. This concentrated solution is then contacted with a dry reagent comprising an agent effect for removal of the 11α-ester leaving group and abstraction of hydrogen to form a 9,11 double bond. Preferably, the reagent for removal of the leaving group comprises the formic acid/alkali metal formate/acetic anhydride dry reagent solution described above. After reaction is complete, the reaction mixture is cooled and formic acid and/or other volatile components are removed under vacuum. The residue is cooled to ambient temperature, subjected to appropriate washing steps, and then dried to give a concentrated solution containing the enester of Formula II. This enester may then be converted to epoxymexrenone or other compound of Formula I using the method described herein, or in U.S. Pat. No. 4,559,332.

In an especially preferred embodiment of the invention, the solvent is removed from the reaction solution under vacuum, and the product of Formula IV is partitioned between water and an appropriate organic solvent, e.g., ethyl acetate. The aqueous layer is then back extracted with the organic solvent, and the back extract washed with an alkaline solution, preferably a solution of an alkali metal hydroxide containing an alkali metal halide. The organic phase is concentrated, preferably under vacuum, to yield the enester product of Formula II. The product of Formula II may then be taken up in an organic solvent, e.g., methylene chloride, and further reacted in the manner described in the '332 patent to produce the product of Formula I.

Where trihaloacetonitrile is used in the epoxidation reaction, it has been found that the selection of solvent is important, with halogenated solvents being highly preferred, and methylene chloride being especially preferred. Solvents such as dichloroethane and chlorobenzene give reasonably satisfactory yields, but yields are generally better in a methylene chloride reaction medium. Solvents such as acetonitrile and ethyl acetate generally give poor yields, while reaction in solvents such as methanol or water/tetrahydrofuran give little of the desired product.

Further in accordance with the present invention, it has been discovered that numerous improvements in the synthesis of epoxymexrenone can be realized by use of a trihaloacetamide rather than a trihaloacetonitrile as a peroxide activator for the epoxidation reaction. In accordance with a particularly preferred process, the epoxidation is carried out by reaction of the substrate of Formula IIA with hydrogen peroxide in the presence of trichloroacetamide and an appropriate buffer. Preferably, the reaction is conducted in a pH in the range of about 3 to about 7, most preferably between about 5 and about 7. However, despite these considerations, successful reaction has been realized outside the preferred pH ranges.

Especially favorable results are obtained with a buffer comprising dipotassium hydrogen phosphate, and/or with a buffer comprising a combination of dipotassium hydrogenphosphate and potassium dihydrogen phosphate in relative proportions of between about 1:4 and about 2:1, most preferably in the range of about 2:3. Borate buffers can also be used, but generally give slower conversions than dipotassium phosphate or K$_2$HPO$_4$ or K$_2$HPO$_4$/KH$_2$PO$_4$ mixtures. Whatever the makeup of the buffer, it should provide a pH in the range indicated above. Aside from the overall composition of the buffer or the precise pH it may impart, it has been observed that the reaction proceeds much more effectively if at least a portion of the buffer is comprised of dibasic hydrogenphosphate ion. It is believed that this ion may participate essentially as a homogeneous catalyst in the formation of an adduct or complex comprising the promoter and hydroperoxide ion, the generation of which may in turn be essential to the overall epoxidation reaction mechanism. Thus, the quantitative requirement for dibasic hydrogenphosphate (preferably from K$_2$HPO$_4$) may be only a small catalytic concentration. Generally, it is preferred that HPO$_4$ be present in a proportion of at least about 0.1 equivalents, e.g., between about 0.1 and about 0.3 equivalents, per equivalent substrate.

The reaction is carried out in a suitable solvent, preferably methylene chloride, but alternatively other halogenated solvents such as chlorobenzene or dichloroethane can be used. Toluene and mixtures of toluene and acetonitrile have also been found satisfactory. Without committing to a particular theory, it is posited that the reaction proceeds most effectively in a two phase system in which a hydroperoxide intermediate is formed and distributes to the organic phase of low water content, and reacts with the substrate in the organic phase. Thus the preferred solvents are those in which water solubility is low. Effective recovery from toluene is promoted by inclusion of another solvent such as acetonitrile.

In the conversion of substrates of Formula II to products of Formula I, toluene provides a process advantage since the substrates are freely soluble in toluene and the products are not. Thus, the product precipitates during the reaction when conversions reach the 40–50% range, producing a three phase mixture from which the product can be conveniently separated by filtration. Methanol, ethyl acetate, acetonitrile alone, THF and THF/water have not proved as to be as effective as the halogenated solvents or toluene in carrying out the conversion of this step of the process.

While trichloroacetamide is a highly preferred reagent, other trihaloacetamides such as trifluoroacetamide can also be used. Trihalomethylbenzamide, and other compounds having an arylene moiety between the electron withdrawing trihalomethyl group and the carbonyl of the amide, may also be useful. 3,3,3-Trihalopropionamides may also be used, but with less favorable results. Generically, the peroxide activator may correspond to the formula:

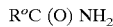
R$^o$C (O) NH$_2$ where R$^o$ is a group having an electron withdrawing strength (as measured by sigma constant) at least as high as that of the monochloromethyl group. More particularly, the peroxide activator may correspond to the formula:

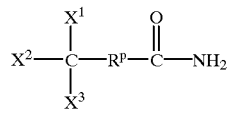

where X$^1$, X$^2$, and X$^3$ are independently selected from among halo, hydrogen, alkyl, haloalkyl and cyano and cyanoalkyl, and RP is selected from among arylene and —(CX$^4$X$^5$)$_n$—, where n is 0 or 1, at least one of X$^1$, X$^2$, X$^3$, X$^4$ and X$^5$ being halo or perhaloalkyl. Where any of X$^1$, X$^2$, X$^3$, X$^4$ or X$^5$ is not halo, it is preferably haloalkyl, most preferably perhaloalkyl. Particularly preferred activators include those in which n is 0 and at least two of X$^1$, X$^2$ and X$^3$ are halo; or in which all of X$^1$, X$^2$, X$^3$, X$^4$ and X$^5$ are halo or perhaloalkyl. Each of X$^1$, X$^2$ X$^3$, X$^4$ and X$^5$ is preferably Cl or F, most preferably Cl, though mixed halides may also be suitable, as may perchloralkyl or perbromoalkyl and combinations thereof.

Preferably, the peroxide activator is present in a proportion of at least about 1 equivalents, more preferably between about 1.5 and about 2 equivalents, per equivalent of substrate initially present. Hydrogen peroxide should be charged to the reaction in at least modest excess, or added progressively as the epoxidation reaction proceeds. Although the reaction consumes only one to two equivalents of hydrogen peroxide per mole of substrate, hydrogen peroxide is preferably charged in substantial excess relative to substrate and activator initially present. Without limiting the invention to a particular theory, it is believed that the reaction mechanism involves formation of an adduct of the activator and OOH$^-$, that the formation of this reaction is reversible with the equilibrium favoring the reverse reaction, and that a substantial initial excess of hydrogen peroxide is therefore necessary in order to drive the reaction in the forward direction. Temperature of the reaction is not narrowly critical, and may be effectively carried out within the range of 0° to 100° C. The optimum temperature depends on the selection of solvent. Generally, the preferred temperature is between about 20° C. and 30° C., but in certain solvents, e.g., toluene the reaction may be advantageously conducted in the range of 60°–70° C. At 25° C., reaction typically requires less than 10 hours, typically 3 to 6 hours. If needed additional activator and hydrogen peroxide may be added at the end of the reaction cycle to achieve complete conversion of the substrate.

At the end of the reaction cycle, the aqueous phase is removed, the organic reaction solution is preferably washed for removal of water soluble impurities, after which the product may be recovered by removal of the solvent. Before removal of solvent, the reaction solution should be washed, at with least a mild to moderately alkaline wash, e.g., sodium carbonate. Preferably, the reaction mixture is washed successively with: a mild reducing solution such as a weak (e.g. 3% by weight) solution of sodium sulfite in water; an alkaline solution, e.g., NaOH or KOH (preferably about 0.5N); an acid solution such as HCl (preferably about 1N); and a final neutral wash comprising water or brine, preferably saturated brine to minimize product losses. Prior to removal of the reaction solvent, another solvent such as an organic solvent, preferably ethanol may be advantageously added, so that the product may be recovered by crystallization after distillation for removal of the more volatile reaction solvent.

It should be understood that the novel epoxidation method utilizing trichloroacetamide or other novel peroxide activator has application well beyond the various schemes for the preparation of epoxymexrenone, and in fact may be used for the formation of epoxides across olefinic double bonds in a wide variety of substrates subject to reaction in the liquid phase. The reaction is particularly effective in unsaturated compounds in which the olefinic carbons are tetrasubstituted and trisubstituted, i.e., R$^a$R$^b$C=CR$^c$R$^d$ and R$^a$R$^b$C=CR$^c$RH where R$^a$ to R$^d$ represent substituents other than hydrogen. The reaction proceeds most rapidly and completely where the substrate is a cyclic compound with a trisubstituted double, or either a cyclic or acyclic compound with tetrasubstituted double bonds. Exemplary substrates for this reaction include Δ-9,11-canrenone, and

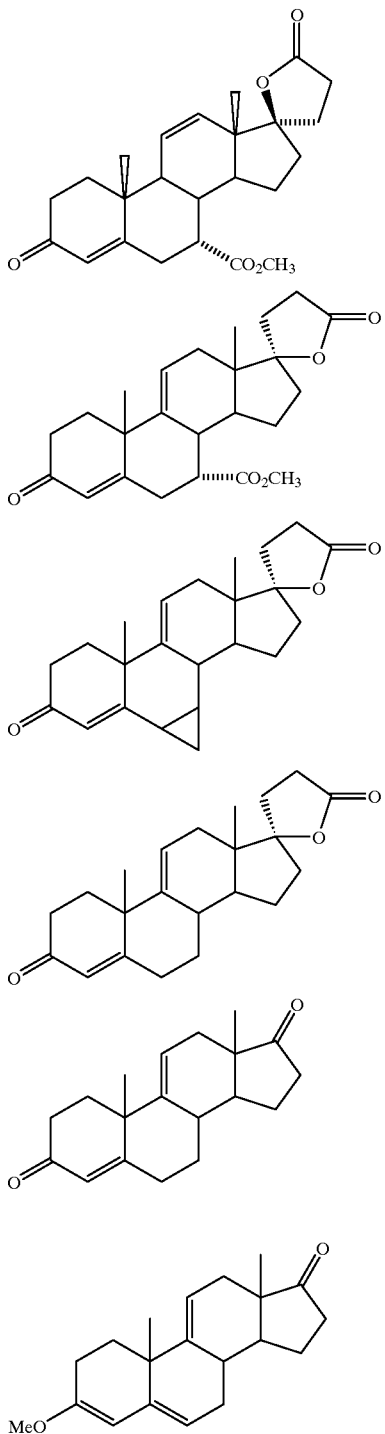

Because the reaction proceeds more rapidly and completely with trisubstituted and tetrasubstituted double bonds, it is especially effective for selective epoxidation across such double bonds in compounds that may include other double bonds where the olefinic carbons are monosubstituted, or even disubstituted.

It should be further understood that the reaction may be used to advantage in the epoxidation of monosubstituted or even disubstituted double bonds, such as the 11,12-olefin in various steroid substrates. However, because it preferentially epoxidizes the more highly substituted double bonds, e.g., the 9,11-olefin, with high selectivity, the process of this invention is especially effective for achieving high yields and productivity in the epoxidation steps of the various reaction schemes described elsewhere herein.

The improved process has been shown to be particularly advantageous application to the preparation of:

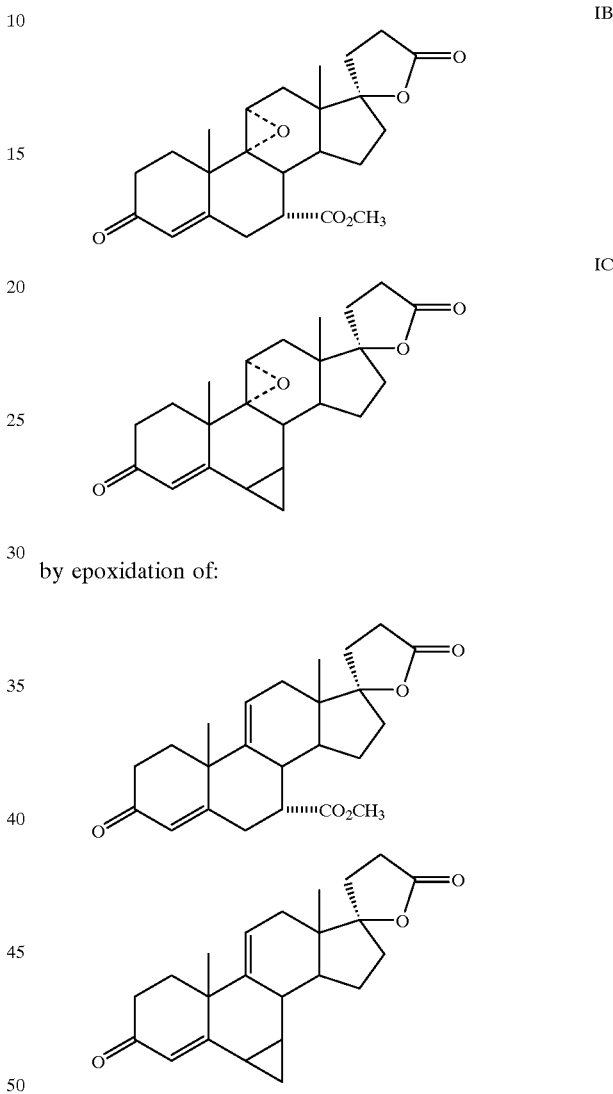

by epoxidation of:

Multiple advantages have been demonstrated for the process of the invention in which trichloroacetamide is used in place of trichloroacetonitrile as the oxygen transfer reagent for the epoxidation reaction. The trichloroacetamide reagent system provides tight regiocontrol for epoxidation across trisubstituted double with disubstituted and α,β-keto olefins in the same molecular structure. Thus, reaction yield, product profile and final purity are substantially enhanced. It has further been discovered that the substantial excess oxygen generation observed with the use of trihaloacetonitrile is not experienced with trichloroacetamide, imparting improved safety to the epoxidation process. Further in contrast to the trichloroacetonitrile promoted reaction, the trichloroacetamide reaction exhibits minimum exothermic effects, thus facilitating control of the thermal profile of the reaction. Agitation effects are observed to be minimal and reactor performance more consistent, a further advantage over the trichloroacetonitrile process. The reaction is more amenable to scaleup than the trichloroacetonitrile promoted reaction. Product isolation and purification is simple, there is no observable Bayer-Villager oxidation of carbonyl function (peroxide promoted conversion of ketone to ester) as experienced, e.g., using m-chloroperoxybenzoic acid or other peracids and the reagent is inexpensive, readily available, and easily handled.

The novel epoxidation method of the invention is highly useful as the concluding step of the synthesis of Scheme 1. In a particularly preferred embodiment, the overall process of Scheme 1 proceeds as follows:

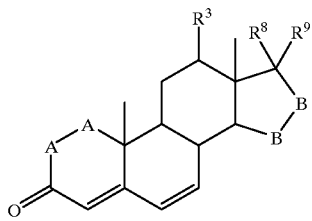

XIII

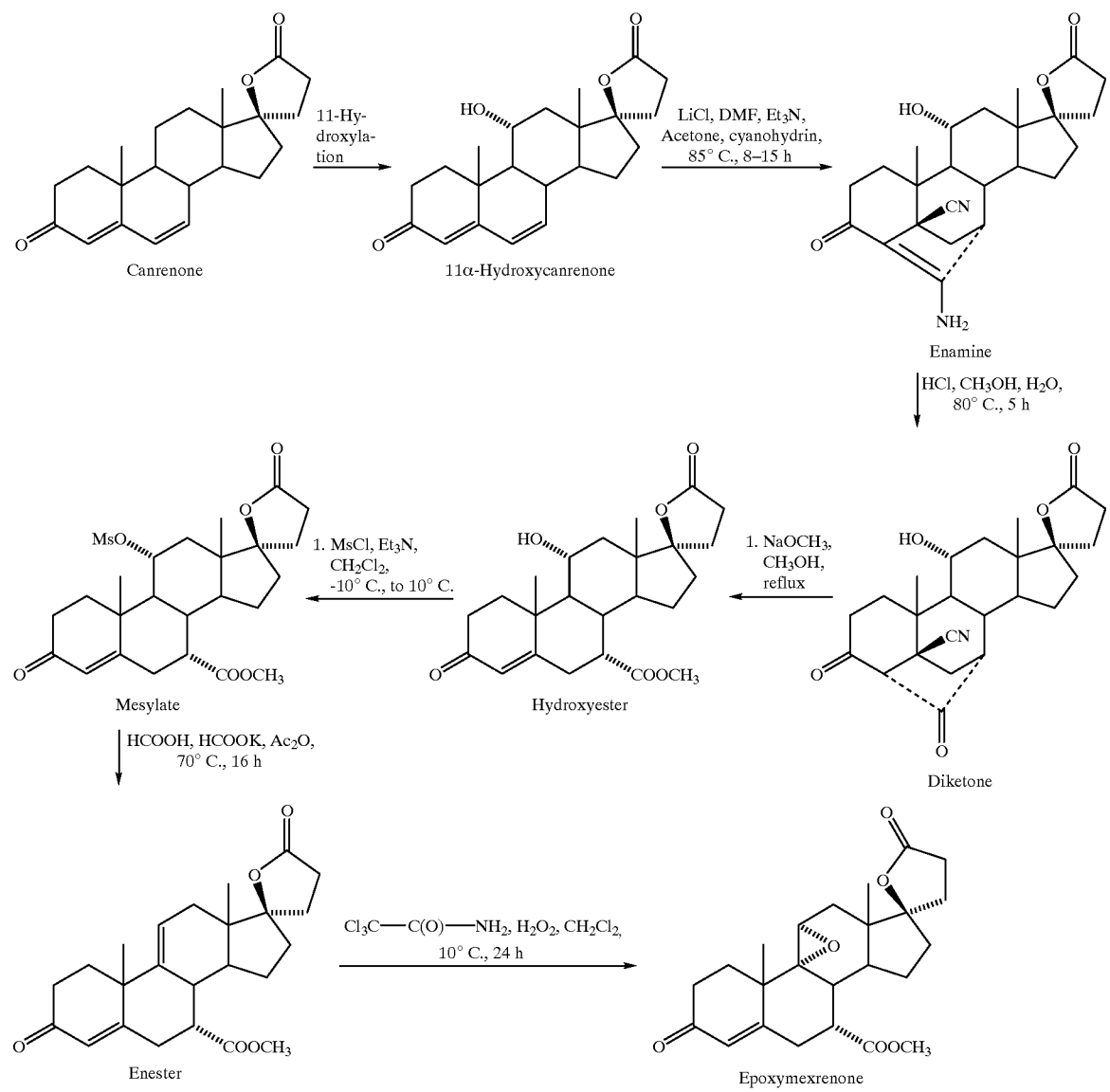

Scheme 2

The second of novel reaction schemes (Scheme 2) of this invention starts with canrenone or other substrate corresponding to Formula XIII where —A—A—, $R^3$, —B—B—, $R^8$ and $R^9$ are as defined in Formula VIII. In the first step of this process, the substrate of Formula XIII is converted to a product of Formula XII

XII

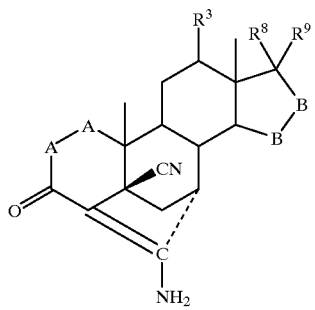

using a cyanidation reaction scheme substantially the same as that described above for conversion of the substrate of Formula VIII to the intermediate of Formula VII. Preferably, the substrate of Formula XIII corresponds to Formula XIIIA

XIIIA

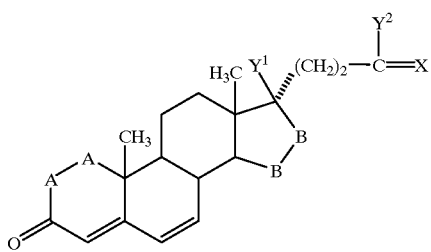

and the enamine product corresponds to Formula XIIA

XIIA

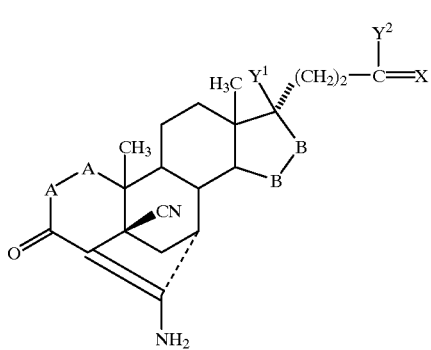

in each of which —A—A—, —B—B—, $Y^1$, $Y^2$ and X are as defined in Formula XIII.

In the second step of scheme 2, the enamine of Formula XII is hydrolyzed to an intermediate diketone product of Formula XI

XI

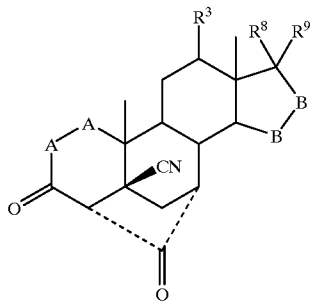

where —A—A—, $R^3$, —B—B—, $R^8$ and $R^9$ are as defined in Formula VIII, using a reaction scheme substantially the same as that described above for conversion of the substrate of Formula VIII to the intermediate of Formula VII. Preferably, the substrate of Formula XII corresponds to Formula XIIA

XIIA

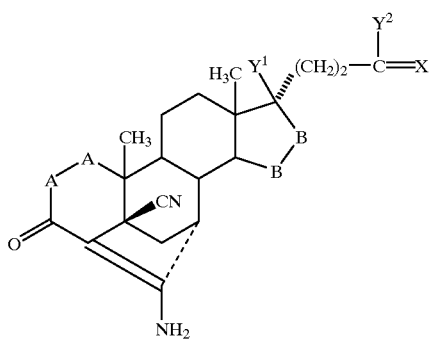

and the diketone product corresponds to Formula XIA

XIA

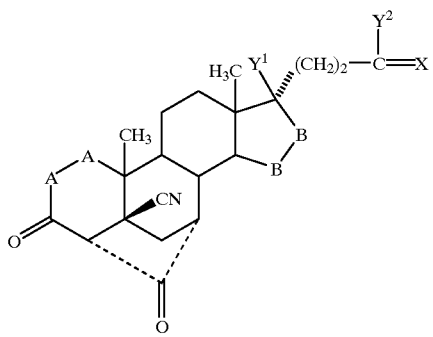

in each of which —A—A—, —B—B—, $Y^1$, $Y^2$, and X are as defined in Formula VIIIA.

Further in accordance with reaction scheme 2, the diketone of Formula XI is reacted with an alkali metal alkoxide to form mexrenone or other product corresponding to Formula X,

X

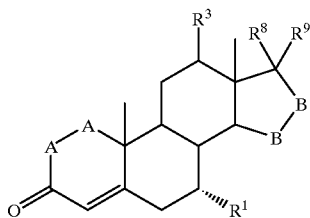

in each of which —A—A—, $R^3$, —B—B—, $R^8$ and $R^9$ are as defined in Formula VIIIA. $R^1$ is as defined in Formula V. The process is carried out using substantially the same reaction scheme that is described above for the conversion of the compounds of Formula VI to those of Formula V. Preferably, the substrate of Formula XI corresponds to Formula XIA

XIA

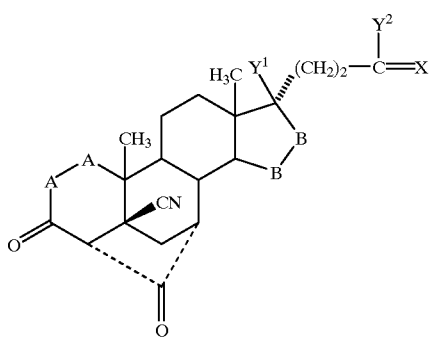

and the intermediate product corresponds to Formula XA

XA

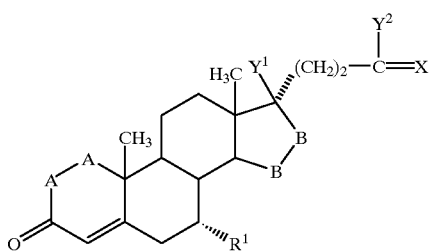

in each of which —A—A—, —B—B—, $Y^1$, $Y^2$, and X are as defined in Formula XIII. $R^1$ is as defined in Formula V.

Canrenone and other compounds of Formula X are next 9α-hydroxylated by a novel bioconversion process to yield products of Formula IX

IX

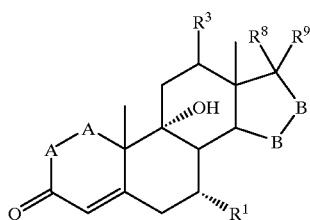

where —A—A—, $R^3$, —B—B—, $R^8$ and $R^9$ are as defined in Formula VIII, and $R^1$ is as defined in Formula V. Among the organisms that can be used in this hydroxylation step are *Nocardia conicruria* ATCC 31548, *Nocardia aurentia* ATCC 12674, *Corynespora cassiicola* ATCC 16718, *Streptomyces hydroscopicus* ATCC 27438, *Mortierella isabellina* ATCC 42613, *Beauvria bassiana* TCC 7519, *Penicillum purpurogenum* ATCC 46581, *Hypomyces chrysospermus* IMI 109891, *Thamnostylum piriforme* ATCC 8992, *Cunniqnhamella blakesleeana* ATCC 8688a, *Cunningnhamella echinulata* ATCC 3655, *Cunninghamella elegans* ATCC 9245, *Trichothecium roseum* ATCC 12543, *Epicoccum humicola* ATCC 12722, *Saccharopolyspora eythrae* ATCC 11635, *Beauvria bassiana* ATCC 13144, *Arthrobacter simplex*, *Bacterium cyclooxydans* ATCC 12673, *Cylindrocarpon radicicola* ATCC 11011, *Nocardia aurentia* ATCC 12674, *Nocardia canicruria*, *Norcardia restrictus* ATCC 14887, *Pseudomonas testosteroni* ATCC 11996, *Rhodococcus equi* ATCC 21329, *Mycobacterium fortuitum* ATCC-6842, and *Rhodococcus rhodochrous* ATCC 19150. The reaction is carried out substantially in the manner described above in connection with FIGS. 1 and 2. The process of FIG. 1 is particularly preferred.

Growth media useful in the bioconversions preferably contain between about 0.05% and about 5% by weight available nitrogen; between about 0.5% and about 5% by weight glucose; between about 0.25% and about 2.5% by weight of a yeast derivative; and between about 0.05%, and about 0.5% by weight available phosphorus. Particularly preferred growth media include the following:

soybean meal: between about 0.5% and about 3% by weight glucose; between about 0.1% and about 1% by weight soybean meal; between about 0.05% and about 0.5% by weight alkali metal halide; between about 0.05% and about 560.5% by weight of a yeast derivative such as autolyzed yeast or yeast extract; between about 0.05% and about 0.5% by weight of a phosphate salt such as $K_2HPO_4$; pH=7;

peptone-yeast extract-glucose: between about 0.2% and about 2% by weight peptone; between about 0.05% and about 0.5% by weight yeast extract; and between about 2% and about 5% by weight glucose;

Mueller-Hinton: between about 10% and about 40% by weight beef infusion; between about 0.35% and about 8.75% by weight casamino acids; between about 0.15% and about 0.7% by weight starch.

Fungi can be grown in soybean meal or peptone nutrients, while actinomycetes and eubacteria can be grown in soybean meal (plus 0.5% to 1% by weight carboxylic acid salt such as Na formate for biotransformations) or in Mueller-Hinton broth.

The production of 11β-hydroxymexrenone from mexrenone by fermentation is discussed in Example 19.

The products of Formula IX are novel compounds, which may be separated by filtration, washed with a suitable organic solvent, e.g., ethyl acetate, and recrystallized from the same or a similar solvent. They have substantial value as intermediates for the preparation of compounds of Formula I, and especially of Formula IA. Preferably, the compounds of Formula IX correspond to Formula IXA in which —A—A— and —B—B— are —$CH_2$—$CH_2$—, $R^3$ is hydrogen, lower alkyl or lower alkoxy, and $R^8$ and $R^9$ together constitute the 20-spiroxane ring:

XXXIII

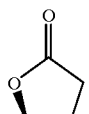

In the next step of synthesis scheme 2, the product of Formula IX is reacted with a dehydration reagent to produce a compound of Formula II

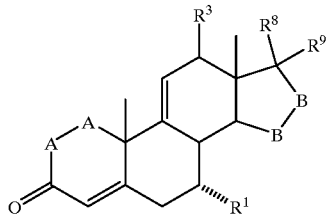

II wherein —A—A—, $R^3$, —B—B—, $R^8$ and $R^9$ are as defined in Formula VIII, and $R^1$ is as defined in Formula V. Where the substrate corresponds to Formula IXA, the product is of Formula IIA

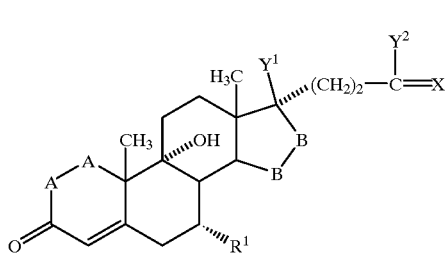

IXA

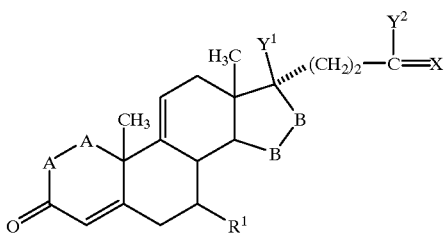

IIA in each of which —A—A—, —B—B—, $Y^1$, $Y^2$, and X are as defined in Formula XIII and $R^1$ is as defined in Formula V.

In the final step of this synthesis scheme, the product of Formula II is converted to that of Formula I by epoxidation in accordance with the method described in U.S. Pat. No. 4,559,332; or preferably by the novel epoxidation method of the invention as described hereinabove.

In a particularly preferred embodiment, the overall process of Scheme 2 proceeds as follows:

Scheme 3

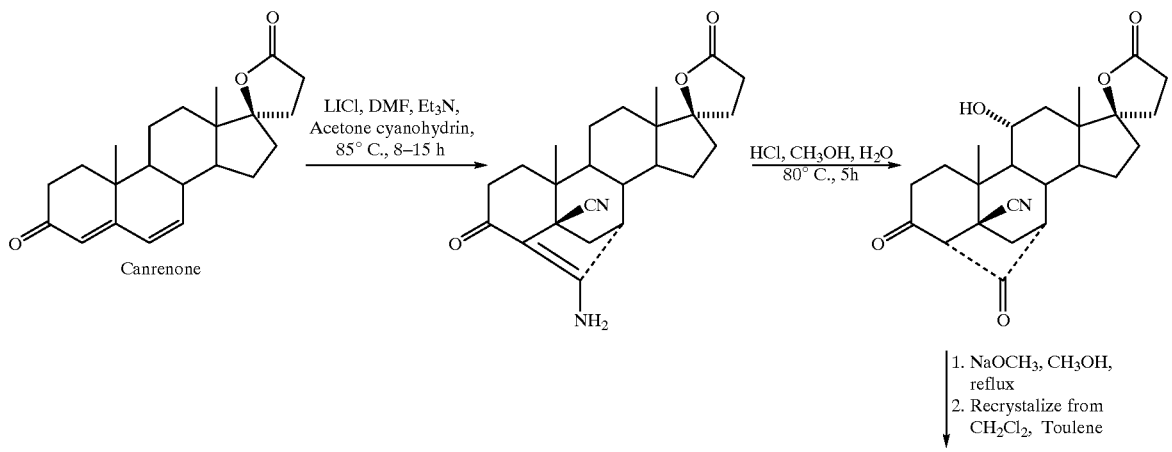

-continued

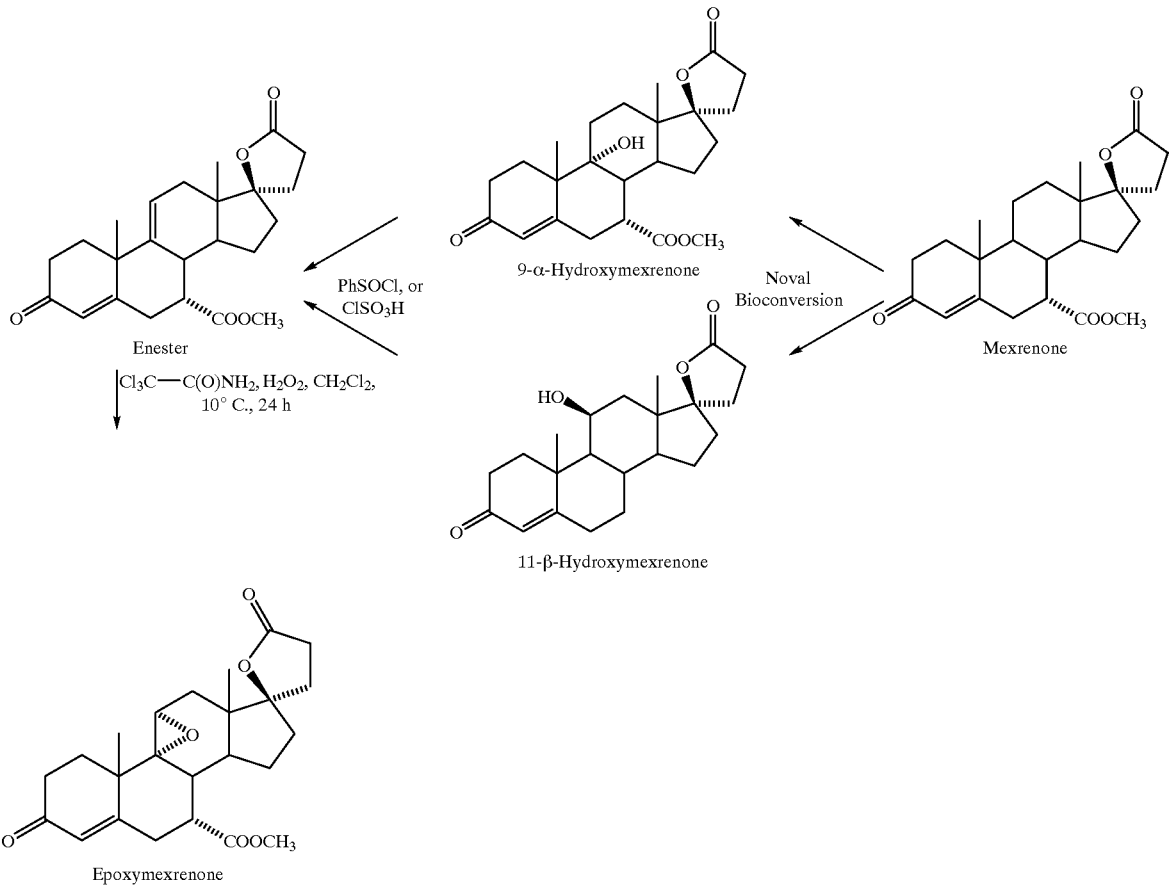

The synthesis in this case begins with a substrate corresponding to Formula XX

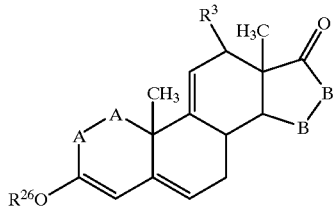

XX where —A—A— and $R^3$ are as defined in Formula VIII, —B—B— is as defined in Formula VIII except that neither $R^6$ nor $R^7$ is part of a ring fused to the D ring at the 16,17 positions, and $R^{26}$ is lower alhyl, preferably methyl. Reaction of the substrate of Formula XX with a sulfonium ylide produces the epoxide intermediate corresponding to Formula XIX

XIX

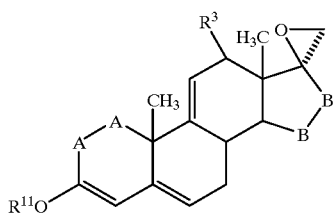

wherein —A—A—, $R^3$, —B—B—, and $R^{26}$ are as defined in Formula XX.

In the next step of synthesis scheme 3, the intermediate of Formula XIX is converted to a further intermediate of Formula XVIII

XVIII

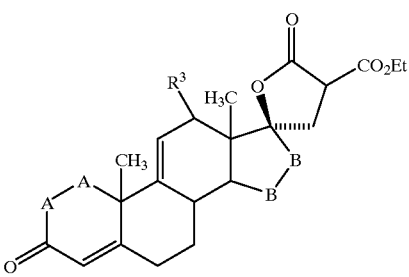

wherein —A—A—, $R^3$, and —B—B— are as defined in Formula XX. In this step, Formula XIX substrate is converted to Formula XVIII intermediate by reaction with $NaCH(COOEt)_2$ in the presence of a base in a solvent. Exposure of the compound of Formula XVIII to heat water and an alkali halide produces a decarboxylated intermediate compound corresponding to Formula XVII

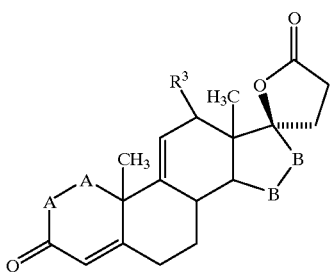

XVII wherein —A—A—, R³, and —B—B— are as defined in Formula XX. The process for conversion of the compound of Formula XX to the compound of Formula XVII corresponds essentially to that described in U.S. Pat. Nos. 3,897,417, 3,413,288 and 3,300,489, which are expressly incorporated herein by reference. While the substrates differ, the reagents, mechanisms and conditions for introduction of the 17-spirolactone moiety are essentially the same.

Reaction of the intermediate of Formula XVII with a dehydrogenation reagent yields the further intermediate of Formula XVI.

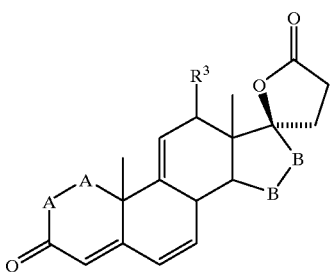

XVI where —A—A—, R³ and —B—B— are as defined above.

Typically useful dehydrogenation reagents include dichlorodicyanobenzoquinone (DDQ) and chloranil (2,3,5,6-tetrachloro-p-benzoquinone). Alternatively, the dehydrogenation could be achieved by a sequential halogenation at the carbon-6 followed by dehydrohalogenation reaction.

The intermediate of Formula XVI is next converted to the enamine of Formula XV

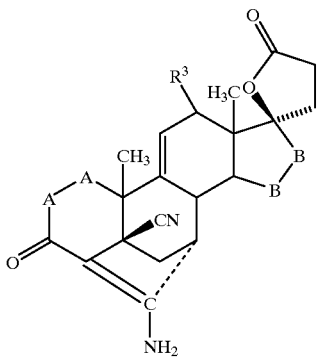

XV wherein —A—A—, R³, and —B—B— are as defined in Formula XX. Conversion is by cyanidation essentially in the manner described above for the conversion of the 11α-hydroxy compound of Formula VIII to the enamine of Formula VII. Typically, the cyanide ion source may be an alkali metal cyanide. The base is preferably pyrrolidine and/or tetramethylguanidine. A methanol solvent may be used.

The products of Formula XV are novel compounds, which may be isolated by chromatography. These and other novel compounds of Formula AXV have substantial value as intermediates for the preparation of compounds of Formula I, and especially of Formula IA. Compounds of Formula AXV correspond to the structure

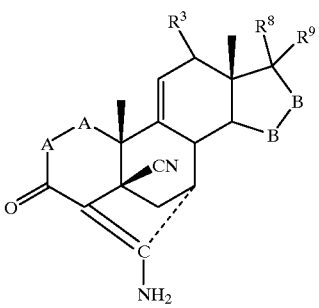

AXV where —A—A—, —B—B—, R³, R⁸ and R⁹ are as defined above. In the most preferred compounds of Formula XV, and —A—A— and —B—B— are —CH₂—CH₂—.

In accordance with the hydrolysis described above for producing the diketone compounds of Formula VI, the enamines of Formula XV may be converted to the diketones of Formula XIV

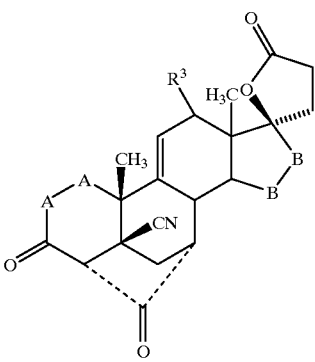

XIV wherein —A—A—, R³, and —B—B— are as defined in Formula XX. Particularly preferred for the synthesis of epoxymexrenone are those compounds of Formula XIV which also fall within the scope of Formula VIA.

The products of Formula XIV are novel compounds, which may be isolated by precipitation. These and other novel compounds of Formula AXIV have substantial value as intermediates for the preparation of compounds of Formula I, and especially of Formula IA. Compounds of Formula AXIV correspond to the structure

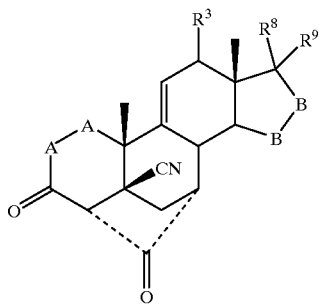

AXIV where —A—A—, —B—B—, $R^3$, $R^8$ and $R^9$ are as defined above. In the most preferred compounds of Formula AXIV and XIV, —A—A— and —B—B— are —CH$_2$—CH$_2$—.

The compounds of Formula XIV are further converted to compounds of Formula XXXI using essentially the process described above for converting the diketone of Formula VI to the hydroxyester of Formula V. In this instance, it is necessary to isolate the intermediate XXXI

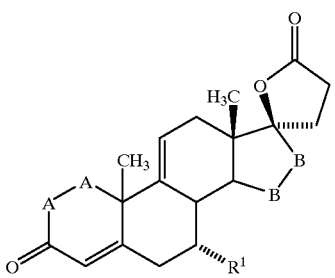

XXXI before further conversion to a product of Formula XXXII

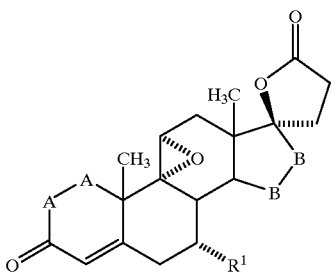

XXXII wherein —A—A— and —B—B— are as defined in Formula XX. Preferred compounds of Formula XXXI are those which fall within Formula IIA. The compounds of Formula XXXI are converted to compounds of Formula XXXII using the method described hereinabove or in U.S. Pat. No. 4,559,332. In a particularly preferred embodiment, the overall process of Scheme 3 proceeds as follows:

Scheme 4

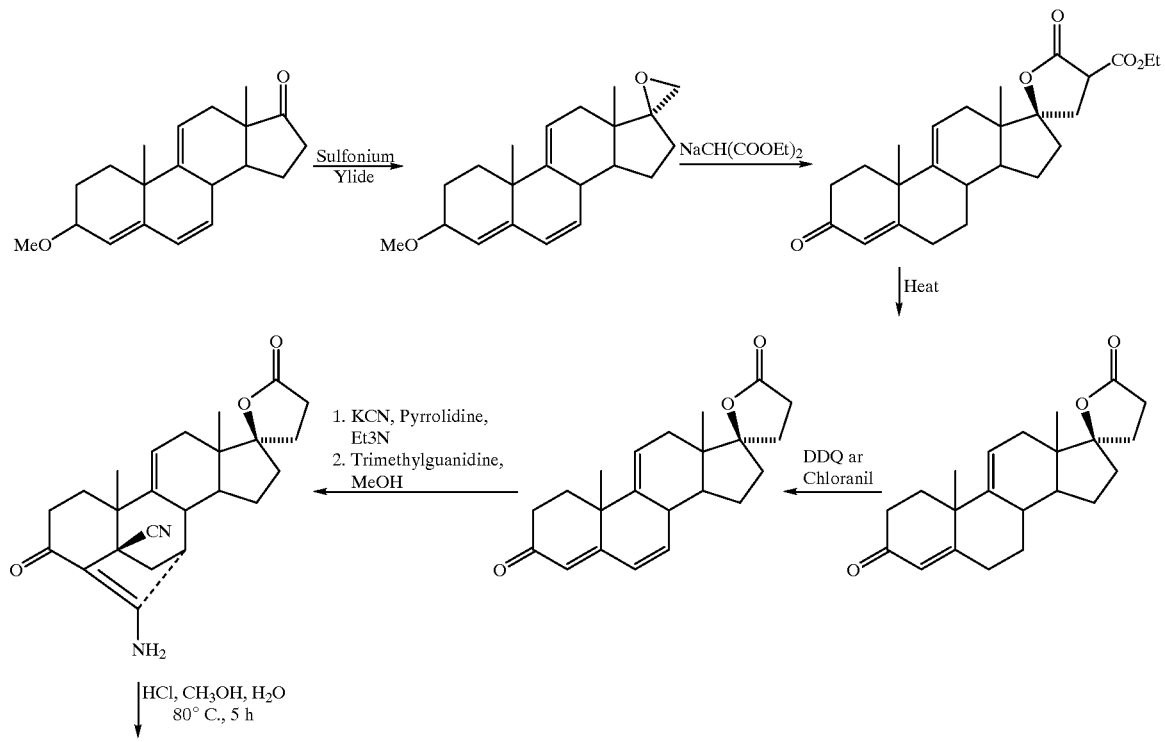

-continued

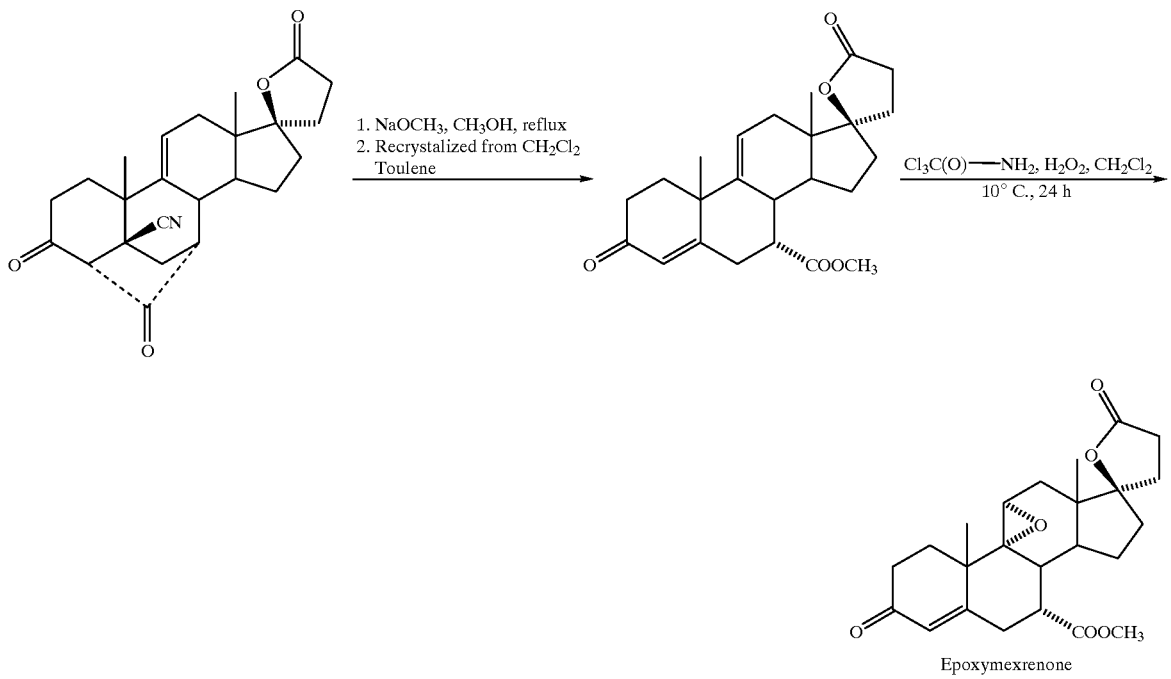

Epoxymexrenone

The first three steps of Scheme 4 are the same as those of Scheme 3, i.e., preparation of an intermediate of Formula XVII starting with a compound corresponding to Formula XX.

Thereafter, the intermediate of Formula XVII is epoxidized, for example, using the process of U.S. Pat. No. 4,559,332 to produce the compound of Formula XXIV

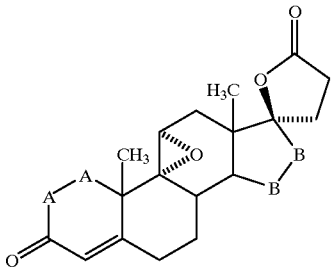

XXIV wherein —A—A—, $R^3$, and —B—B— are as defined in Formula XX. However, in a particularly preferred embodiment of the invention, the substrate of Formula XVII is epoxidized across the 9,11-double bond using an oxidation reagent comprising an amide type peroxide activator, most preferably trichloroacetamide, according to the process as described above in Scheme 1 for the conversion of the enester of Formula II to the product of Formula I. The conditions and proportions of reagents for this reaction are substantially as described for the conversion of the Formula II enester to epoxymexrenone.

It has been found that the epoxidation of the substrate of Formula XVII can also be effected in very good yield using a peracid such as, for example, m-chloroperoxybenzoic acid. However, the trichloroacetamide reagent provides superior results in minimizing the formation of Bayer-Villager oxidation by-product. The latter by-product can be removed, but this requires trituration from a solvent such as ethyl acetate, followed by crystallization from another solvent such as methylene chloride. The epoxy compound of Formula XXIV is dehydrogenated to produce a double bond between the 6- and 7-carbons by reaction with a dehydrogenation (oxidizing) agent such as DDQ or chloranil, or using the bromination/dehydrobromination (or other halogenation/dehydrohalogenation) sequence, to produce another novel intermediate of Formula XXIII

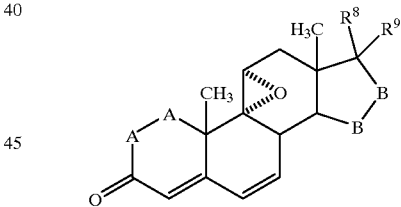

XXIII wherein —A—A—, and —B—B— are as defined in Formula XX. Particularly preferred compounds of Formula XXIII are those in which —A—A— and —B—B— are as defined in Formula XIII.

While direct oxidation is effective for the formation of the product of Formula XXIII, the yields are generally low. Preferably, therefore, the oxidation is carried out in two steps, first halogenating the substrate of Formula XXIV at the C-6 position, then dehydrohalogenating to the 6,7-olefin. Halogenation is preferably effected with an N-halo organic reagent such as, for example, N-bromosuccinamide. Bromination is carried out in a suitable solvent such as, for example, acetonitrile, in the presence of halogenation promoter such as benzoyl peroxide. The reaction proceeds effectively at a temperature in the range of about 50° to about 100° C., conveniently at atmospheric reflux tempera ture in a solvent such as carbon tetrachloride, acetonitrile or mixture thereof. However, reaction from 4 to 10 hours is typically required for completion of the reaction. The reaction solvent is stripped off, and the residue taken up a water-immiscible solvent, e.g., ethyl acetate. The resulting solution is washed sequentially with a mild alkaline solution (such as an alkali metal bicarbonate) and water, or preferably saturated brine to minimize product losses, after which the solvent is stripped and a the residue taken up in another solvent (such as dimethylformamide) that is suitable for the dehydrohalogenation reaction.

A suitable dehydrohalogenation reagent, e.g., 1,4-diazabicyclo[2,2,2]octane (DABCO) is added to the solution, along with an alkali metal halide such as LiBr, the solution heated to a suitable reaction temperature, e.g., 60° to 80° C., and reaction continued for several hours, typically 4 to 15 hours, to complete the dehydrobromination. Additional dehydrobromination reagent may be added as necessary during the reaction cycle, to drive the reaction to completion. The product of Formula XXIII may then be recovered, e.g., by adding water to precipitate the product which is then separated by filtration and preferably washed with additional amounts of water. The product is preferably recrystallized, for example from dimethylformamide.

The products of Formula XXIII, such as 9,11-epoxycanrenone, are novel compounds, which may be isolated by extraction/crystallization. They have substantial value as intermediates for the preparation of compounds of Formula I, and especially of Formula IA. For example, they may be used as substrates for the preparation of compounds of Formula XXII. In the most preferred compounds of Formula XXIII, and —A—A— and —B—B— are —CH$_2$—CH$_2$—.

Using substantially the process described above for the preparation of compounds of Formula VII, the compounds of Formula XXIII are reacted with cyanide ion to produce novel epoxyenamine compounds corresponding to Formula XXII

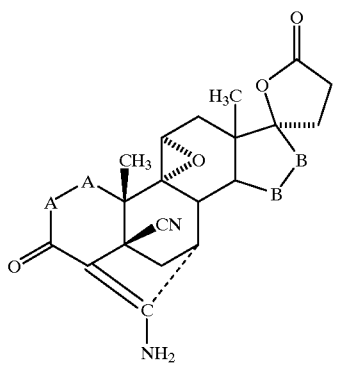

wherein —A—A—, R$^3$, and —B—B— are as defined in Formula XX. Particularly preferred compounds of Formula XXII are those in which —A—A— and —B—B— are as defined in Formula XIII.

The products of Formula XXII are novel compounds, which may be isolated by precipitation and filtration. They have substantial value as intermediates for the preparation of compounds of Formula I, and especially of Formula IA. In the most preferred compounds of Formula XXII, and —A—A— and —B—B— are —CH$_2$—CH$_2$—

Using substantially the process described above for preparation of compounds of Formula VI, the epoxyenamine compounds of Formula XXII are converted to novel epoxydiketone compounds of Formula XXI.

The products of Formula XXI are novel compounds, which may be isolated by precipitation and filtration. They have substantial value as intermediates for the preparation of compounds of Formula I, and especially of Formula IA. Particularly preferred compounds of Formula XXI are those in which —A—A— and —B—B— are as defined in Formula XIII. In the most preferred compounds of Formula XXI, and —A—A— and —B—B— are —CH$_2$—CH$_2$—.

Compounds of Formula XXI are converted to compounds of Formula XXXII using the epoxidation process described hereinabove or the process of U.S. Pat. No. 4,559,332. In a particularly preferred embodiment, the overall process of Scheme 4 proceeds as follows:

Scheme 5

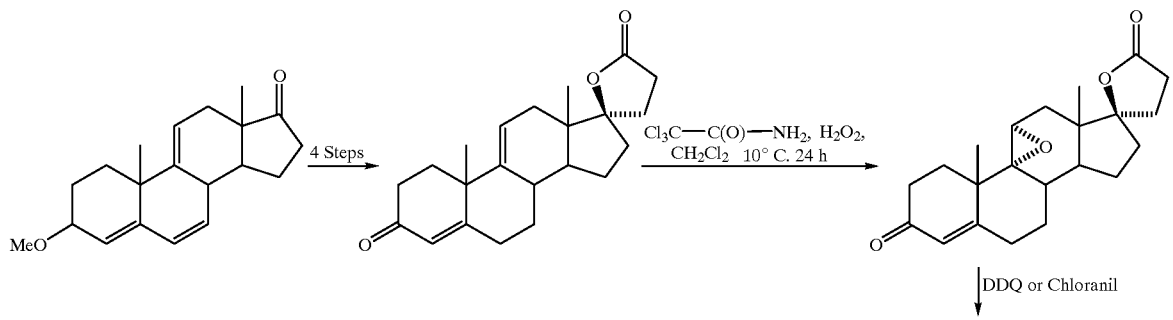

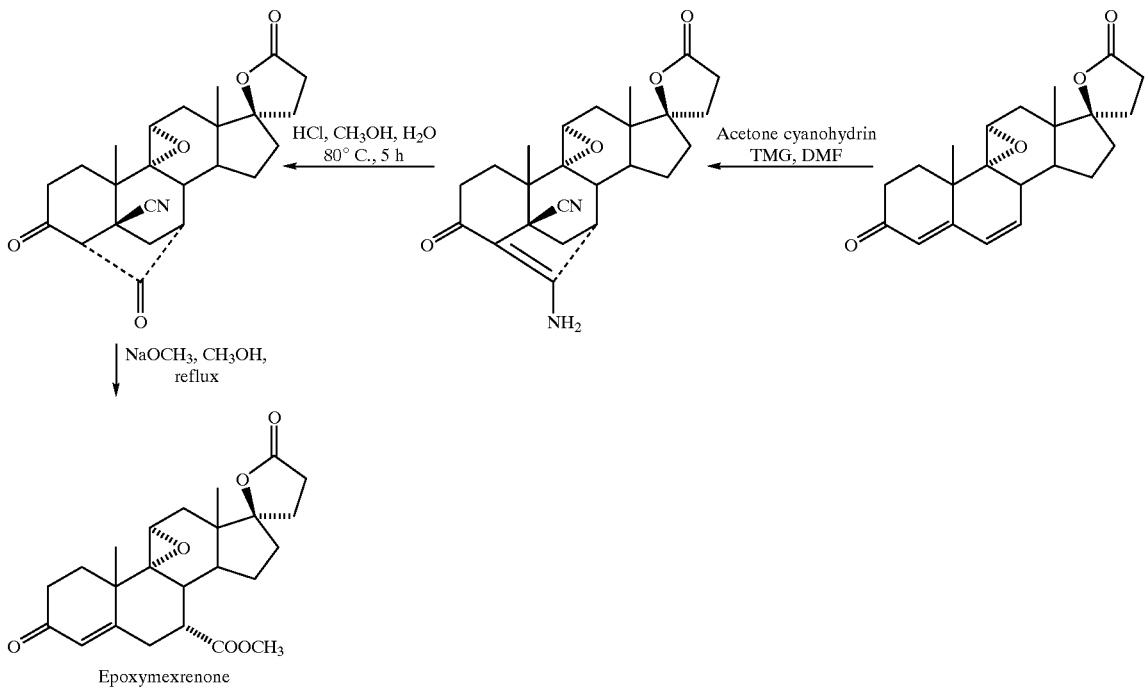

Epoxymexrenone

The process of scheme 5 begins with a substrate corresponding to Formula XXIX

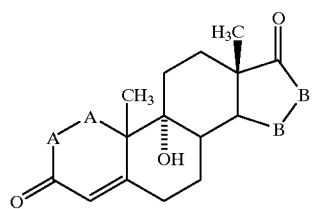

XXIX wherein —A—A—, and —B—B— are as defined in Formula XX. This substrate is converted to a product of Formula XXVIII

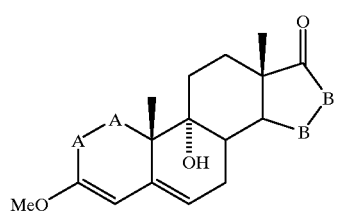

XXVIII by reaction with trimethylorthoformate. Wherein —A—A—, $R^3$, and —B—B— are as defined in Formula XX. Following the formation of Formula XXVIII, the compounds of Formula XXIX are converted to compounds of Formula XXVII using the method described above for conversion of the substrate of Formula XX to Formula XVII. Compounds of Formula XXVII have the structure:

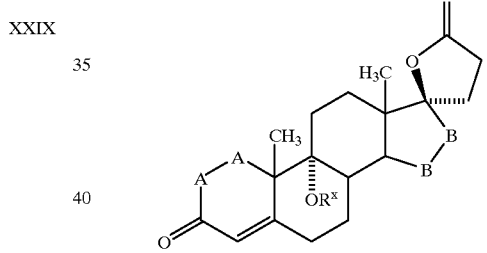

XXVII wherein —A—A—, and —B—B— are as defined in Formula XX, and $R^x$ is any of the common hydroxyl protecting groups.

Using the method described above for the preparation of compounds of Formula XVI, compounds of Formula XXVII are oxidized to yield novel compounds corresponding to Formula XXVI

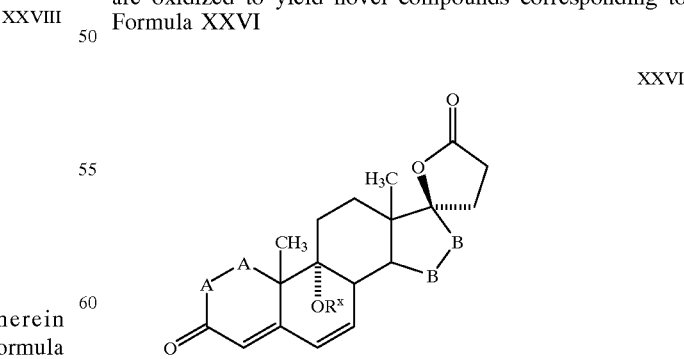

XXVI wherein —A—A—, and —B—B— are as defined in Formula XX. Particularly preferred compounds of Formulae XXIX, XXVIII, XXVII and XXVI are those in which —A—A— and —B—B— are as defined in Formula XIII.

The products of Formula XXVI are novel compounds, which may be isolated by precipitation/filtration. They have substantial value as intermediates for the preparation of compounds of Formula I, and especially of Formula IA. Particularly preferred compounds of Formula XXVI are those in which —A—A— and —B—B— are as defined in Formula XIII. In the most preferred compounds of Formula XXVI, and —A—A— and —B—B— are —CH$_2$—CH$_2$—.

Using the method defined above for cyanidation of compounds of Formula VIII, the novel intermediates of Formula XXVI are converted to the novel 9-hydroxyenamine intermediates of Formula XXV

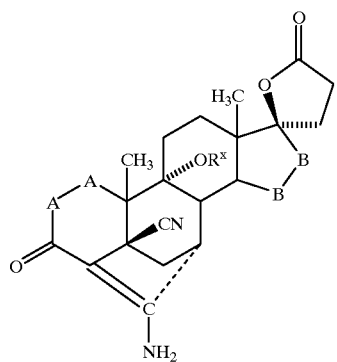

XXV wherein —A—A—, R$^3$, and —B—B— are as defined in Formula XX.

The products of Formula XXV are novel compounds, which may be isolated by precipitation/filtration. They have substantial value as intermediates for the preparation of compounds of Formula I, and especially of Formula IA. Particularly preferred compounds of Formula XXV are those in which —A—A— and —B—B— are as defined in Formula XIII. In the most preferred compounds of Formula XXVI, and —A—A— and —B—B— are —CH$_2$—CH$_2$—.

Using essentially the conditions described above for the preparation of the diketone compounds of Formula VI, the 9-hydroxyenamine intermediates of Formula XXV are converted to the diketone compounds of Formula XIV. Note that in this instance the reaction is effective for simultaneous hydrolysis of the enamine structure and dehydration at the 9,11 positions to introduce the 9,11 double bond. The compound of Formula XIV is then converted to the compound of Formula XXXI, and thence to the compound of Formula XIII, using the same steps that are described above in scheme 3.

In a particularly preferred embodiment, the overall process of Scheme 5 proceeds as follows:

Scheme 6

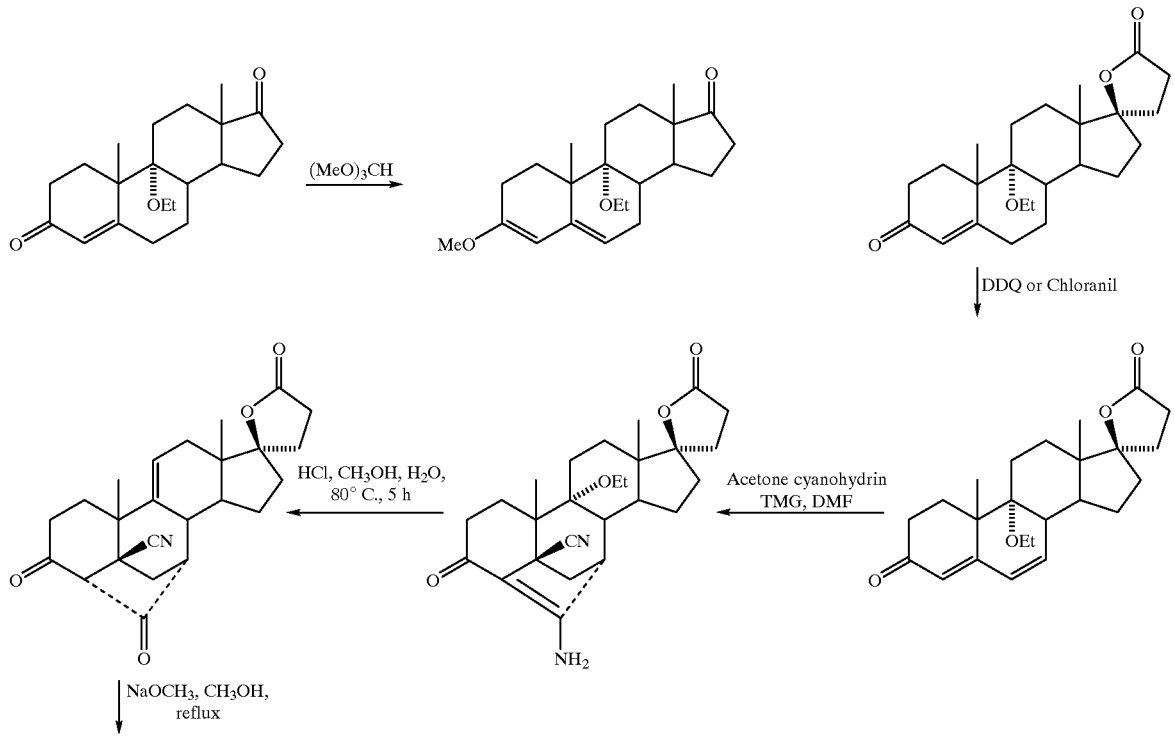

-continued

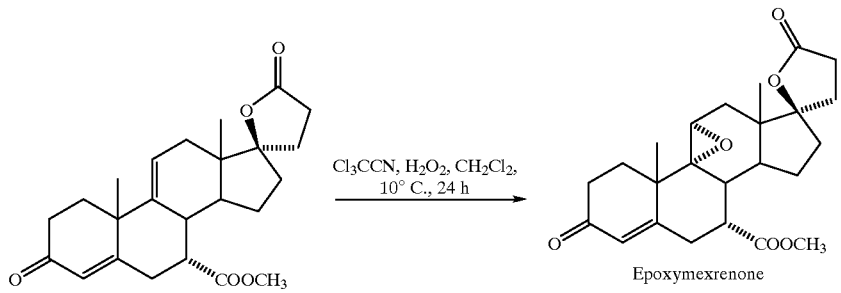
Epoxymexrenone

Scheme 6 provides an advantageous method for the preparation of epoxymexrenone and other compounds corresponding to Formula I, starting with 11α-hydroxylation of androstendione or other compound of Formula XXXV

XXXV

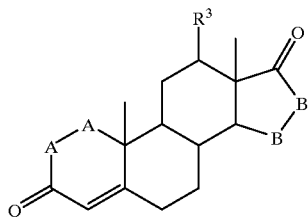

wherein —A—A—, $R^3$, and —B—B— are as defined in Formula XIII, producing an intermediate corresponding to the Formula XXXVI

XXXVI

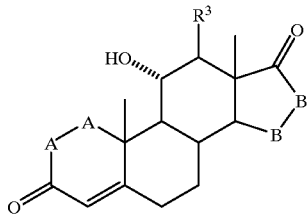

where —A—A—, $R^3$, and —B—B— are as defined in Formula XIII. Except for the selection of substrate, the process for conducting the 11α-hydroxylation is essentially as described hereinabove for Scheme 1. The following microorganisms are capable of carrying out the 11α-hydroxylation of androstendione or other compound of Formula XXXV:

*Aspergillus ochraceus* NRRL 405 (ATCC 18500);

*Aspergillus niger* ATCC 11394;

*Aspergillus nidulans* ATCC 11267;

*RhizoPus orvzae* ATCC 11145;

*Rhizopus stolonifer* ATCC 6227b;

*Trichothecium roseum* ATCC 12519 and ATCC 8685.

11α-Hydroxyandrost-4-ene-3,17-dione, or other compound of Formula XXXVI, is next converted to 11α-hydroxy-3,4-enol ether of Formula (101):

101

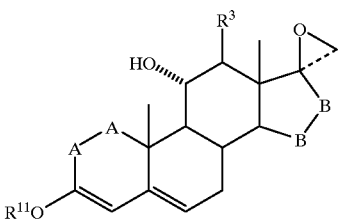

where —A—A—, $R^3$, and —B—B—, are as defined in Formula XIII and $R^{11}$ is methyl or other lower alkyl ($C_1$ to $C_4$), by reaction with an etherifying reagent such as trialkyl orthoformate in the presence of an acid catalyst. To carry out this conversion, the 11α-hydroxy substrate is acidified by mixing with an acid such as, e.g., benzene sulfonic acid hydrate or toluene sulfonic acid hydrate and dissolved in a lower alcohol solvent, preferably ethanol. A trialkyl orthoformate, preferably triethyl orthoformate is introduced gradually over a period of 5 to 40 minutes while maintaining the mixture in the cold, preferably at about 0° C. to about 15° C. The mixture is then warmed and the reaction carried out at a temperature of between 20° C. and about 60° C. Preferably the reaction is carried out at 30° to 50° C. for 1 to 3 hours, then heated to reflux for an additional period, typically 2 to 6 hours, to complete the reaction. Reaction mixture is cooled, preferably to 0° to 15°, preferably about 5° C., and the solvent removed under vacuum.

Using the same reaction scheme as described in Scheme 3, above, for the conversion of the compound of Formula XX to the compound of Formula XVII, a 17-spirolactone moiety of Formula XXXIII is introduced into the compound of Formula 101. For example, the Formula 101 substrate may be reacted with a sulfonium ylide in the presence of a base such as an alkali metal hydroxide in a suitable solvent such as DMSO, to produce an intermediate corresponding to Formula 102:

where —A—A—, $R^3$, $R^{11}$, and —B—B— are as defined in Formula 101. The intermediate of Formula 102 is then reacted with a malonic acid diester in the presence of an alkali metal alkoxide to form the five membered spirolactone ring and produce the intermediate of Formula 103

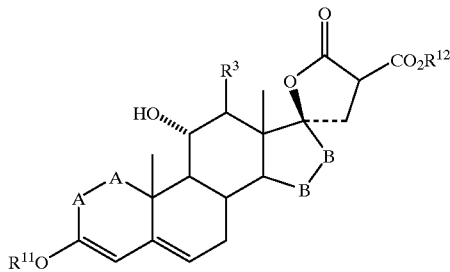

where —A—A—, $R^3$, $R^{11}$, $R^{12}$, and —B—B— are as defined in Formula XIII. Finally, the compound of Formula 103 in a suitable solvent, such as dimethylformamide, is subjected to heat in the presence of an alkali metal halide, splitting off the alkoxycarbonyl moiety and producing the intermediate of Formula 104:

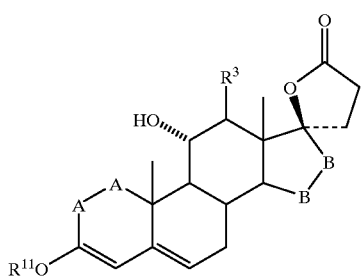

104 where again —A—A—, $R^3$, $R^{11}$ and —B—B— are as defined in Formula XIII.

Next the 3,4-enol ether compound 104 is converted to the compound of Formula XXIII, i.e., the compound of Formula VIII in which $R^8$ and $R^9$ together form the moiety of Formula XXXIII. This oxidation step is carried out in essentially the same manner as the oxidation step for conversion of the compound of Formula XXIV to the intermediate of Formula XXIII in the synthesis of Scheme 4. Direct oxidation can be effected using a reagent such as 2,3-dichloro-5,6-dicyano-1,4-benzoquinone (DDQ) or tetrachlorobenzoquinone (chloranil), or preferably a two stage oxidation is effected by first brominating, e.g., with an N-halo brominating agent such as N-bromosuccinamide or 1,3-dibromo-5,5-dimethyl hydantoin (DBDMH) and then dehydrobrominating with a base, for example with DABCO in the presence of LiBr and heat. Where NBS is used for bromination, an acid must also be employed to convert 3-enol ether to the enone. DBDMH, an ionic rather than free radical bromination reagent, is effective by itself for bromination and conversion of the enol ether to the enone.

The compound of Formula VIII is then converted to epoxymexrenone or other compound of Formula I by the steps described hereinabove for Scheme 1.

Each of the intermediates of Formulae 101, 102, 103, and 104 is a novel compound having substantial value as an intermediate for epoxymexrenone or other compounds of Formulae IA and I. In each of the compounds of Formulae 101, 102, 103, and 104 —A—A— and —B—B— are preferably —CH$_2$—CH$_2$— and $R^3$ is hydrogen, lower alkyl or lower alkoxy. Most preferably, the compound of Formula 101 is 3-ethoxy-11α-hydroxyandrost-3,5-dien-17-one, the compound of Formula 102 is 3-ethoxyspiro[androst-3,5-diene-17β,2'-oxiran]-11α-ol, the compound of Formula 103 is ethyl hydrogen 3-ethoxy-11α-17α-dihydroxypregna-3,5-diene-21,21-dicarboxylate, gamma-lactone, and the compound of Formula 104 is 3-ethoxy-11α-17α-dihydroxypregna-3,5-diene-21-carboxylic acid, gamma-lactone.

In a particularly preferred embodiment, the overall process of Scheme 6 proceeds as follows:

Scheme 7

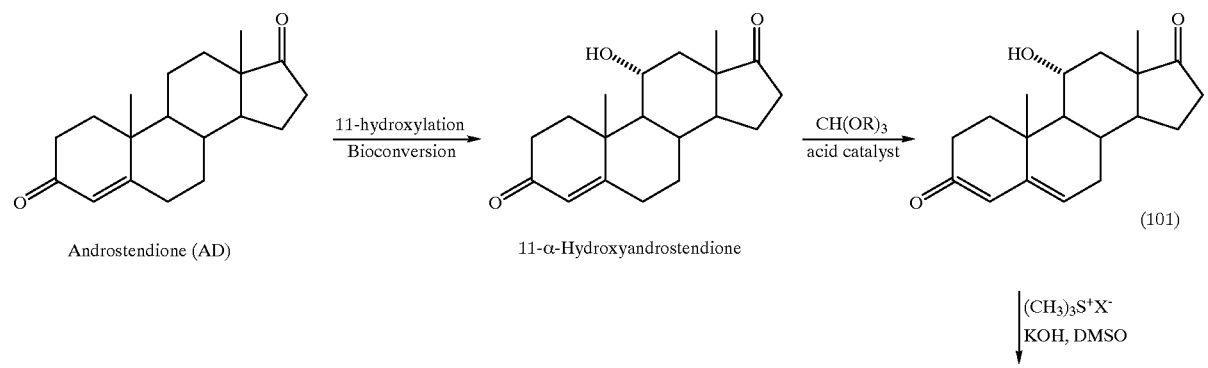

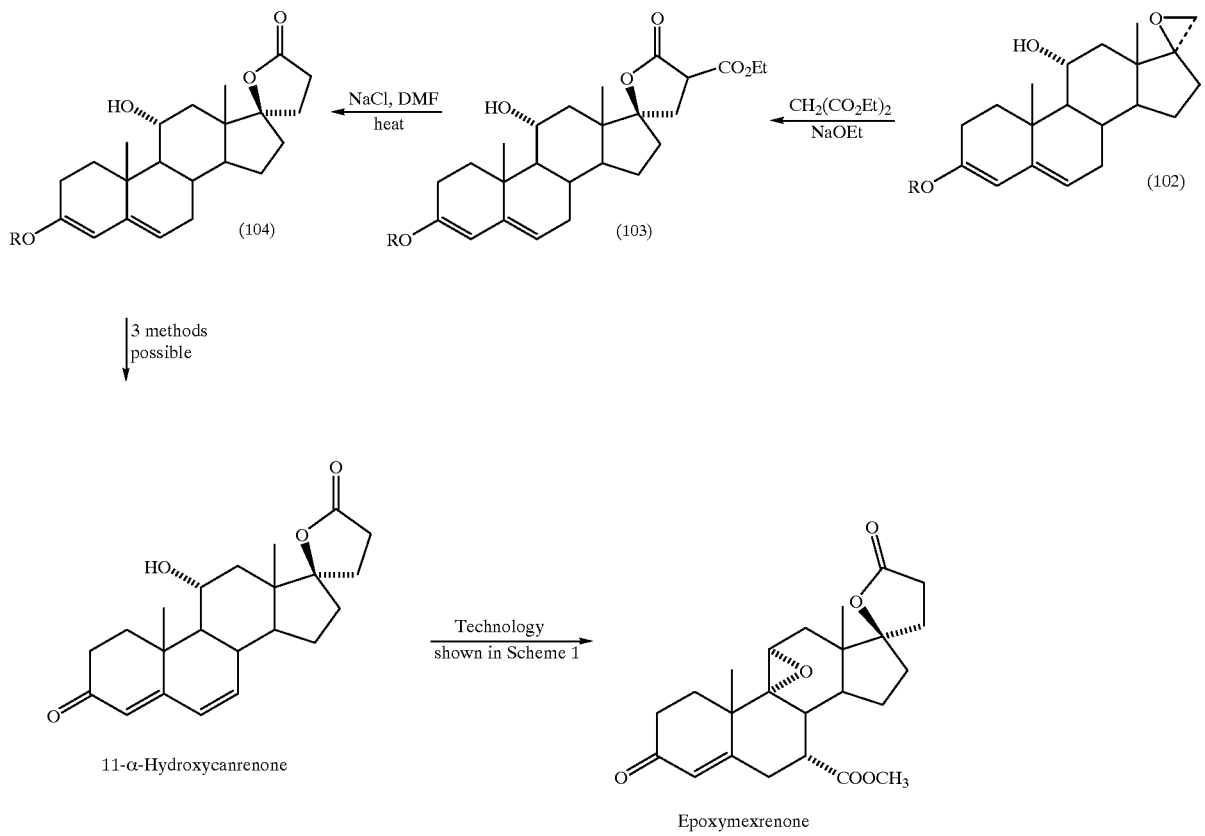

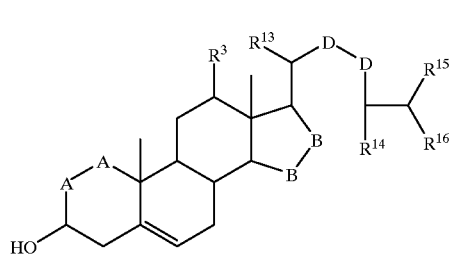

11-α-Hydroxycanrenone

Epoxymexrenone

Scheme 7 provides for the synthesis of epoxymexrenone and other compounds of Formula I using a starting substrate comprising β-sitosterol, cholesterol, stigmasterol or other compound of Formula XXXVII

XXXVII where —A—A—, $R^3$, and —B—B— are as defined in Formula XIII, D—D is —$CH_2$—$CH_2$— or —CH=CH—, and each of $R^{13}$, $R^{14}$, $R^{15}$ and $R^{16}$ is independently selected from among hydrogen or $C_1$ to $C_4$ alkyl.

In the first step of the synthesis 11α-hydroxyandrostendione or other compound of Formula XXXV is prepared by bioconversion of the compound of Formula XXXVII. The bioconversion process is carried out substantially in accordance with the method described hereinabove for the 11α-hydroxylation of canrenone (or other substrate of Formula XIII).

In the synthesis 11α-hydroxyandrostendione, 4-androstene-3,17-dione is initially prepared by bioconversion of the compound of Formula XXXVII. This initial bioconversion may be carried out in the manner described in U.S. Pat. No. 3,759,791, which is expressly incorporated herein by reference. Thereafter, 4-androstene-3,17-dione is converted to 11α-hydroxyandrostenedione substantially in accordance with the method described hereinabove for the 11α-hydroxylation of canrenone (or other substrate of Formula XIII).

The remainder of the synthesis of Scheme 7 is identical to Scheme 6. In a particularly preferred embodiment, the overall process of Scheme 7 proceeds as follows:

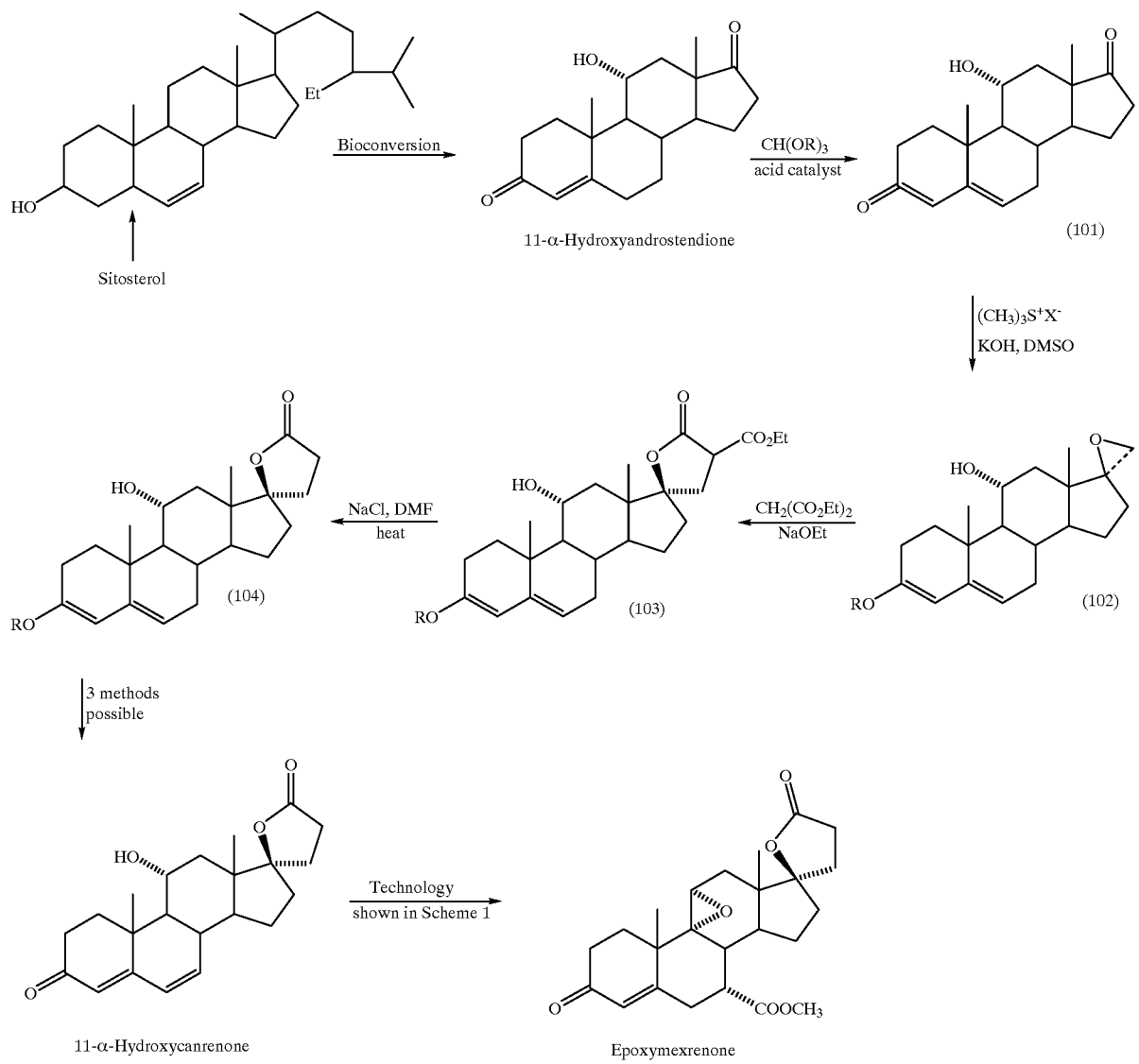

The methods, processes and compositions of the invention, and the conditions and reagents used therein, are further described in the following examples.

EXAMPLE 1

Slants were prepared with a growth medium as set forth in Table 1

TABLE 1

Y P D A (medium for slants and plates)

| | |
|---|---|
| yeast extract | 20 g |
| peptone | 20 g |
| glucose | 20 g |
| agar | 20 g |
| distilled water, q.s. to | 1000 ml | pH as is 6.7
adjust at pH 5 with $H_3PO_4$ 10% w/v

TABLE 1-continued

Y P D A (medium for slants and plates)

Distribute for slants: 7.5 ml in 180 × 18 mm tubes
for plates (10 cm of φ)
25 mL in 200 × 20 mm tubes
sterilize at 120° C. for 20 minutes
pH after sterilization: 5

To produce first generation cultures, a colony of *Aspergillus ochraceus* was suspended in distilled water (2 ml) in a test tube; and 0.15 ml aliquots of this suspension applied to each of the slants that had been prepared as described above. The slants were incubated for seven days at 25° C., after which the appearance of the surface culture was that of a white cottony mycelium. The reverse was pigmented in orange in the lower part, in yellow-orange in the upper part.

The first generation slant cultures were suspended in a sterile solution (4 ml) containing Tween 80 nonionic surfactant (3% by weight), and 0.15 ml aliquots of this suspension were used to inoculate second generation slants that had been prepared with the growth medium set forth in Table 2

TABLE 2

(for second generation and routine slants)

| | |
|---|---|
| malt extract | 20 g |
| peptone | 1 g |
| glucose | 20 g |
| agar | 20 g |
| distilled water q.s. to | 1000 ml | pH as is 5.3
distribute in tubes (180 × 18 mm) ml 7.5
sterilize at 120° C. for 20 minutes The second generation slants were incubated for 10 days at 25° C., producing a heavy mass of golden-colored spores; reverse pigmented in brown orange.

A protective medium was prepared having the composition set forth in Table 3.

TABLE 3

PROTECTIVE MEDIUM

| | |
|---|---|
| Skim milk | 10 g |
| distilled water | 100 ml |
| In a 250 ml flask containing 100 ml of distilled water at 50° C., add skim milk. Sterilize at 120° C. for 15 minutes. Cool at 33° C. and use before the day is over | |

Cultures from five of the second generation slants were suspended in the protective solution (15 ml) in a 100 ml flask. The suspension was distributed in aliquots (0.5 ml each) among 100×10 mm tubes for lyophilization. These were pre-frozen at −70° to −80° C. in an acetone/dry ice bath for 20 minutes, then transferred immediately to a drying room pre-cooled to −40° to −50° C. The pre-frozen aliquots were lyophilized at a residual pressure of 50µHg and ≦−30° C. At the end of the lyophilization, two to three granules of sterile silica gel were added to each tube with moisture indicator and flame seal.

To obtain mother culture slants suitable for industrial scale fermentation, a single aliquot of lyophilized culture, which had been prepared in the manner described above, was suspended in distilled water (1 ml) and 0.15 ml aliquots of the suspension were used to inoculate slants that had been provided with a growth medium having the composition set forth in Table 2. The mother slants were incubated for seven days at 25° C. At the end of incubation, the culture developed on the slants was preserved at 4° C.

To prepare a routine slant culture, the culture from a mother slant was suspended in a sterile solution (4 ml) containing Tween 80 (3% by weight) and the resulting suspension distributed in 0.15 ml aliquots among slants which had been coated with the growth medium described in Table 2. The routine slant cultures may be used to inoculate the primary seed flasks for laboratory or industrial fermentations.

To prepare a primary seed flask culture, the culture from a routine slant, which had been prepared as described above, was removed and suspended in a solution (10 ml) containing Tween 80 (3% by weight). A 0.1 aliquot of the resulting suspension was introduced into a 500 ml baffled flask containing a growth medium having the composition set forth in Table 4.

TABLE 4

(for primary and transformation flask culture and round bottomed flask)

| | |
|---|---|
| glucose | 20 g |
| peptone | 20 g |
| yeast autolysate | 20 g |
| distilled water q.s to | | pH as is 5.2
adjust at pH 5.8 with NaOH 20%
distribute in 500 ml baffled flask 100 ml
distribute in 2000 ml round
bottomed flasks (3 baffles) 500 ml
sterilize 120° C. × 20 min.
pH after sterilization about 5.7

The seed flask was incubated on a rotating shaker (200 rpm, 5 cm displacement) for 24 hours at 28° C., thereby producing a culture in the form of pellet-like mycelia having diameters of 3 to 4 mm. On microscopic observation, the seed culture was found to be a pure culture, with synnematic growth, with big hyphae and well twisted. The pH of the suspension was 5.4 to 5.6. PMV was 5 to 8% as determined by centrifugation (3000 rpm×5 min.).

A transformation flask culture was prepared by inoculating a growth medium (100 ml) having the composition set forth Table 4 in a second 500 ml shaker flask with biomass (1 ml) from the seed culture flask. The resulting mixture was incubated on a rotating shaker (200 rpm, 5 cm displacement) for 18 hours at 28° C. The culture was examined and found to comprise pellet like mycelia with a 3–4 mm diameter. On microscopic examination, the culture was determined to be a pure culture, with synnematic and filamentous growth in which the apical cells were full of cytoplasm and the olden cells were little vacuolated. The pH of the culture suspension was 5 to 5.2 and the PMV was determined by centrifugation to be between 10% and 15%. Accordingly, the culture was deemed suitable for transformation of canrenone to 11α-hydroxycanrenone.

Canrenone (1 g) was micronized to about 5µ and suspended in sterile water (20 ml). To this suspension were added: a 40% (w/v) sterile glucose solution; a 16% (w/v) sterile solution of autolyzed yeast; and a sterile antibiotic solution; all in the proportions indicated for 0 hours reaction time in Table 5. The antibiotic solution had been prepared by dissolving kanamicyn sulfate (40 mg), tetracycline HCl (40 mg) and cefalexin (200 mg) in water (100 ml). The steroid suspension, glucose solution, and autolyzed yeast solution were added gradually to the culture contained in the shaker flask.

TABLE 5

Indicative Additions of Steroid and Solutions
(additives and antibiotics) in the Course
of Bioconversion of Canrenone in Shake Flask

| Reaction | Steroid Suspension | | glucose | yeast autolised | antibiotic |
|---|---|---|---|---|---|
| time hours | ml | approx. mg. | solution ml | sol. ml. | solution ml |
| 0 | 1 | 50 | 1 | 0.5 | 1 |
| 8 | 2 | 100 | 2 | 1 | 1 |
| 24 | 2 | 100 | 1 | 0.5 | 1 |

TABLE 5-continued

Indicative Additions of Steroid and Solutions
(additives and antibiotics) in the Course
of Bioconversion of Canrenone in Shake Flask

| Reaction time hours | Steroid Suspension ml | approx. mg. | glucose solution ml | yeast autolised sol. ml. | antibiotic solution ml |
|---|---|---|---|---|---|
| 32 | 5 | 250 | 2 | 1 | |
| 48 | 2 | 100 | 1 | 0.5 | 1 |
| 56 | 5 | 250 | 2 | 1 | |
| 72 | 3 | 150 | 1 | 0.5 | 1 |
| 90 | | | | | |

As reaction proceeded, the reaction mixture was periodically analyzed to determine glucose content, and by thin layer chromatography to determine conversion to 11α-hydroxycanrenone. Additional canrenone substrate and nutrients were added to the fermentation reaction mixture during the reaction at rates controlled to maintain the glucose content in the range of about 0.1% by weight. The addition schedule for steroid suspension, glucose solution, autolyzed yeast solution and antibiotic solution is set forth in Table 5. The transformation reaction continued for 96 hours at 25° C. on a rotary shaker (200 rpm and 5 cm displacement). The pH ranged between 4.5 and 6 during the fermentation. Whenever the PMV rose to or above 60%, a 10 ml portion of broth culture was withdrawn and replaced with 10 ml distilled water. The disappearance of canrenone and appearance of 11α-hydroxycanrenone were monitored during the reaction by sampling the broth at intervals of 4, 7, 23, 31, 47, 55, 71, 80, and 96 hours after the start of the fermentation cycle, and analyzing the sample by TLC. The progress of the reaction as determined from these samples is set forth in Table 6

TABLE 6

Time Course of Bioconversion
of Canrenone in Shake Flask

| | Transformation Ratio | |
|---|---|---|
| Time hours | Canrenone Rf. RF. = 0.81 | 11αhydroxy Canrenone RF. = 0.29 |
| 0 | 100 | 0.0 |
| 4 | 50 | 50 |
| 7 | 20 | 80 |
| 23 | 20 | 80 |
| 31 | 30 | 70 |
| 47 | 20 | 80 |
| 55 | 30 | 70 |
| 71 | 25 | 75 |
| 80 | 15 | 85 |
| 96 | ~10 | ~90 |

EXAMPLE 2

A primary seed flask culture was prepared in the manner described in Example 1. A nutrient mixture was prepared having the composition set forth in Table 7

TABLE 7

For Transformation Culture
in 10 l glass fermenter

| | quantity | g/l |
|---|---|---|
| glucose | 80 g | 20 |
| peptone | 80 g | 20 |
| yeast autolised | 80 g | 20 |
| antifoam SAG 471 | 0.5 g | |
| deionized water q.s. to | 4 l | |
| sterilize the empty fermenter for 30 minutes at 130° C. load it with 3 l of deionized water, heat at 40° C. add while stirring the components of the medium stir for 15 minutes, bring to volume of 3.9 l pH as is 5.1 adjust of 5.8 with NaOH 20% w/v sterilize at 120° C. × 20 minutes pH after sterilization 5.5–5.7 | | |

An initial charge of this nutrient mixture (4L) was introduced into a transformation fermenter of 10 L geometric volume. The fermenter was of cylindrical configuration with a height to diameter ratio of 2.58. It was provided with a 400 rpm turbine agitator having two No. 2 disk wheels with 6 blades each. The external diameter of the impellers was 80 mm, each of the blades was 25 mm in radial dimension and 30 mm high, the upper wheel was positioned 280 mm below the top of the vessel, the lower wheel was 365 mm below the top, and baffles for the vessel were 210 mm high and extended radially inwardly 25 mm from the interior vertical wall of the vessel.

Seed culture (40 ml) was mixed with the nutrient charge in the fermenter, and a transformation culture established by incubation for 22 hours at 28° C., and an aeration rate of 0.5 l/l-min. at a pressure of 0.5 kg/cm². At 22 hours, the PMV of the culture was 20–25% and the pH 5 to 5.2.

A suspension was prepared comprising canrenone (80 g) in sterile water (400 ml), and a 10 ml portion added to the mixture in the transformation fermenter. At the same time a 40% (w/v) sterile glucose solution, a 16% (w/v) sterile solution of autolyzed yeast, and a sterile antibiotic solution were added in the proportions indicated in Table 8 at 0 hours reaction time. The antibiotic solution was prepared in the manner described in Example 1.

TABLE 8

Indicative Additions of Steroid and Solutions
(additives and antibiotics) in the Course
of Bioconversion of Canrenone in
10 l Glass Fermenter

| Reaction time hours | Steroid Suspension ml | approx. gr | glucose solution ml | yeast autolised sol. ml | antibiotic solution ml |
|---|---|---|---|---|---|
| 0 | 10 | 4 | 25 | 12.5 | 40 |
| 4 | | | 25 | 12.5 | |

TABLE 8-continued

Indicative Additions of Steroid and Solutions
(additives and antibiotics) in the Course
of Bioconversion of Canrenone in
10 l Glass Fermenter

| Reaction time hours | Steroid Suspension approx. ml gr | | glucose solution ml | yeast autolised sol. ml | anti- biotic solution ml |
|---|---|---|---|---|---|
| 8  | 10   | 4 | 25 | 12.5 |    |
| 12 |      |   | 25 | 12.5 |    |
| 16 | 10   | 4 | 25 | 12.5 |    |
| 20 |      |   | 25 | 12.5 |    |
| 24 | 10   | 4 | 25 | 12.5 | 40 |
| 28 | 10   | 4 | 25 | 12.5 |    |
| 32 | 12.5 | 5 | 25 | 12.5 |    |
| 36 | 12.5 | 5 | 25 | 12.5 |    |
| 40 | 12.5 | 5 | 25 | 12.5 |    |
| 44 | 12.5 | 5 | 25 | 12.5 |    |
| 48 | 12.5 | 5 | 25 | 12.5 | 40 |
| 52 | 12.5 | 5 | 25 | 12.5 |    |
| 56 | 12.5 | 5 | 25 | 12.5 |    |
| 60 | 12.5 | 5 | 25 | 12.5 |    |
| 64 | 12.5 | 5 | 25 | 12.5 |    |
| 68 | 12.5 | 5 | 25 | 12.5 |    |
| 72 | 12.5 | 5 | 25 | 12.5 | 40 |
| 76 | 12.5 | 5 | 25 | 12.5 |    |
| 80 |      |   |    |      |    |
| 84 |      |   |    |      |    |
| 88 |      |   |    |      |    |

As reaction proceeded, the reaction mixture was periodically analyzed to determine glucose content, and by thin layer chromatography to determine conversion to 11α-hydroxycanrenone. Based on TLC analysis of reaction broth samples as described hereinbelow, additional canrenone was added to the reaction mixture as canrenone substrate was consumed. Glucose levels were also monitored and, whenever glucose concentration dropped to about 0.05% by weight or below, supplemental glucose solution was added to bring the concentration up to about 0.25% by weight. Nutrients and antibiotics were also added at discrete times during the reaction cycle. The addition schedule for steroid suspension, glucose solution, autolyzed yeast solution and antibiotic solution is set forth in Table 8. The transformation reaction continued for 90 hours at an aeration rate of 0.5 vol. air per vol. liquid per minute (vvm) at a positive head pressure of 0.3 kg/cm$^2$. The temperature was maintained at 28° C. until PVM reached 45%, then decreased to 26° C. and maintained at that temperature as PVM grew from 45% to 60%, and thereafter controlled at 24° C. The initial agitation rate was 400 rpm, increasing to 700 rpm after 40 hours. The pH was maintained at between 4.7 and 5.3 by additions of 2M orthophosphoric acid or 2M NaOH, as indicated. Foaming was controlled by adding a few drops of Antifoam SAG 471 as foam developed. The disappearance of canrenone and appearance of 11α-hydroxycanrenone were monitored at 4 hour intervals during the reaction by TLC analysis of broth samples. When most of the canrenone had disappeared from the broth, additional increments were added.

After all canrenone additions had been made, the reaction was terminated when TLC analysis showed that the concentration of canrenone substrate relative to 11α-hydroxycanrenone product had dropped to about 5%.

At the conclusion of the reaction cycle, the fermentation broth was filtered through cheese cloth for separation of the mycelium from the liquid broth. The mycelia fraction was resuspended in ethyl acetate using about 65 volumes (5.2 liters) per gram canrenone charged over the course of the reaction. The suspension of mycelia in ethyl acetate was refluxed for one hour under agitation, cooled to about 20° C., and filtered on a Buchner. The mycelia cake was washed sequentially with ethyl acetate (5 vol. per g canrenone charge; 0.4 L) and deionized water (500 ml) to displace the ethyl acetate extract from the cake. The filter cake was discarded. The rich extract, solvent washing and water washing were collected in a separator, then allowed to stand for 2 hours for phase separation.

The aqueous phase was then discarded and the organic phase concentrated under vacuum to a residual volume of 350 ml. The still bottoms were cooled to 15° C. and kept under agitation for about one hour. The resulting suspension was filtered to remove the crystalline product, and the filter cake was washed with ethyl acetate (40 ml). After drying, the yield of 11α-hydroxycanrenone was determined to be 60 g.

EXAMPLE 3

A spore suspension was prepared from a routine slant in the manner described in Example 1. In a 2000 ml baffled round bottomed flask (3 baffles, each 50 mm×30 mm), an aliquot (0.5 ml) of the spore suspension was introduced into a nutrient solution (500 ml) having the composition set forth in Table 4. The resulting mixture was incubated in the flask for 24 hours at 25° C. on an alternating shaker (120 strokes per min.; displacement 5 cm), thereby producing a culture which, on microscopic examination, was observed to appear as a pure culture with hyphae well twisted. The pH of the culture was between about 5.3 and 5.5, and the PMV (as determined by centrifugation at 3000 rpm for 5 min.) was 8 to 10%.

Using the culture thus prepared, a seed culture was prepared in a stainless steel fermenter of vertical cylindrical configuration, having a geometric volume of 160 L and an aspect ratio of 2.31 (height=985 mm; diameter=425 mm). The fermenter was provided with a disk turbine type agitator having two wheels, each wheel having six blades with an external diameter of 240 mm, each blade having a radial dimension of 80 mm and a height of 50 mm. The upper wheel was positioned at a depth of 780 mm from the top of the fermenter, and the second at a depth of 995 mm. Vertical baffles having a height of 890 mm extended radially inwardly 40 mm from the interior vertical wall of the fermenter. The agitator was operated at 170 rpm. A nutrient mixture (100 L) having the composition set forth in Table 9 was introduced into the fermenter, followed by a portion of preinoculum (1 L) prepared as described above and having a pH of 5.7.

TABLE 9

For Vegetative Culture in 160 L
Fermenter About 8 L are needed
to Seed Productive fermenter

|  | Quantity | | g/L |
|---|---|---|---|
| glucose | 2 | kg | 20 |
| peptone | 2 | kg | 20 |
| yeast autolysed | 2 | kg | 20 |
| antifoam SAG 471 | 0.010 | Kg | traces |
| deionized water q.s. to | 100 | L | | sterilize the empty
fermenter for 1 hour
at 130° C.
load it with 6 L of

TABLE 9-continued

For Vegetative Culture in 160 L
Fermenter About 8 L are needed
to Seed Productive fermenter

| | Quantity | g/L |
|---|---|---|
| deionized water; heat at 40° C. add while stirring the components of the medium stir for 15 minutes, bring to volume of 95 L sterilization at 121° C. for 30 minutes post sterilization pH is 5.7 add sterile deionized water to 100 L | | |

The inoculated mixture was incubated for 22 hours at an aeration rate of 0.5 L/L-min. at a head pressure of 0.5 kg/cm$^2$. The temperature was controlled at 28° C. until PMV reached 25%, and then lowered to 25° C. The pH was controlled in the range of 5.1 to 5.3. Growth of mycelium volume is shown in Table 10, along with pH and dissolved oxygen profiles of the seed culture reaction.

TABLE 10

Time Course for Mycelial Growth in
Seed Culture Fermentation

| Fermentation period h | pH | packed mycelium volume (pmv) % (3000 rpms 5 min) | dissolved oxygen % |
|---|---|---|---|
| 0 | 5.7 ± 0.1 | | 100 |
| 4 | 5.7 ± 0.1 | | 100 |
| 8 | 5.7 ± 0.1 | 12 ± 3 | 85 ± 5 |
| 12 | 5.7 ± 0.1 | 15 ± 3 | 72 ± 5 |
| 16 | 5.5 ± 0.1 | 25 ± 5 | 40 ± 5 |
| 20 | 5.4 ± 0.1 | 30 ± 5 | 35 ± 5 |
| 22 | 5.3 ± 0.1 | 33 ± 5 | 30 ± 5 |
| 24 | 5.2 ± 0.1 | 35 ± 5 | 25 ± 5 |

Using the seed culture thus produced, a transformation fermentation run was carried out in a vertical cylindrical stainless steel fermenter having a diameter of 1.02 m, a height of 1.5 m and a geometric volume of 1.4 m$^3$. The fermenter was provided with a turbine agitator having two impellers, one positioned 867 cm below the top of the reactor and the other positioned 1435 cm from the top. Each wheel was provided with six blades, each 95 cm in radial dimension and 75 cm high. Vertical baffles 1440 cm high extended radially inwardly 100 cm from the interior vertical wall of the reactor. A nutrient mixture was prepared having the composition set forth in Table 11

TABLE 11

For Bioconversion Culture in 1000 L Fermenter

| | Quantity | g/L |
|---|---|---|
| glucose | 16 kg | 23 |
| peptone | 16 kg | 23 |
| yeast autolysed | 16 kg | 23 |
| antifoam SAG 471 | 0.080 Kg | traces |
| deionized water q.s. to | 700 L | |
| sterilize the empty fermenter for 1 hour at 130° C. | | |

TABLE 11-continued

For Bioconversion Culture in 1000 L Fermenter

| | Quantity | g/L |
|---|---|---|
| load it with 600 L of deionized water; heat at 40° C. add while stirring the components of the medium stir for 15 minutes, bring to volume of 650 L sterilization at 121° C. for 30 minutes post sterilization pH is 5.7 add sterile deionized water to 700 L | | |

An initial charge (700 L) of this nutrient mixture (pH=5.7) was introduced into the fermenter, followed by the seed inoculum of this example (7 L) prepared as described above.

The nutrient mixture containing inoculum was incubated for 24 hours at an aeration rate of 0.5L/L-min at a head pressure of 0.5 kg/cm$^2$. The temperature was controlled at 28° C., and the agitation rate was 110 rpm. Growth of mycelium volume is shown in Table 12, along with pH and dissolved oxygen profiles of the seed culture reaction.

TABLE 12

Time Course for Mycelial Growth in
Fermenter of the Transformation Culture

| Fermentation period h | pH | packed mycelium volume (pmv) % (3000 rpm × 5 min) | dissolved oxygen % |
|---|---|---|---|
| 0 | 5.6 ± 0.2 | | 100 |
| 4 | 5.5 ± 0.2 | | 100 |
| 8 | 5.5 ± 0.2 | 12 ± 3 | 95 ± 5 |
| 12 | | 15 ± 3 | 90 ± 5 |
| 16 | 5.4 ± 0.1 | 20 ± 5 | 75 ± 5 |
| 20 | 5.3 ± 0.1 | 25 ± 5 | 60 ± 5 |
| 22 | 5.2 ± 0.1 | 30 ± 5 | 40 ± 5 |

At the conclusion of the incubation, pelleting of the mycelium was observed, but the pellets were generally small and relatively loosely packed. Diffuse mycelium was suspended in the broth. Final pH was 5.1 to 5.3.

To the transformation culture thus produced was added a suspension of canrenone (1.250 kg; micronized to 5μ) in sterile water (5 L). Sterile additive solution and antibiotic solution were added in the proportions indicated at reaction time 0 in Table 14. The composition of the additive solution is set forth in Table 13.

TABLE 13

ADDITIVE SOLUTION
(for transformative culture)

| | quantity |
|---|---|
| dextrose | 40 Kg |
| yeast autolysate | 8 Kg |
| antifoam SAG 471 | 0.010 Kg |
| deionized water q.s. to | 100 l |
| sterilize a 150 l empty fermenter for 1 hour at 130° C. load it with 70 l of | |

TABLE 13-continued

ADDITIVE SOLUTION
(for transformative culture)

| | quantity |
|---|---|
| deionized water; heat at 40° C. add while stirring the components of "additive solution" stir for 30 minutes, bring to volume of 95 l pH as is 4.9 sterilize at 120° C. × 20 minutes pH after sterilization about 5 | |

Bioconversion was carried out for about 96 hours with aeration at 0.5 L/L-min. at a head pressure of 0.5 kg/cm² and a pH of ranging between 4.7 and 5.3, adjusted as necessary by additions of 7.5 M NaOH or 4 M $H_3PO_4$. The agitation rate was initially 100 rpm, increased to 165 rpm at 40 hours and 250 rpm at 64 hours. The initial temperature was 28° C., lowered to 26° C. when PMV reached 45%, and lowered to 24° C. when PMV rose to 60%. SAG 471 in fine drops was added as necessary to control foaming. Glucose levels in the fermentation were monitored at 4 hour intervals and, whenever the glucose concentration fell below 1 gpl, an increment of sterile additive solution (10 L) was added to the batch. Disappearance of canrenone and appearance of 11α-hydroxycanrenone were also monitored during the reaction by HPLC. When at least 90% of the initial canrenone charge had been converted to 11α-hydroxycanrenone, an increment of 1.250 kg canrenone was added. When 90% of the canrenone in that increment was shown to have been converted, another 1.250 kg increment was introduced. Using the same criterion further increments (1.250 kg apiece) were added until the total reactor charge (20 kg) had been introduced. After the entire canrenone charge had been delivered to the reactor, reaction was terminated when the concentration of unreacted canrenone was 5% relative to the amount of 11α-hydroxycanrenone produced. The schedule for addition of canrenone, sterile additive solution, and antibiotic solution is as shown in Table 14.

TABLE 14

Additions of the Steroid and Solutions
(additives and antibiotics)
in the Course of Bioconversion of Canrenone
in Fermenter

| Reaction time hours | CANRENONE in suspension Kg | Progressive Kg | Sterile additive solution liters | anti-biotic solution liters | volume liters about |
|---|---|---|---|---|---|
| 0 | 1.250 | 1.25 | 10 | 8 | 700 |
| 4 | | | 10 | | |
| 8 | 1.250 | 2.5 | 10 | | |
| 12 | | | 10 | | |
| 16 | 1.250 | | 10 | | |
| 20 | | | 10 | | |
| 24 | 1.250 | 5 | 10 | 8 | 800 |
| 28 | 1.250 | | 10 | | |
| 32 | 1.250 | | 10 | | |
| 36 | 1.250 | | 10 | | |
| 40 | 1.250 | | 10 | | |
| 44 | 1.250 | | 10 | | |
| 48 | 1.250 | 12.5 | 10 | 8 | 900 |
| 52 | 1.250 | | 10 | | |
| 56 | 1.250 | | 10 | | |
| 60 | 1.250 | | 10 | | |
| 64 | 1.250 | | 10 | | |
| 68 | 1.250 | | 10 | | |
| 72 | 1.250 | 20 | 10 | 8 | 1050 |
| 76 | | | 0 | | |
| 80 | | | | | |
| 84 | | | | | |
| 88 | | | | | |
| 92 | | | | | |
| Total | | | | | |

When bioconversion was complete, the mycelia were separated from the broth by centrifugation in a basket centrifuge. The filtrate was determined by HPLC to contain only 2% of the total quantity of 11α-hydroxycanrenone in the harvest broth, and was therefore eliminated. The mycelia were suspended in ethyl acetate (1000 L) in an extraction tank of 2 m³ capacity. This suspension was heated for one hour under agitation and ethyl acetate reflux conditions, then cooled and centrifuged in a basket centrifuge. The mycelia cake was washed with ethyl acetate (200 L) and thereafter discharged. The steroid rich solvent extract was allowed to stand for one hour for separation of the water phase. The water phase was extracted with a further amount of ethyl acetate solvent (200 L) and then discarded. The combined solvent phases were clarified by centrifugation and placed in a concentrator (500 L geometric volume) and concentrated under vacuum to a residual volume of 100 L. In carrying out the evaporation, the initial charge to the concentrator of combined extract and wash solutions was 100 L, and this volume was kept constant by continual or periodic additions of combined solution as solvent was taken off. After the evaporation step was complete, the still bottoms were cooled to 20° C. and stirred for two hours, then filtered on a Buchner filter. The concentrator pot was washed with ethyl acetate (20 L) and this wash solution was then used to wash the cake on the filter. The product was dried under vacuum for 16 hours at 50° C. Yield of 11α-hydroxycanrenone was 14 kg.

EXAMPLE 4

Lyophilized spores of *Aspergillus ochraceus* NRRL 405 were suspended in a corn steep liquor growth medium (2 ml) having the composition set forth in Table 15:

TABLE 15

Corn Steep Liquor Medium
(Growth Medium for Primary Seed Cultivation)

| | |
|---|---|
| Corn steep liquor | 30 g |
| Yeast extract | 15 g |
| Ammonium phosphate Monobasic | 3 g |
| Glucose (charge after sterilization) | 30 g |
| distilled water, q.s. to 1000 ml | |
| pH as is: 4.6, adjust to pH 6.5 with | |

TABLE 15-continued

Corn Steep Liquor Medium
(Growth Medium for Primary Seed Cultivation)

20% NaOH, distribute 50 ml to 250
ml Erlenmeyer flask sterilize 121° C.
for 20 minutes.

The resulting suspension was used in an inoculum for the propagation of spores on agar plates. Ten agar plates were prepared, each bearing a solid glucose/yeast extract/phosphate/agar growth medium having the composition set forth in Table 16:

TABLE 16

GYPA (Glucose/Yeast Extract/Phosphate
Agar for Plates)

| | |
|---|---|
| Glucose (charge after sterilization) | 10 g |
| Yeast extract | 2.5 g |
| $K_2HPO_4$ | 3 g |
| Agar | 20 g |
| distilled water, q.s. to 1000 ml | |
| adjust pH to 6.5 | |
| sterilize 121° C. for 30 minutes | |

A 0.2 ml aliquot of the suspension was transferred onto the surface of each plate. The plates were incubated at 25° C. for ten days, after which the spores from all the plates were harvested into a sterile cryogenic protective medium having the composition set forth in Table 17:

TABLE 17

GYP/Glycerol (Glucose/Yeast Extract/
Phosphate/Glycerol medium for stock vials)

| | |
|---|---|
| Glucose (charge after sterilization) | 10 g |
| Yeast extract | 2.5 g |
| $K_2HPO_4$ | 3 g |
| Glycerol | 20 g |
| Distilled water, q.s. to 1000 mL | |
| Sterilize at 121° C. for 30 minutes | |

The resulting suspension was divided among twenty vials, with one ml being transferred to each vial. These vials constitute a master cell bank that can be drawn on to produce working cell banks for use in generation of inoculum for bioconversion of canrenone to 11α-hydroxycanrenone. The vials comprising the master cell bank were stored in the vapor phase of a liquid nitrogen freezer at −130° C.

To begin preparation of a working cell bank, the spores from a single master cell bank vial were resuspended in a sterile growth medium (1 ml) having the composition set forth in Table 15. This suspension was divided into ten 0.2 ml aliquots and each aliquot used to inoculate an agar plate bearing a solid growth medium having the composition set forth in Table 16. These plates were incubated for ten days at 25° C. By the third day of incubation, the underside of the growth medium was brown-orange. At the end of the incubation there was heavy production of golden colored spores. The spores from each plate were harvested by the procedure described hereinabove for the preparation of the master cell bank. A total of one hundred vials was prepared, each containing 1 ml of suspension. These vials constituted the working cell bank. The working cell bank vials were also preserved by storage in the vapor phase of a liquid nitrogen freezer at −130° C.

Growth medium (50 ml) having the composition set forth in Table 15 was charged to a 250 ml Erlenmeyer flask. An aliquot (0.5 ml) of working cell suspension was introduced into the flask and mixed with the growth medium. The inoculated mixture was incubated for 24 hours at 25° C. to produce a primary seed culture having a percent packed mycelial volume of approximately 45%. Upon visual inspection the culture was found to comprise pellet-like mycelia of 1 to 2 mm diameter; and upon microscopic observation it appeared as a pure culture.

Cultivation of a secondary seed culture was initiated by introducing a growth medium having the composition set forth in Table 15 into a 2.8 L Fernbach flask, and inoculating the medium with a portion (10 ml) of the primary seed culture of this example, the preparation of which was as described above. The inoculated mixture was incubated at 25° C. for 24 hours on a rotating shaker (200 rpm, 5 cm displacement). At the end of the incubation, the culture exhibited the same properties as described above for the primary seed culture, and was suitable for use in a transformation fermentation in which canrenone was bioconverted to 11α-hydroxycanrenone.

Transformation was conducted in a Braun E Biostat fermenter configured as follows:

| | |
|---|---|
| Capacity: | 15 liters with round bottom |
| Height: | 53 cm |
| Diameter: | 20 cm |
| H/D: | 2.65 |
| Impellers: | 7.46 cm diameter, six paddles 2.2 × 1.4 cm each |
| Impeller spacing: | 65.5, 14.5 and 25.5 cm from bottom of tank |
| Baffles: | four 1.9 × 48 cm |
| Sparger: | 10.1 cm diameter, 21 holes ≈1 mm diameter |
| Temperature control: | provided by means of an external vessel jacket |

Canrenone at a concentration of 20 g/L was suspended in deionized water (4 L) and a portion (2 L) of growth medium having the composition set forth in Table 18 was added while the mixture in the fermenter was stirred at 300 rpm.

TABLE 18

(Growth medium for bioconversion
culture in 10 L fermenter)

| | Quantity | Amount/L |
|---|---|---|
| glucose (charge after sterilization) | 160 g | 20 g |
| peptone | 160 g | 20 g |
| yeast extract | 160 g | 20 g |
| antifoam SAF471 | 4.0 ml | 0.5 ml |
| Canrenone | 160 g | 20 g |
| deionized water q.s. to 7.5 L | | |
| sterilize 121° C. for 30 minutes | | |

The resulting suspension was stirred for 15 minutes, after which the volume was brought up to 7.5 L with additional deionized water. At this point the pH of the suspension was adjusted from 5.2 to 6.5 by addition of 20% by weight NaOH solution, and the suspension was then sterilized by heating at 121° C. for 30 minutes in the Braun E fermenter. The pH after sterilization was 6.3±0.2, and the final volume was 7.0 L. The sterilized suspension was inoculated with a portion (0.5 L) of the secondary seed culture of this example that has been prepared as described above, and the volume brought up to 8.0 L by addition of 50% sterile glucose solution. Fermentation was carried out at a temperature of 28° C. until the PMV reached 50%, then lowered to 26° C., and further lowered to 24° C. when PMV exceeded 50% in order to maintain a consistent PMV below about 60%. Air was introduced through the sparger at a rate of 0.5 vvm based on initial liquid volume and the pressure in the fermenter was maintained at 700 millibar gauge. Agitation began at 600 rpm and was increased stepwise to 1000 rpm as needed to keep the dissolved oxygen content above 30% by volume. Glucose concentration was monitored. After the initial high glucose concentration fell below 1% due to consumption by the fermentation reaction, supplemental glucose was provided via a 50% by weight sterile glucose solution to maintain the concentration in the 0.05% to 1% range throughout the remainder of the batch cycle. Prior to inoculation the pH was 6.3±0.2. After the pH dropped to about 5.3 during the initial fermentation period, it was maintained in the range of 5.5±0.2 for the remainder of the cycle by addition of ammonium hydroxide. Foam was controlled by adding a polyethylene glycol antifoam agent sold under the trade designation SAG 471 by OSI Specialties, Inc.

Growth of the culture took place primarily during the first 24 hours of the cycle, at which time the PMV was about 40%, the pH was about 5.6 and the dissolved oxygen content was about 50% by volume. Canrenone conversion began even as the culture was growing. Concentrations of canrenone and 11α-hydroxycanrenone were monitored during the bioconversion by analyzing daily samples. Samples were extracted with hot ethyl acetate and the resulting sample solution analyzed by TLC and HPLC. The bioconversion was deemed complete when the residual canrenone concentration was about 10% of the initial concentration. The approximate conversion time was 110 to 130 hours.

When bioconversion was complete, mycelial biomass was separated from the broth by centrifugation. The supernatant was extracted with an equal volume of ethyl acetate, and the aqueous layer discarded. The mycelial fraction was resuspended in ethyl acetate using approximately 65 volumes per g canrenone charged to the fermentation reactor. The mycelial suspension was refluxed for one hour under agitation, cooled to about 20° C., and filtered on a Buchner funnel. The mycelial filter cake was washed twice with 5 volumes of ethyl acetate per g of canrenone charged to the fermenter, and then washed with deionized water (1 L) to displace the residual ethyl acetate. The aqueous extract, rich solvent, solvent washing and water washing were combined. The remaining exhausted mycelial cake was either discarded or extracted again, depending on analysis for residual steroids therein. The combined liquid phases were allowed to settle for two hours. Thereafter, the aqueous phase was separated and discarded, and the organic phase concentrated under vacuum until the residual volume was approximately 500 ml. The still bottle was then cooled to about 15° C. with slow agitation for about one hour. The crystalline product was recovered by filtration, and washed with chilled ethyl acetate (100 ml). Solvent was removed from the crystals by evaporation, and the crystalline product dried under vacuum at 50° C.

EXAMPLE 5

Lyophilized spores of *Asoergillus ochraceus* ATCC 18500 were suspended in a corn steep liquor growth medium (2 ml) as described in Example 4. Ten agar plates were prepared, also in the manner of Example 4. The plates were incubated and harvested as described in Example 4 to provide a master cell bank. The vials comprising the master cell bank were stored in the vapor phase of a liquid nitrogen freezer at −130° C.

From a vial of the master cell bank, a working cell bank was prepared as described in Example 4, and stored in the nitrogen freezer at −130° C.

Growth medium (300 mL) having the composition set forth in Table 19 was charged to a 2 L baffled flask. An aliquot (3 mL) of working cell suspension was introduced into the flask. The inoculated mixture was incubated for 20 to 24 hours at 28° C. on a rotating shaker (200 rpm, 5 cm displacement) to produce a primary seed culture having a percent packed mycelial volume of approximately 45%. Upon visual inspection the culture was found to comprise pellet like mycelia of 1 to 2 mm diameter; and upon microscopic observation it appeared as a pure culture.

TABLE 19

Growth medium for primary and secondary seed cultivation

| | Amount/L |
|---|---|
| glucose (charge after sterilization) | 20 g |
| peptone | 20 g |
| Yeast extract | 20 g |
| distilled water q.s. to 1000 mL | |
| sterilize 121° C. for 30 minutes | |

Cultivation of a secondary seed culture was initiated by introducing 8L growth medium having the composition set forth in Table 19 into a 14L glass fermenter. Inoculate the fermenter with 160 mL to 200 mL of the primary seed culture of this example. The preparation of which was as described above.

The inoculated mixture was cultivated at 28° C. for 18–20 hours, 200 rmp agitation, aeration rate was 0.5 vvm. At the end of the propagation, the culture exhibited the same properties as described above for the primary seed.

Transformation was conducted in a 60L fermenter, substantially in the manner described in Example 4, except that the growth medium had the composition set forth in Table 20, and the initial charge of secondary seed culture was 350 mL to 700 mL. Agitation rate was initially 200 rpm, but increased to 500 rpm as necessary to maintain dissolved oxygen above 10% by volume. The approximate bioconversion time for 20 g/L canrenone was 80 to 160 hours.

TABLE 20

Growth Medium for Bioconversion Culture in 60 L Fermenter

| | Quantity | Amount/L |
|---|---|---|
| glucose (charge after sterilization) | 17.5 g | 0.5 g |
| peptone | 17.5 g | 0.5 g |
| yeast extract | 17.5 g | 0.5 g |
| Canrenone (charge as a 20% slurry in sterile water) | 700 g | 20 g |
| deionized water, q.s. to 35 L | | |
| sterilize 121° C. for 30 minutes | | |

EXAMPLE 6

Using a spore suspension from the working cell bank produced in accordance with the method described in Example 4, primary and secondary seed cultures were prepared, also substantially in the manner described in Example 4. Using secondary seed culture produced in this manner, two bioconversion runs were made in accordance with a modified process of the type illustrated in FIG. 1, and two runs were made with the process illustrated in FIG. 2. The transformation growth medium, canrenone addition schedules, harvest times, and degrees of conversion for these runs are set forth in Table 21. Run R2A used a canrenone addition scheme based on the same principle as Example 3, while run R2C modified the Example 3 scheme by making only two additions of canrenone, one at the beginning of the batch, and one after 24 hours. In runs R2B and R2D, the entire canrenone charge was introduced at the beginning of the batch and the process generally carried in the manner described in Example 4, except that the canrenone charge was sterilized in a separate vessel before it was charged to the fermenter and glucose was added as the batch progressed. A Waring blender was used to reduce chunks produced on sterilization. In runs R2A and R2B, canrenone was introduced into the batch in methanol solution, in which respect these runs further differed from the runs of Examples 3 and 4, respectively.

employed to crush the lumps into fine particles, which were successfully converted to product.

EXAMPLE 7

Using a spore suspension from the working cell bank produced in accordance with the method described in Example 4, primary and secondary seed cultures were prepared, also substantially in the manner described in Example 4. The description and results of Example 7 are shown in Table 22. Using secondary seed culture produced in this manner, one bioconversion (R3C) was carried out substantially as described in Example 3, and three bioconversions were carried out in accordance with the process generally described in Example 5. In the latter three runs (R3A, R3B and R3D), canrenone was sterilized in a portable tank, together with the growth medium except for glucose.

TABLE 21

Descriptions of the Initial Canrenone Bioconversion processes

| Run Number | R2A | R2B | R2C | R2D |
|---|---|---|---|---|
| Medium (g/L) | | | | |
| Corn steep liq | 30 | the same as run R2A | 30 | the same as run R2C |
| Yeast extract | 15 | | 15 | |
| $NH_4H_2PO_4$ | 3 | | 3 | |
| Glucose | 15 | | 30 | |
| OSA | 0.5 ml | | 0.5 ml | |
| pH | adjusted to 6.0 with 2.5NNaOH | | adjusted to 6.5 with 2.5NNaOH | |
| Canrenone | 10 g/80 ml MEOH added at 0, 18, 24, 30, 36, 42, 50, 56, 62 and 68 hr. | 80 g/640 ml MEOH added at 0 hr all at once | Sterilized and blended; added at: 0 hr: 25 g 24 hr: 200 g | Sterilized and blended; added at: 0 hr: 200 g |
| Harvest time | 143 hrs. | 166 hrs. | 125 hrs. | 104 hrs. |
| Bioconversion | 45.9% | 95.6% | 98.1% | 95.1% |

In runs R2A and R2B, the methanol concentration accumulated to about 6.0% in the fermentation beer, which was found to be inhibitory to the growth of culture and bioconversion. However, based on the results of these runs, it was concluded that methanol or other water-miscible solvent could serve effectively at lower concentrations to increase the canrenone charge and provide canrenone as a fine particle precipitate providing a large interfacial area for supply of canrenone to the subject to the reaction.

Canrenone proved stable at sterilization temperature (121° C.) but aggregated into chunks. A Waring blender was Glucose was aseptically fed from another tank. The sterilized canrenone suspension was introduced into the fermenter either before inoculation or during the early stage of bioconversion. In run R3B, supplemental sterile canrenone and growth medium was introduced at 46.5. Lumps of canrenone formed on sterilization were delumped through a Waring blender thus producing a fine particulate suspension entering the fermenter. The transformation growth media, canrenone addition schedules, nutrient addition schedules, harvest times, and degrees of conversion for these runs are set forth in Tables 22 and 23.

TABLE 22

Descriptions of Process for Canrenone Bioconversion

| Run Number | R3A | R3B | R3C | R3D |
|---|---|---|---|---|
| Medium (g/L) | | | | |
| Corn steep liq | 30 | the same as run R3A | Peptone: 20 | the same as run R3A |
| Yeast extract | 15 | | Yeast Ext.: 20 | |
| $NH_4H_2PO_4$ | 3 | | Glucose: 20 | |
| Glucose | 15 | | OSA: 3 ml | |
| OSA | 0.5 ml | | | |
| pH | adjusted to 6.5 with 2.5NNaOH | | adjusted to 6.5 with 2.5NNaOH | |
| Canrenone charge at | canrenone was sterilized and blended. BI: 50 g | the same as run R3A BI: 50 g | Non-sterile canrenone: charged by the | The same as run R3A |

TABLE 22-continued

Descriptions of Process for Canrenone Bioconversion

| Run Number | R3A | R3B | R3C | R3D |
|---|---|---|---|---|
| Feedings | 16.5 hrs: 110 g see Table 23 | 16.5 hrs: 110 g 46.5 hrs: 80 g see Table 23 | scheduled listed in Table 23 see Table 23 | BI: 50 g 16.5 hrs: 110 g see Table 23 |
| Harvest time | 118.5 hrs. | 118.5 hrs. | 118.5 hrs. | 73.5 hrs. |
| Bioconversion | 93.7% | 94.7% | 60.0% | 68.0% |

TABLE 23

The Feeding Schedule for Canrenone, Glucose and Growth Medium in the Development Experiment

| | R3C | | | | R3A | R3B | R3D |
|---|---|---|---|---|---|---|---|
| Addition Time hr. | canrenone 200 g/2 L sterile DI g | Glucose 50% solution g | Peptone & Yeast ext. 20 g each in 1L water g | Antibiotics 20 mg kanamycin 20 mg tetracycline 100 mg cefalexin in 50 ml | Canrenone/ Growth Medium see Table 22 g/L | Canrenone/ Growth Medium see Table 22 g/L | Canrenone/ Growth Medium see Table 22 g/L |
| 0 | — | — | — | — | 50 g/0.4 L | 50 g/0.4 L | 50 g/0.4 L |
| 14.5 | 16 | 100 | 25 | 50 ml | — | — | — |
| 16.5 | — | — | — | — | 110 g/1.2 L | 110 g/1.2 L | 110 g/1.2 L |
| 20.5 | 16 | 140 | 25 | — | — | — | — |
| 28.5 | 16 | 140 | 25 | — | — | — | — |
| 34.5 | 16 | 150 | 25 | — | — | — | — |
| 40.5 | 16 | 150 | 25 | 50 ml | — | — | — |
| 46.5 | 880 | 130 | 25 | — | — | 80 g/0.8 L | — |
| 52.5 | 160 | 120 | 25 | — | — | — | — |
| 58.5 | 160 | 150 | 25 | — | — | — | — |
| 64.5 | 160 | 180 | 25 | 50 ml | — | — | — |
| 70.5 | 160 | 140 | 25 | — | — | — | — |

Due to filamentous growth, a highly viscous fermenter broth was seen in all four of the runs of this Example. To overcome obstacles which high viscosity created with respect to aeration, mixing, pH control and temperature control, the aeration rate and agitation speed were increased during these runs. Conversions proceeded satisfactorily under the more severe conditions, but a dense cake formed above the liquid broth surface. Some unreacted canrenone was carried out of the broth by this cake.

EXAMPLE 8

The description and results of Example 8 are summarized in Table 24. Four fermentation runs were made in which 11α-hydroxycanrenone was produced by bioconversion of canrenone. In two of these runs (R4A and R4D), the bioconversion was conducted in substantially the same manner as runs R3A and R3D of Example 6. In run R4C, canrenone was converted to 11α-hydroxycanrenone generally in the manner described in Example 3. In Run R4B, the process was carried out generally as described in Example 4, i.e., with sterilization of canrenone and growth medium in the fermenter just prior to inoculation, all nitrogen and phosphorus nutrients were introduced at the start of the batch, and a supplemental solution containing glucose only was fed into the fermenter to maintain the glucose level as the batch proceeded. In the latter process (run R4B), glucose concentration was monitored every 6 hours and glucose solution added as indicated to control glucose levels in the 0.5 to 1% range. The canrenone addition schedules for these runs are set forth in Table 25.

TABLE 24

Descriptions of the Process Development Experiment of Canrenone Bioconversions

| Run Number | R4A | R4B | R4C | R4D |
|---|---|---|---|---|
| Medium (g/L) | | | | |
| Corn steep liq | 30 | the same as run R4A | Peptone: 20 | the same as run R4A |
| Yeast extract | 15 | | Yeast ext.: 20 | |
| NH4H2PO4 | 3 | | Glucose: 20 | |
| Glucose | 15 | | OSA 3 ml | |

TABLE 24-continued

Descriptions of the Process
Development Experiment of Canrenone Bioconversions

| Run Number | R4A | R4B | R4C | R4D |
|---|---|---|---|---|
| OSA | 0.5 ml | | | |
| pH | adjusted to 6.5 with 2.5NNaOH | | adjusted to 6.5 with 2.5NNaOH | |
| Canrenone charge at | Canrenone was sterilized and blended BI: 40 g 23.5 hrs: 120 g | 160 g canrenone is sterilized in the fermenter | Nonsterile canrenone: charged by the schedule listed in Table 25 | Canrenone was sterilized and blended BI: 40 g 23.5 hrs: 120 g |
| Medium charge | see Table 25 | see Table 25 | see Table 25 | see Table 25 |
| Harvest time | 122 hrs. | 122 hrs. | 122 hrs. | 122 hrs. |
| Bioconversion | 95.6% | 97.6% | 95.4% | 96.7% |

TABLE 25

The Feeding Schedule of Canrenone, Glucose and
Growth Medium in the Development Experiment

| Addition Time hr. | Canrenone 200 g/2 L sterile water g | Glucose 50% solution g | Peptone & Yeast ext. 20 g each in 1 L water g | Antibiotics 20 mg kanamycin 20 mg tetracycline 100 mg cefalexin in 50 ml (added in canrenone slurry) | R4A Growth Medium see Table 24 | R4B Growth Medium see Table 24 | R4D Growth Medium see Table 24 |
|---|---|---|---|---|---|---|---|
| 14 | 600 | 135 | 25 | 50 ml | — | — | — |
| 20 | — | 100 | — | — | — | — | — |
| 23 | — | — | — | — | 120 g/l 2 L | — | 120 g/l 2 L |
| 26 | — | 100 | 25 | — | — | — | — |
| 32 | — | 135 | 25 | — | — | — | — |
| 38 | 500 | 120 | 25 | 50 ml | — | — | — |
| 44 | — | 100 | 25 | — | — | — | — |
| 50 | — | 100 | 25 | — | — | — | — |
| 56 | — | 150 | 25 | — | — | — | — |
| 62 | 500 | 150 | 25 | 50 ml | — | — | — |
| 68 | — | 200 | 25 | — | — | — | — |
| 74 | — | 300 | 25 | — | — | — | — |
| 8- | — | 100 | 25 | — | — | — | — |
| 86 | — | 125 | 25 | — | — | — | — |
| 92 | — | 175 | 25 | — | — | — | — |
| 98 | — | 150 | — | — | — | — | — |
| 104 | — | 175 | — | — | — | — | — |
| 110 | — | 175 | — | — | — | — | — |
| 116 | — | 200 | — | — | — | — | — |

All fermenters were run under high agitation and aeration during most of the fermentation cycle because the fermentation beer had become highly viscous within a day or so after inoculation.

EXAMPLE 9

The transformation growth media, canrenone addition schedules, harvest times, and degrees of conversion for the runs of this Example are set forth in Table 26.

Four bioconversion runs were carried out substantially in the manner described for run R4B of Example 8, except as described below. In run R5B, the top turbine disk impeller used for agitation in the other runs was replaced with a downward pumping marine impeller. The downward pumping action axially poured the broth into the center of the fermenter and reduced cake formation. Methanol (200 ml) was added immediately after inoculation in run RSD. Since canrenone was sterilized in the fermenter, all nutrients except glucose were added at the start of the batch, obviating the need for chain feeding of sources of nitrogen, sources of phosphorus or antibiotics.

TABLE 26

Process Description of the Process
Development Experiment of 10 L Scale Bioconversions

| Run Number | R5A | R5B | R5C | R5D |
|---|---|---|---|---|
| Medium (g/L) | | | | |
| Corn steep liq. | 30 | the same as run R5A | Peptone: 20 | the same as run R5A |
| Yeast Extract | 15 | | Yeast Ext.: 20 | |
| NH$_4$H$_2$PO$_4$ | 3 | | Glucose: 20 | |
| Glucose | 15 | | OSA 3 ml | |
| OSA | 0.5 ml | | | |
| pH | adjusted to 6.5 with 2.5N NaOH | | adjusted to 6.5 with 2.5N NaOH | |
| Canrenone charge | 160 g canrenone sterilized in the fermenter | 160 g canrenone sterilized in the fermenter | 160 g canrenone sterilized in the fermenter | 160 g canrenone sterilized in the fermenter |
| Medium feeding | glucose feeding | glucose feeding | glucose feeding | glucose feeding |
| Harvest time | 119.5 hrs. | 119.5 hrs. | 106 | 119.5 hrs. |
| Bioconversion | 96% | 94.1% | 88.5% | 92.4% |

In order to maintain immersion of the solid phase growing above the liquid surface, growth medium (2 L) was added to each fermenter 96 hours after the beginning of the batch. Mixing problems were not entirely overcome by either addition of growth medium or use of a downward pumping impeller (run R5B) but the results of the runs demonstrated the feasibility and advantages of the process, and indicated that satisfactory mixing could be provided according to conventional practices.

EXAMPLE 10

Three bioconversion runs were carried out substantially in the manner described in Example 9. The transformation growth media, canrenone addition schedules, harvest times, and degrees of conversion for the runs of this Example are set forth in Table 27:

TABLE 27

Process Description of the
Experiment 10 L Scale Bioconversion

| Run Number | R6A | R6B | R6C |
|---|---|---|---|
| Medium (g/L) | | | |
| Corn steep liq. | 30 | the same as run R6A | Peptone: 20 |
| Yeast Extract | 15 | | Yeast Ext.: 20 |
| NH$_4$H$_2$PO$_4$ | 3 | | Glucose: 20 |
| Glucose | 15 | | OSA |
| OSA | 0.5 ml | | 0.5 ml |
| pH | adjusted to 6.5 with 2.5N NaOH | | adjusted to 6.5 with 2.5N NaOH |
| Canrenone charge | 160 g canrenone sterilized in the fermenter | 160 g canrenone sterilized in the fermenter | 160 g canrenone sterilized in the fermenter |
| Medium feeding | glucose feeding; 1.3 L medium and 0.8 L sterile water at 71 hrs. | glucose feeding; 0.5 L medium and 0.5 L sterile water at 95 hrs | glucose feeding; no other addition |
| Harvest time | 120 hrs. | 120 hrs. | 120 hrs. |
| Bioconversion | 95% | 96% | 90% |
| Mass Balance | 59% | 54% | 80% |

Growth medium (1.3 L) and sterile water (0.8 L) were added after 71 hours in run R6A to submerge mycelial cake which had grown above the surface of the liquid broth. For the same purpose, growth medium (0.5 L) and sterile water (0.5 L) were added after 95 hours in run R6B. Material balance data showed that a better mass balance could be determined where cake buildup above the liquid surface was minimized.

EXAMPLE 11

Fermentation runs were made to compare pre-sterilization of canrenone with sterilization of canrenone and growth medium in the transformation fermenter. In run R7A, the process was carried out as illustrated in FIG. 2, under conditions comparable to those of runs R2C, R2D, R3A, R3B, R3D, R4A, and R4D. Run R7B was as illustrated in FIG. 3 under conditions comparable to those of Examples 4, 9 and 10, and run R4B. The transformation growth media, canrenone addition schedules, harvest times, and degrees of conversion for the runs of this Example are set forth in Table 28:

TABLE 28

Process Description of the
Experiment of 10 L Scale Bioconversions

| Run Number | R7A | R7B |
|---|---|---|
| Medium (g/L) | | |
| corn steep liq. | 30 | the same as run R7A |
| Yeast extract | 15 | |
| NH$_4$H$_2$PO$_4$ | 3 | |
| Glucose | 15 | |
| OSA | 0.5 ml | |
| pH | adjusted to 6.5 with 2.5N NaOH | |
| Canrenone charge | 160 g canrenone was sterilized & blended outside the fermenter | 160 g canrenone was sterilized in the fermenter |
| Medium charge | Glucose feeding; canrenone was added with 1.6 L growth medium | Glucose feeding; no other addition |
| Harvest time | 118.5 hrs. | 118.5 hrs. |
| Bioconversion | 93% | 89% |

A mass balance based on the final sample taken from run R7B was 89.5%, indicating that no significant substrate loss or degradation in bioconversion. Mixing was determined to be adequate for both runs.

Residual glucose concentration was above the desired 5–10 gpl control range during the initial 80 hours. Run performance was apparently unaffected by a light cake that accumulated in the head space of both the fermenters.

EXAMPLE 12

Extraction efficiency was determined in a series of 1 L extraction runs as summarized in Table 29. In each of these runs, steroids were extracted from the mycelium using ethyl acetate (1 L/L fermentation volume). Two sequential extractions were performed in each run. Based on RP-HPLC, About 80% of the total steroid was recovered in the first extraction; and recovery was increased to 95% by the second extraction. A third extraction would have recovered another 3% of steroid. The remaining 2% is lost in the supernatant, aqueous phase. The extract was drawn to dryness using vacuum but was not washed with any additional solvent. Chasing with solvent would improve recovery from the initial extraction if justified by process economics.

TABLE 29

Recovery of 11α-Hydroxycanrenone at 1 Liter Extraction
(% of Total)

| Run Number | 1st Extract | 2nd Extract | 3rd Extract | Supernatant |
|---|---|---|---|---|
| R5A | 79% | 16% | 2% | 2% |
| R5A | 84% | 12% | 2% | 2% |
| R4A | 72% | 20% | 4% | 4% |
| R4A | 79% | 14% | 2% | 5% |
| R4B | 76% | 19% | 4% | 1% |
| R4B | 79% | 16% | 3% | 2% |
| R4B | 82% | 15% | 2% | 1% |
| Average | 79% | 16% | 3% | 2% |

Methyl isobutyl ketone (MIBK) and toluene were evaluated as extraction/crystallization solvents for 11α-hydroxycanrenone at the 1 L broth scale. Using the extraction protocol as described hereinabove, both MIBK and toluene were comparable to ethyl acetate in both extraction efficiency and crystallization performance.

EXAMPLE 13

As part of the evaluation of the processes of FIGS. 2 and 3, particle size studies were conducted on the canrenone substrate provided at the start of the fermentation cycle in each of these processes. As described above, canrenone fed to the process of FIG. 1 was micronized before introduction into the fermenter. In this process, the canrenone is not sterilized, growth of unwanted microorganisms being controlled by addition of antibiotics. The processes of FIGS. 2 and 3 sterilize the canrenone before the reaction. In the process of FIG. 2, this is accomplished in a blender before introduction of canrenone into the fermenter. In the process of FIG. 3, a suspension of canrenone in growth medium is sterilized in the fermenter at the start of the batch. As discussed hereinabove, sterilization tends to cause agglomeration of canrenone particles. Because of the limited solubility of canrenone in the aqueous growth medium, the productivity of the process depends on mass transfer from the solid phase, and thus may be expected to depend on the interfacial area presented by the solid particulate substrate which in turn depends on the particle size distribution. These considerations initially served as deterrents to the processes of FIGS. 2 and 3.

Figure 4:
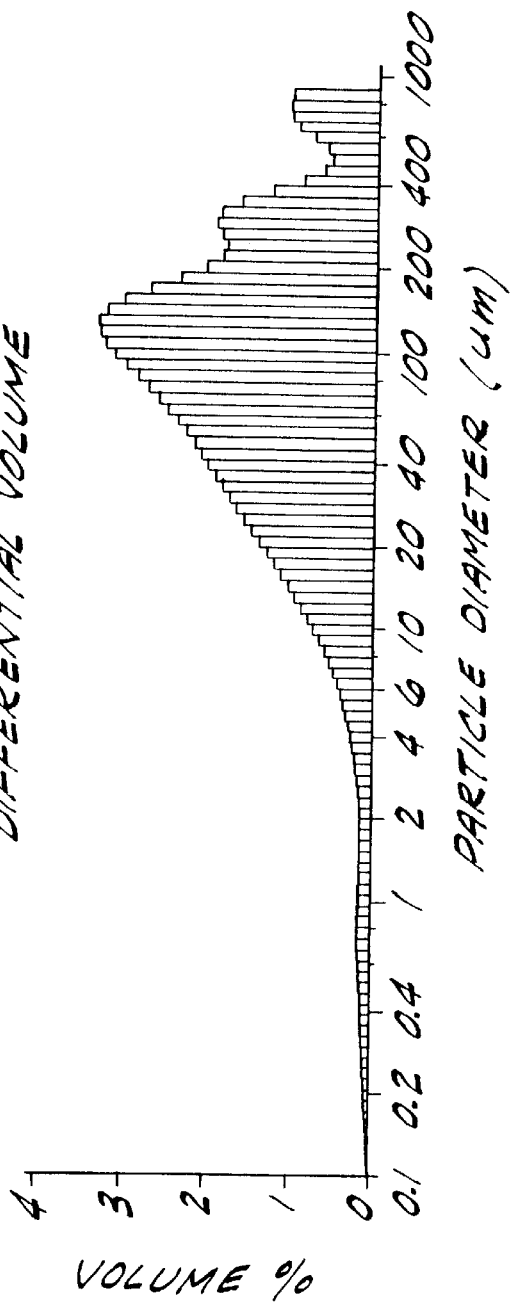
FIG. 4 shows the particle size distribution for canrenone as prepared in accordance with the process of FIG. 2.
Figure 5:
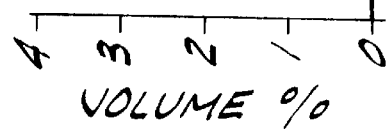
FIG. 5 shows the particle size distribution for canrenone as sterilized in the transformation fermenter in accordance with the process of FIG. 3.

However, agitation in the blender of FIG. 2 and the fermentation tank of FIG. 3, together with the action of the shear pump used for transfer of the batch in FIG. 2, were found to degrade the agglomerates to a particle size range reasonably approximate that of the unsterilized and micronized canrenone fed to the process of FIG. 1. This is illustrated by the particle size distributions for the canrenone as available at the outset of the reaction cycle in each of the three processes. See Table 30 and FIGS. 4 and 5.

TABLE 30

Particle Distributions of Three Different Canrenone Samples

| Sample | 45–125 μ | <180 μ | mean size μ | Run #: % Bioconversion |
|---|---|---|---|---|
| Canrenone shipment | 75% | 95% | — | R3C: 93.1% (120 h) R4C: 96.3% (120 h) |
| Blended Sample | 31.2% | 77.2% | 139.5% | R3A: 94.6% (120 h) R3B: 95.2% (120 h) |
| Sterilized Sample | 24.7% | 65.1% | 157.4% | R4B: 97.6% (120 h) R5B: 93.8% (120 h) |

From the data in Table 30, it will be noted that agitators and shear pump were effective to reduce the average particle size of the sterilized canrenone to the same order of magnitude as the unsterilized substrate, but a significance size difference remained in favor of the unsterilized substrate. Despite this difference, reaction performance data showed that the pre-sterilization processes were at least as productive as the process of FIG. 1. Further advantages may. be realized in the process of FIG. 2 by certain steps for further reducing and controlling particle size, e.g., wet milling of sterilized canrenone, and/or by pasteurizing rather than sterilizing.

EXAMPLE 14

A seed culture was prepared in the manner described in Example 5. At 20 hours, the mycelia in the inoculum fermenter was pulpy with a 40% PMV. Its pH was 5.4 and 14.8 gpl glucose remained unused.

A transformation growth medium (35 L) was prepared having the composition shown in Table 20. In the preparation of feeding medium, glucose and yeast extract were sterilized separately and mixed as a single feed at an initial concentration of 30% by weight glucose and 10% by weight yeast extract. pH of the feed was adjusted to 5.7.

Using this medium, (Table 20), two bioconversion runs were made for the conversion of canrenone to 11α-hydroxycanrenone. Each of the runs was conducted in a 60 L fermenter provided with an agitator comprising one Rushton turbine impeller and two Lightnin' A315 impellers.

Initial charge of the growth medium to the fermenter was 35 L. Micronized and unsterilized canrenone was added to an initial concentration of 0.5%. The medium in the fermenter was inoculated with a seed culture prepared in the manner described in Example 5 at an initial inoculation ratio of 2.5%. Fermentation was carried out at a temperature of 28° C., an agitation rate of 200 to 500 rpm, an aeration rate of 0.5 vvm, and backpressure sufficient to maintain a dissolved oxygen level of at least 20% by volume. The transformation culture developed during the production run was in the form of very small oval pellets (about 1–2 mm). Canrenone and supplemental nutrients were chain fed to the fermenter generally in the manner described in Example 1. Nutrient additions were made every four hours at a ratio of 3.4 g glucose and 0.6 g yeast extract per liter of broth in the fermenter.

Set forth in Table 31 are the aeration rate, agitation rate, dissolved oxygen, PMV, and pH prevailing at stated intervals during each of the runs of this Example, as well as the glucose additions made during the batch. Table 32 shows the canrenone conversion profile. Run R11A was terminated after 46 hours; Run R11B continued for 96 hours. In the latter run, 93% conversion was reached at 81 hours; one more feed addition was made at 84 hours; and feeding then terminated. Note that a significant change in viscosity occurred between the time feeding was stopped and the end of the run.

TABLE 31

| Time | air (1 pm) | rpm | % DO | Backpress | PMV (%) | pH | Gluc cc (g/L) |
|---|---|---|---|---|---|---|---|
| Fermentation R11A ||||||||
| 0.1 | 20 | 200 | 93 | 0 | 2 | 6.17 | 5.8 |
| 7 | 20 | 200 | 85.1 | 0 | 5 | 6.03 | 5.5 |
| 12.4 | 20 | 300 | 50.2 | 0 |  | 5.43 |  |
| 21.8 | 20 | 400 | 25.5 | 0 | 38 | 6.98 | 0 |
| 29 | 20 | 500 | 17 | 0 | 35 | 5.22 |  |
| 30.2 | 20 | 500 | 18.8 | 10 |  | 5.01 |  |
| 31 | 20 | 500 | 79 | 10 |  | 4.81 | 1 |
| 35.7 | 20 | 500 | 100 | 10 | 45 | 5.57 | 0 |
| 46.2 | 20 | 500 | 23 | 6 | 45 | 5.8 | 1 |
| Total glucose: 27.5 g/l ||||||||
| Total yeast extract: 8.75 g/l ||||||||
| Fermentation R11B ||||||||
| 0.1 | 20 | 200 | 92.9 | 0 | 2 | 5.98 | 5.4 |
| 7 | 20 | 200 | 82.3 | 0 | 5 | 5.9 | 5 |
| 12.4 | 20 | 300 | 49.54 | 0 |  | 5.48 |  |
| 21.8 | 20 | 400 | 18 | 0 | 40 | 7.12 | 0 |
| 29 | 20 | 500 | 36.8 | 0 | 35 | 5.1 | 3 |
| 35.7 | 20 | 500 | 94.5 | 10 |  | 4.74 | 0 |
| 46.2 | 20 | 500 | 14.5 | 6 | 45 | 5.32 | 2 |
| 55 | 20 | 500 | 16.7 | 10 |  | 5.31 | 0.5 |
| 58.6 | 20 | 500 | 19.4 | 15 |  | 5.32 | 1 |
| 61.9 | 20 | 500 | 13 | 15 | 40 | 5.36 | 2 |
| 71.7 | 20 | 500 | 13 | 15 | 42 | 5.37 | 0 |
| 81.1 | 20 | 500 | 22.9 | 15 |  | 5.42 | 2.5 |
| 85.6 | 20 | 500 | 22 | 15 | 45 | 5.48 | 1 |
| 97.5 | 20 | 500 | 108 | 15 | 45 | 6.47 | 0 |
| 117.7 | 20 | 500 |  | 15 |  | 7.38 | 0 |
| Total glucose: 63 g/l ||||||||
| Total yeast extract: 14.5 g/l ||||||||

EXAMPLE 15

Various cultures were tested for effectiveness in the bioconversion of canrenone to 11α-canrenone according to the methods generally described above.

A working cell bank of each of *Aspergillus niger* ATCC 11394, *Rhizopus arrhizus* ATCC 11145 and *Rhizopus stolonifer* ATCC 6227b was prepared in the manner described in Example 5. Growth medium (50 ml) having the composition set forth in Table 18 was inoculated with a suspension of spores (1 ml) from the working cell bank and placed in an incubator. A seed culture was prepared in the incubator by fermentation at 26° C. for about 20 hours. The incubator was agitated at a rate of 200 rpm.

Aliquots (2 ml) of the seed culture of each microorganism were used to inoculate transformation flasks containing the growth medium (30 ml) of Table 18. Each culture was used for inoculation of two flasks, a total of six. Canrenone (200 mg) was dissolved in methanol (4 ml) at 36° C., and a 0.5 ml aliquot of this solution was introduced into each of the flasks. Bioconversion was carried out generally under the conditions described in Example 5 with additions of 50% by weight glucose solution (1 ml) each day. After the first 72 hours the following observations were made on the development of mycelia in the respective transformation fermentation flasks:

ATCC 11394—good even growth

ATCC 11145—good growth in first 48 hours, but mycelial clumped into a ball; no apparent growth in last 24 hours;

ATCC 6227b—good growth; mycelial mass forming clumped ball.

Samples of the broth were taken to analyze for the extent of bioconversion. After three days, the fermentation using ATCC 11394 provided conversion to 11α-hydroxycanrenone of 80 to 90%; ATCC 11145 provided a conversion of 50%; and ATCC 6227b provided a conversion of 80 to 90%.

EXAMPLE 16

Using the substantially the method described in Example 15, the additional microorganisms were tested for effective-

TABLE 32

| Sample | Concentrations (g/l) ||| Conversion (%) | Calc OH-can (g/l) | Conv. rates (g/l/h) ||
|---|---|---|---|---|---|---|---|
|  | Time | OH-can | Canren. Total |  |  | Calculated | Measured |
| Fermentation R11A: Canrenone conversion ||||||||
| R11A-0 | 0.10 | 0.00 | 5.41 | 5.41 |  |  |  |
| R11A-7 | 7.00 | 0.18 | 4.89 | 5.07 | 3.58 | 0.18 | 0.03 | 0.03 |
| R11A-22 | 21.80 | 2.02 | 2.12 | 4.14 | 48.75 | 2.44 | 0.15 | 0.12 |
| R11A-29 | 29.00 | 3.67 | 4.14 | 7.81 | 47.03 | 4.48 | 0.28 | 0.23 |
| R11A-36 | 35.70 | 6.68 | 1.44 | 8.12 | 82.27 | 7.74 | 0.49 | 0.45 |
| R11A-46 | 46.20 | 7.09 | 0.41 | 7.51 | 94.48 | 8.59 | 0.08 | 0.04 |
| Fermentation R11B: Canrenone conversion ||||||||
| R11B-0 | 0.1 | 0.00 | 5.60 | 5.60 |  |  |  |  |
| R11B-7 | 7.0 | 0.20 | 4.98 | 5.18 | 3.78 | 0.19 | 0.03 | 0.03 |
| R11B-22 | 21.8 | 2.51 | 2.46 | 4.97 | 50.49 | 2.52 | 0.16 | 0.16 |
| R11B-29 | 29.0 | 4.48 | 16.99 | 21.47 | 20.87 | 4.69 | 0.30 | 0.27 |
| R11B-36 | 35.7 | 8.18 | 10.35 | 18.53 | 44.16 | 9.70 | 0.75 | 0.55 |
| R11B-55 | 55.0 | 17.03 | 13.20 | 30.23 | 56.33 | 19.50 | 0.32 | 0.36 |
| R11B-59 | 58.6 | 20.80 | 11.73 | 32.53 | 63.95 | 21.97 | 0.69 | 1.05 |
| R11B-62 | 61.9 | 22.19 | 8.62 | 30.81 | 72.02 | 24.50 | 0.77 | 0.42 |
| R11B-72 | 71.7 | 26.62 | 3.61 | 30.23 | 88.06 | 29.46 | 0.51 | 0.45 |
| R11B-81 | 81.1 | 27.13 | 2.05 | 29.18 | 92.97 | 30.32 | 0.09 | 0.05 |
| R11B-86 | 85.6 | 26.87 | 2.02 | 28.88 | 93.02 | 30.11 | −0.04 | −0.06 |
| R11B-97 | 97.5 | 23.95 | 1.71 | 25.66 | 93.34 | 30.22 | 0.01 | −0.25 |
| R11B-118 | 117.7 | 24.10 | 1.68 | 25.79 | 93.47 | 30.26 | 0.00 | 0.01 | ness in the conversion of canrenone to 11α-hydroxycanrenone. The organisms tested and the results of the tests are set forth in Table 33:

TABLE 33

Cultures tested for Bioconversion of canrenone to 11 alpha-hydroxy-canrenone

| Culture | ATTC # | media[1] | results | | approximate conversion |
|---|---|---|---|---|---|
| Rhizopus oryzae | 1145 | CSL | + | 50% | — |
| Rhizopus stolonifer | 6227b | CSL | + | 80–90% | — |
| Aspergillus nidulans | 11267 | CSL | + | 50% | 80% |
| Aspergillus niger | 11394 | CSL | + | 80–90% | — |
| Aspergillus ochraceus | NRRL 405 | CSL | + | | 90% |
| Aspergillus ochraceus | 18500 | CSL | + | | 90% |
| Bacillus subtilis | 31028 | P & CSL | – | 0% | 0% |
| Bacillus subtilis | 31028 | CSL | – | 0% | 0% |
| Bacillus sp. | 31029 | P & CSL | + | 5% | 80%* |
| Bacillus sp. | 31029 | CSL | – | 0% | * |
| Bacillus megaterium | 14945 | P & CSL | + | 5% | 10%* |
| Bacillus megaterium | 14945 | CSL | + | 5% | 10%* |
| Trichothecium roseum | 12519 | CSL | + | 80%* | 90%* |
| Trichothecium roseum | 8685 | CSL | + | 80%* | 90*% |
| Streptomyces fradiae | 10745 | CSL | + | <5% | <10% |
| Streptomyces fradiae | 10745 | TSB | – | * | * |
| Streptomyces lavendulae | 13664 | CSL | – | 0% | * |
| Streptomyces lavendulae | 13664 | TSB | – | 0% | 0% |
| Nocardiodes simplex | 6946 | BP | – | 0% | 0% |
| Nocardiodes simplex | 13260 | BP | – | * | * |
| Pseudomonas sp. | 14696 | BP | – | * | * |
| Pseudomonas sp. | 14696 | CSL | + | <5% | <10% |
| Pseudomonas sp. | 14696 | TSB | – | 0% | * |
| Pseudomonas sp. | 13261 | BP | + | * | <10% |
| Pseudomonas cruciviae | 13262 | BP | | # | <10% |
| Pseudomonas putida | 15175 | BP | – | 0% | 0% |

*formation of other unidentified products
[1]Media: CSL - corn steep liquor; TSB - tryptic soy broth; P & CSL - peptone and acorn steep liquor; BP - beef extract and peptone.

EXAMPLE 17

Various microorganisms were tested for effectiveness in the conversion of canrenone to 9α-hydroxycanrenone. Fermentation media for the runs of this Example were prepared as set forth in Table 34:

TABLE 34

| Soybean Meal: | |
|---|---|
| dextrose | 20 g |
| soybean meal | 5 g |
| NaCl | 5 g |
| yeast extract | 5 g |
| KH$_2$PO$_4$ | 5 g |
| water | to 1 L |
| pH | 7.0 |
| Peptone/yeast extract/glucose: | |
| glucose | 40 g |
| bactopeptone | 10 g |
| yeast extract | 5 g |
| water | to 1 L |
| Mueller-Hinton: | |
| beef infusion | 300 g |
| casamino acids | 17.5 g |

TABLE 34-continued

| starch | 1.5 g |
|---|---|
| water | to 1 L |

Fungi were grown in soybean meal medium and in peptone-yeast extract glucose; atinomycetes and eubacteria were grown in soybean meal (plus 0.9% by weight Na formate for biotransformations) and in Mueller-Hinton broth.

Starter cultures were inoculated with frozen spore stocks (20 ml soybean meal in 250 ml Erlenmayer flask). The flasks were covered with a milk filter and bioshield. Starter cultures (24 or 48 hours old) were used to inoculate metabolism cultures (also 20 ml in 250 ml Erlenmeyer flask)—with a 10% to 15% crossing volume—and the latter incubated for 24 to 48 hours before addition of steroid substrate for the transformation reaction.

Canrenone was dissolved/suspended in methanol (20 mg/ml), filter sterilized, and added to the cultures to a final concentration of 0.1 mg/ml. All transformation fermentation flasks were shaken at 250 rpm (2" throw) in a controlled temperature room at 26° C. and 60% humidity.

Biotransformations were harvested at 5 and 48 hours, or at 24 hours, after addition of substrate. Harvesting began with the addition of ethyl acetate (23 ml) or methylene chloride to the fermentation flask. The flasks were then shaken for two minutes and the contents of each flask poured into a 50 ml conical tube. To separate the phases, tubes were centrifuged at 4000 rpm for 20 minutes in a room temperature unit. The organic layer from each tube was transferred to a 20 ml borosilicate glass vial and evaporated in a speed vac. Vials were capped and stored at –20° C.

To obtain material for structure determination, biotransformations were scaled up to 500 ml by increasing the number of shake flask fermentations to 25. At the time of harvest (24 or 48 hours after addition of substrate), ethyl acetate was added to each flask individually, and the flasks were capped and put back on the shaker for 20 minutes. The contents of the flasks were then poured into polypropylene bottles and centrifuged to separate the phases, or into a separatory funnel in which phases were allowed to separate by gravity. The organic phase was dried, yielding crude extract of steroids contained in the reaction mixture.

Reaction product was analyzed first by thin layer chromatography on silica gel (250 μm) fluorescence backed plates (254 nm). Ethyl acetate (500 μL was added to each vial containing dried ethyl acetate extract from the reaction mixture. Further analyses were conducted by high performance liquid chromatography and mass spectrometry. Plates were developed in a 95:5 v/v chloroform/methanol medium.

Further analysis was conducted by high performance liquid chromatography and mass spectrometry. A waters HPLC with Millennium software, photodiode array detector and autosampler was used. Reversed phase HPLC used a waters NovaPak C-18 (4 μm particle size) RadialPak 4 mmcartridge. The 25 minute linear solvent gradient began with the column initialized in water:acetonitrile (75:25), and ended at water:acetonitrile (25:75). This was followed by a three minute gradient to 100% acetonitrile and 4 minutes of isocratic wash before column regeneration in initial conditions.

For LC/MS, ammonium acetate was added to both the acetonitrile and water phases at a concentration of 2 nM. Chromatography was not significantly affected. Eluant from the column was split 22:1, with the majority of the material directed to the PDA detector. The remaining 4.5% of the material was directed to the electrospray ionizing chamber of an Sciex API III mass spectrometer. Mass spectrometry was accomplished in positive mode. An analog data line from the PDA detector on the HPLC transferred a single wave length chromatogram to the mass spectrometer for coanalysis of the UV and MS data.

Mass spectrometric fragmentation patterns proved useful in sorting from among the hydroxylated substrates. The two expected hydroxylated canrenones, 11α-hydroxy- and 9α-hydroxy, lost water at different frequencies in a consistent manner which could be used as a diagnostic. Also, the 9α-hydroxycanrenone formed an ammonium adduct more readily than did 11α-hydroxycanrenone. Set forth in Table 35 is a summary of the TLC, HPLC/UV and LC/MS data for canrenone fermentations, showing which of the tested microorganism were effective in the bioconversion of canrenone to 9α-hydroxycanrenone. Of these, the preferred microorganism was *Corynespora cassiicola* ATCC 16718.

TABLE 35

Summary of TLC, HPLC/UV, and LC/MS Data for Canrenone Fermentations

| | Evidence for 9αOH-canrenone | | |
|---|---|---|---|
| Culture | TLC spot at 9αQH-AD | HPLC-peak at 9αOH-canrenone w/UV | MS: 357 (M + H) 339 (−H$_2$O) & 375 (+NH$_4$) |
| *Absidia coerula* ATCC 6647 | n | y | y/n |
| *Absidia glauca* ATCC 22752 | n | | |
| *Actinomucor elegans* ATCC 6476 | tr | y | tr |
| *Aspergillus flavipes* ATCC 1030 | tr | | |
| *Aspergillus fumigatus* ATCC 26934 | tr | y | n |
| *Aspergillus nidulans* ATCC 11267 | tr | y | y |
| *Aspergillus niger* ATCC 16888 | n | y | y |
| *Aspergillus niger* ATCC 26693 | n | y | n |
| *Aspergillus ochraceus* ATCC 18500 | n | y | n |
| *Bacterium cyclo-oxydans* (Searle) ATCC 12673 | n | tr | n |
| *Beauveria bassiana* ATCC 7159 | tr | y | y |
| *Beauveria bassiana* ATCC 13144 | y | y | y |
| *Botryosphaeria obtusa* IMI 038560 | y | tr | tr |
| *Calonectria decora* ATCC 14767 | n | tr | y |
| *Chaetomium cochliodes* ATCC 10195 | tr | tr | y/n |
| *Comomonas testosteroni* (Searle) ATCC 11996 | tr | tr | n |
| *Corynespora cassiicola* ATCC 16718 | y | y | y |
| *Cunninghamella blakesleana* ATCC 8688a | y | y | y |
| *Cunninghamella echinulata* ATCC 3655 | y | y | y |
| *Cunninghamella elegans* ATCC 9245 | y | y | y |
| *Curcularia clavata* ATCC 22921 | n | y | y/n |
| *Curvularia lunata* ATCC 12071 | y | n | n |

TABLE 35-continued

Summary of TLC, HPLC/UV, and LC/MS Data for Canrenone Fermentations

| | Evidence for 9αOH-canrenone | | |
|---|---|---|---|
| Culture | TLC spot at 9αQH-AD | HPLC-peak at 9αOH-canrenone w/UV | MS: 357 (M + H) 339 (−H$_2$O) & 375 (+NH$_4$) |
| *Cylindrocarpon radicicola* (Searle) ATCC 11011 | tr | n | n |
| *Epicoccum humucola* ATCC 12722 | y | y | y |
| *Epicoccum oryzae* ATCC 12724 | tr | tr | tr |
| *Fusarium oxysporum* ATCC 7601 | tr | | |
| *Fusarium oxysporum* f. sp. *cepae* ATCC 11171 | n | | |
| *Gibberella fujikuroi* ATCC 14842 | tr | y | y |
| *Gliocladium deliquescens* ATCC 10097 | y | tr | tr |
| *Gongronella butieri* ATCC 22822 | y | y UV? | y |
| *Hypomyces chrysospermus* Tul. IMI 109891 | y | y | y |
| *Lipomyces lipofer* ATCC 10792 | n | | |
| *Melanospora ornata* ATCC 26180 | tr | n | n |
| *Mortierella isabellinay* ATCC 42613 | y | y | n |
| *Mucor grisco-cyanus* ATCC 1207a | n | | |
| *Mucor mucedo* ATCC 4605 | tr | y | y |
| *Mycobacterium fortuitumn* ATCC 6842 | | | |
| *Myrothecium verrucaria* ATCC 9095 | tr | tr | y |
| *Nocardia aurentia* (Searle) ATCC 12674 | n | tr | n |
| *Nocardia cancicruria* (Searle) | y | y | n |
| *Nocardia corallina* ATCC 19070 | n | | |
| *Paecilomyces carneus* ATCC 46579 | n | y | n |
| *Penicillium chrysogenum* ATCC 9480 | n | | |
| *Penicillium patulum* ATCC 24550 | y | y | y/n |
| *Penicillium purpurogenum* ATCC 46581 | tr | y | y |
| *Pithomyces atro-olivaceus* ATCC 6651 | tr | y | tr |
| *Pithomyces cynodontis* ATCC 26150 | n | tr | tr |
| *Phycomyces blakesleeanus* | y | y | y/n |
| *Pycnosporium* sp. ATCC 12231 | y | y | y/n |
| *Rhizopogon* sp. | | | |
| *Rhizopus arrhizus* ATCC 11145 | tr | y | n |
| *Rhizopus stolonifer* ATCC 6227b | n | | |
| *Rhodococcus equi* ATCC 14887 | n | tr | n |
| *Rhodococcus equi* ATCC 21329 | tr | tr | n |
| *Rhodococcus* sp. | n | n | n |
| *Rhodococcus rhodochrous* ATCC 19150 | n | tr | n |
| *Saccharopolyspora erythaea* ATCC 11635 | y | y | y |

TABLE 35-continued

Summary of TLC, HPLC/UV, and LC/MS
Data for Canrenone Fermentations

| | Evidence for 9αOH-canrenone | | |
|---|---|---|---|
| Culture | TLC spot at 9αQH-AD | HPLC-peak at 9αOH-canrenone w/UV | MS: 357 (M + H) 339 (−H$_2$O) & 375 (+NH$_4$) |
| Sepedonium ampullosporum IMI 203033 | n | n | n |
| Sepedonium chrysospermum ATCC 13378 | n | | |
| Septomyxa affinis ATCC 6737 | n | y UV? | y/n |
| Stachylidium bicolor ATCC 12672 | y | y | y/n |
| Streptomyces californicus ATCC 15436 | n | | |
| Streptomyces cinereocrocatus ATCC 3443 | n | | |
| Streptomyces coelicolor ATCC 10147 | n | | |
| Streptomyces flocculus ATCC 25453 | | | |
| Streptomyces fradiae ATCC 10745 | n | | |
| Streptomyces griseus subsp. griseus ATCC 13968 | n | | |
| Streptomyces griseus ATCC 11984 | n | | |
| Streptomyces hydrogenahs ATCC 19631 | n | | |
| Streptomyces hygroscopicus ATCC 27438 | y | y | y |
| Streptomyces lavendulae Panlab 105 | n | | |
| Streptomyces paucisporogenes ATCC 25489 | n | | |
| Streptomyces purpurascens ATCC 25489 | n | tr | tr |
| Streptomyces roseochromogenes ATCC 13400 | | | |
| Streptomyces spectabilis ATCC 27465 | n | | |
| Stysanus microsporus ATCC 2833 | | | |
| Syncephalastrum racemosum ATCC 18192 | n | | |
| Thamnidium elegans ATCC 18191 | | | |
| Thamnostylum piriforme ATCC 8992 | y | tr | y |
| Thielavia terricolan ATCC 13807 | | | n |
| Trichoderma viride ATCC 26802 | n | | |
| Trichothecium roseum ATCC 12543 | tr | y | y/n |
| Verticillium theobromae ATCC 12474 | y | tr | tr |

EXAMPLE 18

Various cultures were tested for effectiveness in the bioconversion of androstendione to 11α-hydroxyandrostendione according to the methods generally described above.

A working cell bank of each of *Aspergillus ochraceus* NRRL 405 (ATCC 18500); *Aspergillus niger* ATCC 11394; *Aspergillus nidulans* ATCC 11267; *Rhizopus orvzae* ATCC 11145; *Rhizopus stolonifer* ATCC 6227b; *Trichothecium roseum* ATCC 12519 and ATCC 8685 was prepared essentially in the manner described in Example 4. Growth medium (50 ml) having the composition set forth in Table 18 was inoculated with a suspension of spores (1 ml) from the working cell bank and placed in an incubator. A seed culture was prepared in the incubator by fermentation at 26° C. for about 20 hours. The incubator was agitated at a rate of 200 rpm.

Aliquots (2 ml) of the seed culture of each microorganism were used to inoculate transformation flasks containing the growth medium (30 ml) of Table 15. Each culture was used for inoculation of two flasks, a total of 16. Androstendione (300 mg) was dissolved in methanol (6 ml) at 36° C., and a 0.5 ml aliquot of this solution was introduced into each of the flasks. Bioconversion was carried out generally under the conditions described in Example 6 for 48 hours. After 48 hours samples of the broth were pooled and extracted with ethyl acetate as in Example 17. The ethyl acetate was concentrated by evaporation, and samples were analyzed by thin layer chromatography to determine whether a product having a chromatographic mobility similar to that of 11α-hydroxy-androstendione standard (Sigma Chemical Co., St. Louis) was present. The results are shown in Table 36. Positive results are indicated as "+".

TABLE 36

Bioconversion of androstendione to 11 alpha-hydroxy-androstendione

| Culture | ATTC# | media | TLC results |
|---|---|---|---|
| Rhizopus oryzae | 11145 | CSL | + |
| Rhizopus stolonifer | 6227b | CSL | + |
| Aspergillus nidulans | 11267 | CSL | + |
| Aspergillus niger | 11394 | CSL | + |
| Aspergillus ochraceus | NRRL 405 | CSL | + |
| Aspergillus ochraceus | 18500 | CSL | + |
| Trichothecium roseum | 12519 | CSL | + |
| Trichothecium roseum | 8685 | CSL | + |

The data in Table 36 demonstrate that each of listed cultures was capable of producing a compound from androstendione having the same Rf value as that of the 11α-hydroxyandrostendione standard.

*Aspergillus ochraceus* NRRL 405 (ATCC 18500) was retested by the same procedure described above, and the culture products were isolated and purified by normal phase silica gel column chromatography using methanol as the solvent. Fractions were analyzed by thin layer chromatography. TLC plates were Whatman K6F silica gel 60Å, 10×20 size, 250μ thickness. The solvent system was methanol:chloroform, 5:95, v/v. The crystallized product and 11α-hydroxyandrostendione standard were both analyzed by LC-MS and NMR spectroscopy. Both compounds yielded similar profiles and molecular weights.

EXAMPLE 19

Various microorganisms were tested for effectiveness in the conversion of mexrenone to 11β-hydroxymexrenone. Fermentation media for this example were prepared as described in Table 34.

The fermentation conditions and analytical methods were the same as those in Example 17. TLC plates and the solvent system were as described in Example 18. The rationale for chromatographic analysis is as follows: 11α-hydroxymexrenone and 11α-hydroxycanrenone have the same chromatographic mobility. 11α-hydroxycanrenone and 9α-hydroxycanrenone exhibit the same mobility pattern as 11α-hydroxyandrostendione and 11β-hydroxyandrostendione. Therefore, 11β-hydroxymexrenone should have the same mobility as 9α-hydroxycanrenone. Therefore, compounds extracted from the growth media were run against 9α-hydroxycanrenone as a standard. The results are shown in Table 36.

TABLE 37

Summary of TLC Data for
11β-hydroxymexrenone Formation
from Mexrenone

| Microorganism | Medium[1] | Spot Character[2] |
|---|---|---|
| Absidia coerula ATCC 6647 | M, S | strong |
| Aspergillus niger ATCC 16888 | S, P | faint (S) ? (P) |
| Beauveria bassiana ATCC 7159 | P | strong |
| Beauveria bassiana ATCC 13144 | S, P | ?, ? |
| Botryosphaeria obtusa IMI 038560 | | faint |
| Cunninghamella | | |
| blakesleeana ATCC 8688a | S, P | strong |
| echinulata ATCC 3655 | S, P | strong |
| elegans ATCC 9245 | S, P | strong |
| Curvularia lunata ATCC 12017 | S | strong |
| Gongronella butleri ATCC 22822 | S, P | strong |
| Penicillium patulum ATCC 24550 | S, P | strong |
| Penicillium purpurogenum ATCC 46581 | S, P | strong |
| Pithomyces atro-olivaceus IFO 6651 | S, P | faint |
| Rhodococcus equi ATCC 14887 | M | faint |
| Saccharopolyspora erythaea ATCC 11635 | M, SF | faint |
| Streptomyces hygroscopicus ATCC 27438 | M, SF | strong |
| Streptomyces purpurascens ATCC 25489 | M, SF | faint |
| Thamnidium elegans ATCC 18191 | S, P | faint |
| Thamnostylum piriforme ATCC 8992 | S, P | faint |
| Trichothecium roseum ATCC 12543 | P, S | faint (P) ? (S) |

[1]M = Mueller-Hinton
P = PYG (peptone/yeast extract/glucose)
S = soybean meal
SF = soybean meal plus formate
[2]? = questionable difference from no substrate control These data suggest that the majority of the organisms listed in this table produce a product similar or identical to 11β-hydroxymexrenone from mexrenone.

EXAMPLE 20

Scheme 1: Step 1: Preparation of 5'R(5'α), 7'β-20'-Aminchexadecahydro-11'β-hydroxy-10'α,13'α-dimethyl-3',5-dioxospiro[furan-2(3H),17'α(5'H)-[7,4]metheno[4H][cyclopenta[a]phenanthrene]-5'-carbonitrile.

Into a 50 gallon glass-line reactor was charged 61.2 L (57.8 kg) of DMF followed by 23.5 Kg of 11-hydroxycanrenone 1 with stirring. To the mixture was added 7.1 kg of lithium chloride. The mixture was stirred for 20 minutes and 16.9 kg of acetone cyanohydrin was charged followed by 5.1 kg of triethylamine. The mixture was heated to 85° C. and maintained at this temperature for 13–18 hours. After the reaction 353 L of water was added followed by 5.6 kg of sodium bicarbonate. The mixture was cooled to 0° C., transferred to a 200 gallon glass-lined reactor with quenched with 130 kg of 6.7% sodium hypochlorite solution slowly. The product was filtered and washed with 3×40 L portions or water to give 21.4 kg of the product enamine.

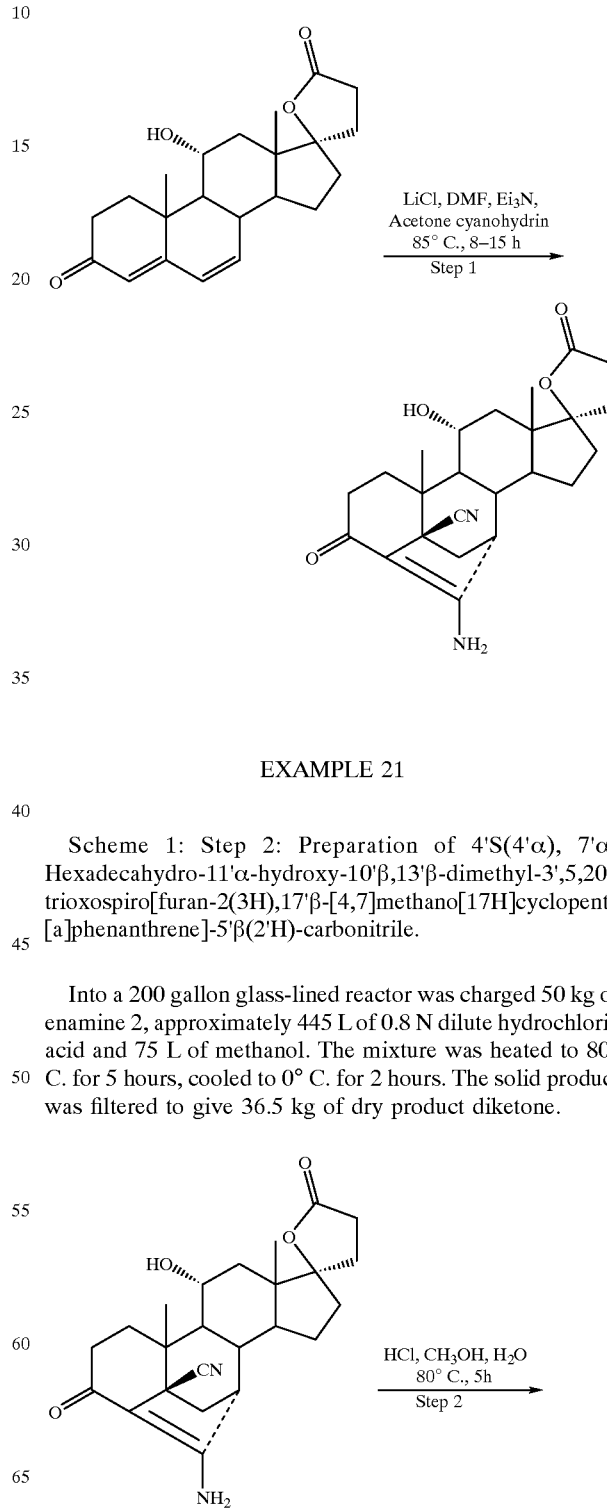

EXAMPLE 21

Scheme 1: Step 2: Preparation of 4'S(4'α), 7'α-Hexadecahydro-11'α-hydroxy-10'β,13'β-dimethyl-3',5,20'-trioxospiro[furan-2(3H),17'β-[4,7]methano[17H]cyclopenta[a]phenanthrene]-5'β(2'H)-carbonitrile.

Into a 200 gallon glass-lined reactor was charged 50 kg of enamine 2, approximately 445 L of 0.8 N dilute hydrochloric acid and 75 L of methanol. The mixture was heated to 80° C. for 5 hours, cooled to 0° C. for 2 hours. The solid product was filtered to give 36.5 kg of dry product diketone.

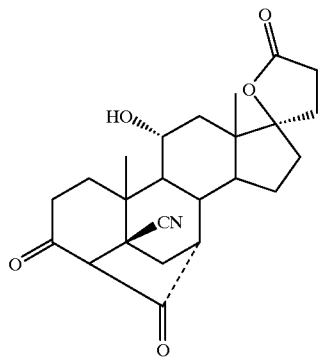

EXAMPLE 22

Scheme 1: Step 3A: Preparation of Methyl Hydrogen 11α,17α-Dihydroxy-3-oxopregn-4-ene-7α,21-dicarboxylate, γ-Lactone.

A 4-neck 5-L bottom flask was equipped with mechanical stirrer, pressure equalizing addition funnel with nitrogen inlet tube, thermometer and condenser with bubbler. The bubbler was connected via tygon tubing to two 2-L traps, the first of which was empty and placed to prevent back-suction of the material in the second trap (1 L of concentrated sodium hypochlorite solution) into the reaction vessel. The diketone 3 (79.50 g; [weight not corrected for purity, which was 85%]) was added to the flask in 3 L methanol. A 25% methanolic sodium methoxide solution (64.83 g) was placed in the funnel and added dropwise, with stirring under nitrogen, over a 10 minute period. After the addition was complete, the orangish yellow reaction mixture was heated to reflux for 20 hours. After this period, 167 mL of 4 N HCl was added (Caution: HCN evolution at this point!) dropwise through the addition funnel to the still refluxing reaction mixture. The reaction mixture lightened in color to a pale golden orange. The condenser was then replaced with a take-off head and 1.5 L of methanol was removed by distillation while 1.5 L of water was simultaneously added to the flask through the funnel, in concert with the distillation rate. The reaction mixture was cooled to ambient temperature and extracted twice with 2.25 L aliquots of methylene chloride. The combined extracts were washed successively with 750 mL aliquots of cold saturated NaCl solution, 1N NaOH and again with saturated NaCl. The organic layer was dried over sodium sulfate overnight, filtered and reduced in volume to ~250 mL in vacuo. Toluene (300 mL) was added and the remaining methylene chloride was stripped under reduced pressure, during which time the product began to form on the walls of the flask as a white solid. The contents of the flask were cooled overnight and the solid was removed by filtration. It was washed with 250 mL toluene and twice with 250 mL aliquots of ether and dried on a vacuum funnel to give 58.49 g of white solid was 97.3% pure by HPLC. On concentrating the mother liquor, an additional 6.76 g of 77.1% pure product was obtained. The total yield, adjusted for purity, was 78%.

EXAMPLE 23

Scheme 1: Step 3B: Conversion of Methyl Hydrogen 11α,17α-Dihydroxy-3-oxopregn-4-ene-7α,21-dicarboxylate, γ-Lactone to Methyl Hydrogen 17α-Hydroxy-11α-(methylsulfonyl)oxy-3-oxopregn-4-ene-7α,21-dicarboxylate, γ-Lactone.

A 5-L four neck flask was equipped as in the above example, except that no trapping system was installed beyond the bubbler. A quantity of 138.70 g of the hydroxyester was added to the flask, followed by 1425 mL methylene chloride, with stirring under nitrogen. The reaction mixture was cooled to −5° C. using a salt/ice bath. Methanesulfonyl chloride (51.15 g, 0.447 mole) was added rapidly, followed by the slow dropwise addition of triethylamine (54.37 g) in 225 mL methylene chloride. Addition, which required ~30 minutes, was adjusted so that the temperature of the reaction never rose about 5° C. Stirring was continued for 1 hour post-addition, and the reaction contents were transferred to a 12-L separatory funnel, to which was added 2100 mL methylene chloride. The solution was washed successively with 700 mL aliquots each of cold 1N HCl, 1N NaOH, and saturated aqueous NaCl solution. The aqueous washes were combined and back-extracted with 3500 mL methylene chloride. All of the organic washes were combined in a 9-L jug, to which was added 500 g neutral alumina, activity grade II, and 500 g anhydrous sodium sulfate. The contents of the jug were mixed well for 30 minutes and filtered. The filtrate was taken to dryness in vacuo to give a gummy yellow foam. This was dissolved in 350 mL methylene chloride and 1800 mL ether was added dropwise with stirring. The rate of addition was adjusted so that about one-half of the ether was added over 30 minutes. After about 750 mL had been added, the product began to separate as a crystalline solid. The remaining ether was added in 10 minutes. The solid was removed by filtration, and the filter cake was washed with 2 L of ether and dried in a vacuum oven at 50° C. overnight, to give 144.61 g (88%) nearly white solid, m.p. 149°–150° C. Material prepared in this fashion is typically 98–99% pure by HPLC (area %). In one run, material having a melting point of 153°–153.5° C. was obtained, with a purity, as determined by HPLC area, of 99.5%.

EXAMPLE 24

Scheme 1: Step 3C: Method A: Preparation of Methyl Hydrogen 17α-Hydroxy-3-oxopregna-4,9(11)-diene-7α,21-dicarboxylate, γ-Lactone.

A 1-L four neck flask was equipped as in the second example. Formic acid (250 mL) and acetic anhydride (62 mL) were added to the flask with stirring under nitrogen. Potassium formate (6.17 g) was added and the reaction mixture was heated with an oil bath to an internal temperature of 40° C. (this was later repeated at 70° C. with better results) for 16 hours. After 16 hours, the mesylate 5 was added and the internal temperature was increased to 100° C. Heating and stirring were continued for 2 hours, after which the solvent was removed in vacuo on a rotavap. The residue was stirred with 500 mL ice water for fifteen minutes, then extracted twice with 500 mL aliquots of ethyl acetate. The organic phases were combined and washed successively with cold 250 mL aliquots of saturated sodium chloride solution (two times), 1 N sodium hydroxide solution, and again with saturated sodium chloride. The organic phase was then dried over sodium sulfate, filtered and taken to dryness in vacuo to give a yellowish white foam, which pulverized to a glass when touched with a spatula. The powder that formed, 14.65 g analyzed as a mixture of 82.1% 6 7.4% 8 and 5.7% 9 (by HPLC area %).

EXAMPLE 25

Scheme 1: Step 3C: Method B: Preparation of Methyl Hydrogen 17α-Hydroxy-3-oxopregna-4,9(11)-diene-7α,21-dicarboxylate, γ-Lactone.

A 5-L four neck flask was equipped as in the above example and 228.26 g acetic acid and 41.37 g sodium acetate were added with stirring under nitrogen. Using an oil bath, the mixture was heated to an internal temperature of 100° C. The mesylate (123.65 g) was added, and heating was continued for thirty minutes. At the end of this period, heating was stopped and 200 mL of ice water was added. The temperature dropped to 40° C. and stirring was continued for 1 hour, after which the reaction mixture was poured slowly into 1.5 L of cold water in a 5-L stirred flask. The product separated as a gummy oil. The oil was dissolved in 1 L ethyl acetate and washed with 1 L each cold saturated sodium chloride solution, 1 N sodium hydroxide, and finally-saturated sodium chloride again. The organic phase was dried over sodium sulfate and filtered. The filtrate was taken to dryness in vacuo to give a foam which collapsed to a gummy oil. This was triturated with ether for some time and eventually solidified. The solid was filtered and washed with more ether to afford 79.59 g of a yellow white solid. This consisted of 70.4% of the desired $\Delta^{9,11}$ enester 6, 12.3% of the $\Delta^{11,12}$ enester 8, 10.8% of the 7-α,9-α-lactone 9 and 5.7% unreacted 5.

EXAMPLE 26

Scheme 1: Step 3D: Synthesis of Methyl Hydrogen 9,11α-Epoxy-17α-hydroxy-3-oxopregn-4-ene-7α,21-dicarboxylate, γ-Lactone.

A 4-neck jacketed 500 mL reactor was equipped with mechanical stirrer, condenser/bubbler, thermometer and addition funnel with nitrogen inlet tube. The reactor was charged with 8.32 g of the crude enester in 83 mL methylene chloride, with stirring under nitrogen. To this was added 4.02 g dibasic potassium phosphate, followed by 12 mL of trichloroacetonitrile. External cooling water was run through the reactor jacket and the reaction mixture was cooled to 8° C. To the addition funnel 36 mL of 30% hydrogen peroxide was added over a 10 minute period. The initially pale yellow colored reaction mixture turned almost colorless after the addition was complete. The reaction mixture remained at 9±1° C. throughout the addition and on continued stirring overnight (23 hours total). Methylene chloride (150 mL) was added to the reaction mixture and the entire contents were added to ~250 mL ice water. This was extracted three times with 150 mL aliquots of methylene chloride. The combined methylene chloride extracts were washed with 400 mL cold 3% sodium sulfite solution to decompose any residual peroxide. This was followed by a 330 mL cold 1 N sodium hydroxide wash, a 400 mL cold 1 N hydrochloric acid wash, and finally a wash with 400 mL brine. The organic phase was dried over magnesium sulfate, filtered, and the filter cake was washed with 80 mL methylene chloride. Solvent was removed in vacuo to give 9.10 g crude product as a pale yellow solid. This was recrystallized from ~25 mL 2-butanone to give 5.52 g nearly white crystals. A final recrystallization from acetone (~50 mL gave 3.16 g long, acicular crystals, mp 241–243° C.

EXAMPLE 27

Scheme 1: Step 3: Option 1: From 4'S(4'α),7'α-Hexadecahydro-11'α-hydroxy-10'β,13'β-dimethyl-3',5,20'-trioxospiro[furan-2(3H),17'β-[4,7]methano[17H]cyclopenta[a]phenanthrene]-5'β(2'H)-carbonitrile to Methyl Hydrogen 9,11α-Epoxy-17α-hydroxy-3-oxopregn-4-ene-7α,21-dicarboxylate, γ-Lactone.

Diketone (20 g) was charged into a clean and dried reactor followed by the addition of 820 ml of MeOH and 17.6 ml of 25% NaOMe/MeOH solution. The reaction mixture was heated to reflux condition (~67° C.) for 16–20 hours. The product was quenched with 40 mL of 4N HCl. The solvent was removed at atmospheric pressure by distillation. 100 mL of toluene was added and the residual methanol was removed by azeotrope distillation with toluene. After concentration, the crude hydroxyester 4 was dissolved in 206 mL of methylene chloride and cooled to 0° C. Methanesulfonyl chloride (5 mL) was added followed by a slow addition of 10.8 ml of triethylamine. The product was stirred for 45 minutes. The solvent was removed by vacuum distillation to give the crude mesylate 5.

In a separate dried reactor was added 5.93 g of potassium formate, 240 mL of formic acid and followed by 118 mL of acetic anhydride. The mixture was heated to 70° C. for 4 hours.

The formic acid mixture was added to the concentrated mesylate solution 5 prepared above. The mixture was heated to 95–105° C. for 2 hours. The product mixture was cooled to 50° C. and the volatile components were removed by vacuum distillations at 50° C. The product was partitioned between 275 ml of ethyl acetate and 275 ml of water. The aqueous layer was back extracted with 137 ml of ethyl acetate, washed with 240 ml of cold 1N sodium hydroxide solution and then 120 ml of saturated NaCl. After phase separation, the organic layer was concentrated to under vacuum distillation to give crude enester.

The product was dissolved in 180 mL of methylene chloride and cooled to 0 to 15° C. 8.68 g of dipotassium hydrogen phosphate was added followed by 2.9 mL of trichloroacetonitrile. A 78 mL solution of 30% hydrogen peroxide was added to the mixture over a 3 minute period. The reaction mixture was stirred at 0–15° C. for 6–24 hours. After the reaction, the two phase mixture was separated. The organic layer was washed with 126 mL of 3% sodium sulfite solution, 126 mL of 0.5 N sodium hydroxide solution, 126 mL of 1 N hydrochloric acid and 126 mL of 10% brine. The product was dried over anhydrous magnesium sulfate or filtered over Celite and the solvent methylene chloride was removed by distillation at atmospheric pressure. The product was crystallized from methylethyl ketone twice to give 7.2 g of eplerenone.

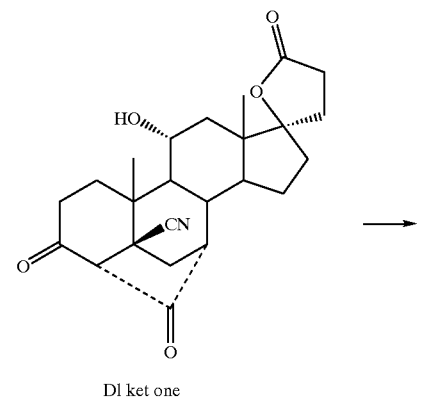

Dl ket one

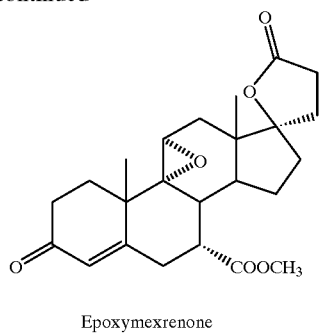

Epoxymexrenone

EXAMPLE 28

Scheme 1: Step 3: Option 2: Conversion o 1'S(4'α),7'α-Hexadecahydro-11'α-hydroxy-10'β,13'β-dimethyl-3',5,20'-trioxospiro[furan-2(3H),17'β-[4,7]methano[17H]cyclopenta[a]phenanthrene]-5'β(2'H)-carbonitrile to Methyl Hydrogen 9,11α-Epoxy-17α-hydroxy-3-oxopregn-4-ene-7α,21-dicarboxylate, γ-Lactone without intermediate.

A 4-neck 5-L round bottom flask was equipped with mechanical stirrer, addition funnel with nitrogen inlet tube, thermometer and condenser with bubbler attached to a sodium hypochlorite scrubber. The diketone (83.20 g) was added to the flask in 3.05 L methanol. The addition funnel was charged with 67.85 g of a 25% (w:w) solution of sodium methoxide in methanol. With stirring under nitrogen, the methoxide was added dropwise to the flask over a 15 minute period. A dark orange/yellow slurry developed. The reaction mixture was heated to reflux for 20 hours and 175 mL 4 N hydrochloric acid was added dropwise while refluxing continued. (Caution, HCN evolution during this operation!) The reflux condenser was replaced with a takeoff head and 1.6 L of methanol was removed by distillation while 1.6 L of aqueous 10% sodium chloride solution was added dropwise through the funnel, at a rate to match the distillation rate. The reaction mixture was cooled to ambient temperature and extracted twice with 2.25 L of aliquots of methylene chloride. The combined extracts were washed with cold 750 mL aliquots of 1 N sodium hydroxide and saturated sodium chloride solution. The organic layer was dried by azeotropic distillation of the methanol at one atmosphere, to a final volume of 1 L (0.5% of the total was removed for analysis).

The concentrated organic solution (hydroxyester) was added back to the original reaction flask equipped as before, but without the HCN trap. The flask was cooled to 0° C. and 30.7 g methanesulfonyl chloride was added with stirring under nitrogen. The addition funnel was charged with 32.65 g triethylamine, which was added dropwise over a 15 minute period, keeping the temperature at 5° C. Stirring was continued for 2 hours, while the reaction mixture warmed to ambient. A column consisting of 250 g Dowex 50 W×8-100 acid ion exchange resin was prepared and was washed before using with 250 mL water, 250 mL methanol and 500 mL methylene chloride. The reaction mixture was run down this column and collected. A fresh column was prepared and the above process was repeated. A third 250 g column, consisting of Dowex 1×8-200 basic ion exchange resin was prepared and pretreated as in the acid resin treatment described above. The reaction mixture was run down this column and collected. A fourth column of the basic resin was prepared and the reaction mixture again was run down the column and collected. Each column pass was followed by two 250 mL methylene chloride washes down the column, and each pass required ~10 minutes. The solvent washes were combined with the reaction mixture and the volume was reduced in vacuo to ~500 mL and 2% of this was removed for qc. The remainder was further reduced to a final volume of 150 mL (crude mesylate solution).

To the original 5-L reaction set-up was added 960 mL formic acid, 472 mL acetic anhydride and 23.70 g potassium formate. This mixture was heated with stirring under nitrogen to 70° C. for 16 hours. The temperature was then increased to 100° C. and the crude mesylate solution was added over a thirty minute period via the addition funnel. The temperature dropped to 85° C. as methylene chloride was distilling out of the reaction mixture. After all of it had been removed, the temperature climbed back to 100° C., and was held there for 2.5 hours. The reaction mixture was cooled to 40° C. and the formic acid was removed under pressure until the minimum stir volume had been reached (~150 mL). The residue was cooled to ambient and 375 mL methylene chloride was added. The diluted residue was washed with cold 1 L portions of saturated sodium chloride solution, 1 N sodium carbonate, and again with sodium chloride solution. The organic phase was dried over magnesium sulfate (150 g), and filtered to give a dark reddish brown solution (crude enester solution).

A 4-neck jacketed 1 L reactor was equipped with mechanical stirrer, condenser/bubbler, thermometer and addition funnel with nitrogen inlet tube. The reactor was charged with the crude enester solution (estimated 60 g) in 600 mL methylene chloride, with stirring under nitrogen. To this was added 24.0 g dibasic potassium phosphate, followed by 87 mL trichloroacetonitrile. External cooling water was run through the reactor jacket and the reaction mixture was cooled to 10° C. To the addition funnel 147 mL 30% hydrogen peroxide was added mixture over a 30 minute period. The initially dark reddish brown colored reaction mixture turned a pale yellow after the addition was complete. The reaction mixture remained at 10±1° C. throughout the addition and on continued stirring overnight (23 hours total). The phases were separated and the aqueous portion was extracted twice with 120 mL portions of methylene chloride. The combined organic phases were-then washed with 210 mL 3% sodium sulfite solution was added. This was repeated a second time, after which both the organic and aqueous parts were negative for peroxide by starch/iodide test paper. The organic phase was successively washed with 210 mL aliquots of cold 1 N sodium hydroxide, 1 N hydrochloric acid, and finally two washes with brine. The organic phase was dried azeotropically to a volume of ~100 mL, fresh solvent was added (250 mL and distilled azeotropically to the same 100 mL and the remaining solvent was removed in vacuo to give 57.05 g crude product as a gummy yellow foam. A portion (51.01 g) was further dried to a constant weight of 44.3 g and quantitatively analyzed by HPLC. It assayed at 27.1% EPX.

EXAMPLE 29

11α-Hydroxyandrostendione (429.5 g) and toluene sulfonic acid hydrate (7.1) were charged to a reaction flask under nitrogen. Ethanol (2.58 L) was added to the reactor, and the resulting solution cooled to 5° C. Triethyl orthoformate (334.5 g) was added to the solution over a 15 minute period at 0° to 15° C. After the triethyl orthoformate addition was complete the reaction mixture was warmed to 40° C. and reacted at that temperature for 2 hours, after which the temperature was increased to reflux and reaction continued under reflux for an additional 3 hours. The reaction mixture was cooled under vacuum and the solvent removed under vacuum to yield 3-ethoxyandrosta-3,5-diene-17-one.

EXAMPLE 30
Formation of Enamine from 11α-hydroxycanrenone

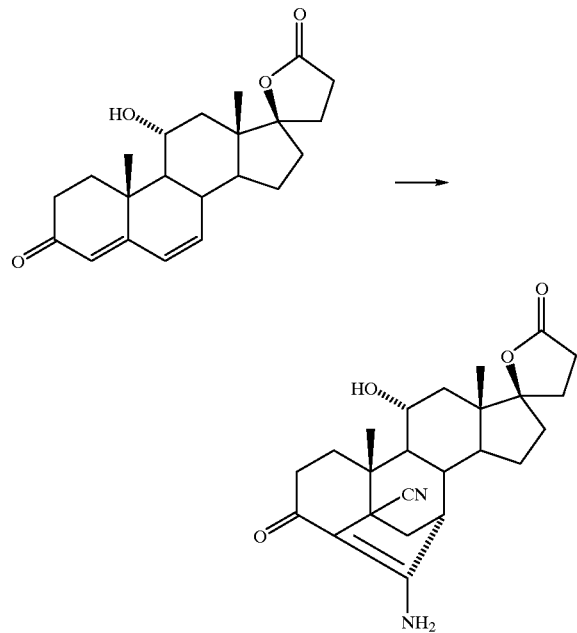

Sodium cyanide (1.72 g) was placed in 25 mL 3-neck flask fitted with a mechanical stirrer. Water (2.1 mL) was added and the mixture was stirred with heating until the solids dissolved. Dimethylformamide (15 mL) was added followed by 11α-hydroxycanrenone (5.0 g). A mixture of water (0.4 mL) and sulfuric acid (1.49 g) was added to mixture. The mixture was heated to 85° C. for 2.5 hours at which time HPLC analysis showed complete conversion to product. The reaction mixture was cooled to room temperature. Sulfuric acid (0.83 g) was added and the mixture stirred for one half hour. The reaction mixture was added to 60 mL water cooled in an ice bath. The flask was washed with 3 mL DMF and 5 mL water. The slurry was stirred for 40 min. and filtered. The filter cake was washed twice with 40 mL water and dried in a vacuum oven at 60° C. overnight to yield the 11α-hydroxy enamine, i.e., 5'R(5'α),7'β-20'-aminohexadecahydro-11,β-hydroxy-10'α,13'α-dimethyl-3',5-dioxospiro[furan-2(3H),17'α(5'H)-[7,4]metheno [4H] cyclopenta[a]phenanthrene]-5'-carbonitrile (4.9 g).

EXAMPLE 31
Conversion of 11α-hydroxycanrenone to Diketone

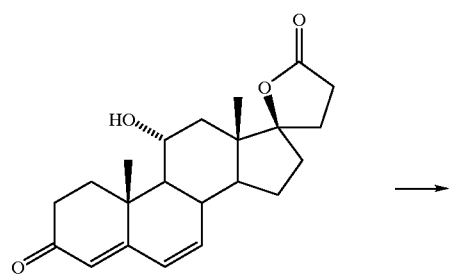

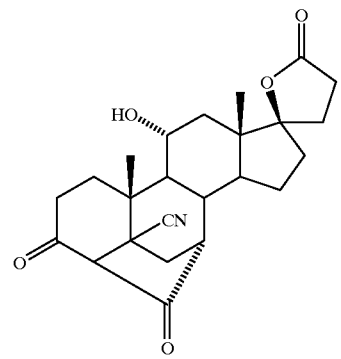

Sodium cyanide (1.03 g) was added to a 50 mL 3-neck flask fitted with a mechanical stirrer. Water (1.26 mL) was added and the flask was heated slightly to dissolve the solid. Dimethylacetamide [or dimethyformamide] (9 mL) was added followed by 11α-hydroxycanrenone (3.0 g). A mixture of sulfuric acid (0.47 mL) and water (0.25 mL) was added to the reaction flask while stirring. The mixture was heated to 95° C. for 2 hours. HPLC analysis indicated that the reaction was complete. Sulfuric acid (0.27 mL) was added and the mixture stirred for 30 min. Additional water (25 mL) and sulfuric acid (0.90 mL) were introduced and the reaction mixture stirred for 16 hours. The mixture was then cooled in an ice bath to 5–10° C. The solid was isolated by filtering through a sintered glass filter followed by washing twice with water (20 mL). The solid diketone, i.e., 4'S(4'α), 7'α-Hexadecahydro-11'α-hydroxy-10'β,13'β-dimethyl-3',5, 20'-trioxospiro[furan-2(3H),17'β-[4,7]methano[17H] cyclopenta[a]phenanthrene]-5'β(2'H)-carbonitrile was dried in a vacuum oven to yield 3.0 g of a solid.

EXAMPLE 32

A suspension of 5.0 g of the diketone produced in the manner described in Example 31 in methanol (100 mL) was heated to reflux and a 25% solution of potassium methoxide in methanol (5.8 mL) was added over 1 min. The mixture became homogeneous. After 15 min., a precipitate was present. The mixture was heated at reflux and again became homogeneous after about 4 hours. Heating at reflux was continued for a total of 23.5 hours and 4.0 N HCl (10 mL) was added. A total of 60 mL of a solution of hydrogen cyanide in methanol was removed by distillation. Water (57 mL) as added to the distillation residue over 15 min. The temperature of the solution was raised to 81.50 during water addition and an additional 4 mL of hydrogen cyanide/methanol solution was removed by distillation. After water addition was complete, the mixture became cloudy and the heat source was removed. The mixture was stirred for 3.5 hours and product slowly crystallized. The suspension was filtered and the collected solid was washed with water, dried in a stream of air on the funnel, and dried at 92° (26 in. Hg) for 16 hours to give 2.98 g of an off-white solid. The solid was 91.4% of the hydroxyester, i.e., methyl hydrogen 11α, 17α-dihydroxy-3-oxopregn-4-ene-7α,21-dicarboxylate, γ-lactone by weight. The yield was 56.1%.

EXAMPLE 33

Diketone prepared in the manner described in Example 31 was charged into a cleaned and dried 3-neck reaction flask equipped with a thermometer, a Dean Stark trap and a mechanical stirrer. Methanol (24 mL) was charged to the reactor at room temperature (22° C.) and the resulting slurry stirred for 5 min. A 25% by weight solution of sodium methoxide in methanol (52.8 mL) was charged to the reactor and the mixture stirred for 10 min. at room temperature during which the reaction mixture turned to a light brown clear solution and a slight exotherm was observed (2–3° C.). The addition rate was controlled to prevent the pot temperature from exceeding 30° C. The mixture was thereafter heated to reflux conditions (about 67° C.) and continued under reflux for 16 hrs. A sample was then taken and analyzed by HPLC for conversion. The reaction was continued under reflux until the residual diketone was not greater than 3% of the diketone charge. During reflux 4 N HCl (120 mL) was charged to the reaction pot resulting in the generation of HCN which was quenched in a scrubber.

After conclusion of the reaction, 90–95% of the methanol solvent was distilled out of the reaction mixture at atmospheric pressure. Head temperature during distillation varied from 67–75° C. and the distillate which contained HCN was treated with caustic and bleach before disposal. After removal of methanol the reaction mixture was cooled to room temperature, solid product beginning to precipitate as the mixture cooled in the 40–45° C. range. An aqueous solution containing optionally 5% by weight sodium bicarbonate (1200 mL) at 25° C. was charged to the cooled slurry and the resultant mixture then cooled to 0° C. in about 1 hr. Sodium bicarbonate treatment was effective to eliminate residual unreacted diketone from the reaction mixture. The slurry was stirred at 0° C. for 2 hrs. to complete the precipitation and crystallization after which the solid product was recovered by filtration and the filter cake washed with water (100 mL). The product was dried at 80–90° C. under 26" mercury vacuum to constant weight. Water content after drying was less than 0.25% by weight. Adjusted molar yield was around 77–80% by weight.

EXAMPLE 34

Diketone as prepared in accordance with Example 31 (1 eq.) was reacted with sodium methoxide (4.8 eqs.) in a methanol solvent in the presence of zinc iodide (1 eq.). Work up of the reaction product can be either in accordance with the extractive process described herein, or by a non-extractive process in which methylene chloride extractions, brine and caustic washes, and sodium sulfate drying steps are eliminated. Also in the non-extractive process, toluene was replaced with 5% by weight sodium bicarbonate solution.

EXAMPLE 35

The hydroxyester prepared as by Example 34 (1.97 g) was combined with tetrahydrofuran (20 mL) and the resulting mixture cooled to −70° C. Sulfuryl chloride (0.8 mL) was added and the mixture was stirred for 30 min., after which imidazole (1.3 g) was added. The reaction mixture was warmed to room temperature and stirred for an additional 2 hrs. The mixture was then diluted with methylene chloride and extracted with water. The organic layer was concentrated to yield crude enester (1.97 g). A small sample of the crude product was analyzed by HPLC. The analysis showed that the ratio of 9,11-olefin: 11,12-olefin: 7,9-lactone was 75.5:7.2:17.3. When carried out at 0° C. but otherwise as described above, the reaction yielded a product in which the 9,11-olefin: 11,12-olefin: 7,9-lactone distribution was 77.6:6.7:15.7. This procedure combines into one step the introduction of a leaving group and elimination thereof for the introduction of the 9,11-olefin structure of the enester, i.e., reaction was sulfuryl chloride causes the 11α-hydroxy group of the hydroxy ester of Formula V to be replaced by halide and this is followed by dehydrohalogenation to the Δ-9,11 structure. Thus formation of the enester is effected without the use of a strong acid (such as formic) or a drying agent such as acetic anhydride. Also eliminated is the refluxing step of the alternative process which generates carbon monoxide.

EXAMPLE 36

Hydroxyester (20 g) prepared as by Example 34, and methylene chloride (400 mL) were added to a clean dry three-neck round bottom flask fitted with a mechanical stirrer, addition funnel and thermocouple. The resulting mixture was stirred at ambient temperature until complete solution was obtained. The solution was cooled to 5° C. using an ice bath. Methanesulfonyl chloride (5 mL) was added to the solution of $CH_2Cl_2$ containing the hydroxyester, rapidly followed by the slow dropwise addition of triethylamine (10.8 mL). The addition rate was adjusted so that the temperature of the reaction did not exceed 5° C. The reaction was very exothermic; therefore cooling was necessary. The reaction mixture was stirred at about 5° C. for 1 h. When the reaction was complete (HPLC and TLC analysis), the mixture was concentrated at about 0° C. under 26 in Hg vacuum until it became a thick slurry. The resulting slurry was diluted with $CH_2Cl_2$ (160 mL), and the mixture was concentrated at about 0° C. under 26 in Hg vacuum to obtain a concentrate. The purity of the concentrate (mesylate product of Formula IV wherein $R^3$=H and —A—A— and —B—B— are both —$CH_2$—$CH_2$—, i.e., methyl hydrogen 11α,17α-dihydroxy-3-oxopregn-4-ene-7α,21-dicarboxylate, γ-lactone to methyl hydrogen 17α-hydroxy-11α-(methylsulfonyl)oxy-3-oxopregn-4-ene-7α,21-dicarboxylate, γ-lactone was found to be 82% (HPLC area %). This material was used for the next reaction without isolation.

Potassium formate (4.7 g), formic acid (16 mL) and acetic anhydride (8 mL, 0.084 mol) were added to a clean dry reactor equipped with mechanical stirrer, condenser, thermocouple and heating mantle. The resulting solution was heated to 70° C. and stirred for about 4–8 hours. The addition of acetic anhydride is exothermic and generated gas (CO), so that the rate of addition had to be adjusted to control both temperature and gas generation (pressure). The reaction time to prepare the active eliminating reagent was dependent on the amount of water present in the reaction (formic acid and potassium formate contained about 3–5% water each). The elimination reaction is sensitive to the amount of water present; if there is >0.1% water (KF), the level of the 7,9-lactone impurity may be increased. This by product is difficult to remove from the final product. When the KF showed <0.1% water, the active eliminating agent was transferred to the concentrate of mesylate (0.070 mol) prepared in the previous step. The resulting solution was heated to 95° C. and the volatile material was distilled off and collected in a Dean Stark trap. When volatile material evolution ceased, the Dean Stark trap was replaced with the condenser and the reaction mixture was heated for additional 1 h at 950C. Upon completion (TLC and HPLC analysis; <0.1% starting material) the content was cooled to 50° C. and vacuum distillation was started (26 in Hg/50° C.). The mixture was concentrated to a thick slurry and then cooled to ambient temperature. The resulting slurry was diluted with ethyl acetate (137 mL) and the solution was stirred for 15 min. and diluted with water (137 mL). The layers were separated, and the aqueous lower layer was re-extracted with ethyl acetate (70 mL). The combined ethyl acetate solution was washed once with brine solution (120 mL) and twice with ice cold 1N NaOH solution (120 mL each). The pH of aqueous was measured, and the organic layer rewashed if the pH of the spent wash liquor was <8. When the pH of the spent wash was observed to be >8, the ethyl acetate layer was washed once with brine solution (120 mL) and concentrated to dryness by rotary evaporation using a 50° C. water bath. The resulting enester, solid product i.e., methyl hydrogen 17α-hydroxy-3-oxopregna-4,9(11)-diene-7α,21-dicarboxylate, γ-lactone weighed 92 g (77% mol yield).

EXMAPLE 37

Hydroxyester (100 g; 0.22 mol) prepared as by Example 34 was charged to a 2 L 3-neck round bottom flask equipped with mechanical stirrer, addition funnel, and thermocouple. A circulating cooling bath was used with automatic temperature control. The flask was dried prior to reaction because of the sensitivity of methanesulfonyl chloride to water.

Methylene chloride (1 L) was charged to the flask and the hydroxyester dissolved therein under agitation. The solution was cooled to 0° C. and methane sulfonyl chloride (25 mL; 0.32 mol) was charged to the flask via the addition funnel. Triethylamine (50 mL; 0.59 mol) was charged to the reactor via the addition funnel and the funnel was rinsed with additional methylene chloride (34 mL). Addition of triethylamine was highly exothermic. Addition time was around 10 min. under agitation and cooling. The charge mixture was cooled to 0° C. and held at that temperature under agitation for an additional 45 min. during which the head space of the reaction flask was flushed with nitrogen. A sample of the reaction mixture was then analyzed by thin layer chromatography and high performance liquid chromatography to check for reaction completion. The mixture was thereafter stirred at 0° C. for an additional 30 min. and checked again for reaction completion. Analysis showed the reaction to be substantially complete at this point; the solvent methylene chloride was stripped at 0° C. under 26" mercury vacuum. Gas chromatography analysis of the distillate indicated the presence of both methane sulfonyl chloride and triethylamine. Methylene chloride (800 mL) was thereafter charged to the reactor and the resulting mixture was stirred for 5 min. at a temperature in the range of 0–15° C. The solvent was again stripped at 0–5° C. under 26" mercury vacuum yielding the mesylate of Formula IV wherein $R^3$ is H, —A—A— and —B—B— are —$CH_2$—$CH_2$— and $R^1$ is methoxy carbonyl. The purity of the product was about 90–95 area %.

To prepare an elimination reagent, potassium formate (23.5 g; 0.28 mol), formic acid (80 mL) and acetic anhydride (40 mL) were mixed in a separate dried reactor. Formic acid and acetic anhydride were pumped into the reactor and the temperature was maintained not greater than 40° C. during addition of acetic anhydride. The elimination reagent mixture was heated to 70° C. to scavenge water from the reaction system. This reaction was continued until the water content was lower than 0.3% by weight as measured by Karl Fisher analysis. The elimination reagent solution was then transferred to the reactor containing the concentrated crude mesylate solution prepared as described above. The resulting mixture was heated to a maximum temperature of 95° C. and volatile distillate collected until no further distillate was generated. Distillation ceased at about 90° C. After distillation was complete, the reaction mixture was stirred at 95° C. for an additional 2 hrs. and completion of the reaction was checked for thin layer chromatography. When the reaction was complete, the reactor was cooled to 50° C. and the formic acid and solvent removed from the reaction mixture under 26" mercury vacuum at 50° C. The concentrate was cooled to room temperature and thereafter ethyl acetate (688 mL) was introduced and the mixture of ethyl acetate and concentrate stirred for 15 min. At this point, a 12% brine solution (688 mL) was introduced to assist in removing water soluble impurities from the organic phase. The phases were then allowed to settle for 20 min. The aqueous layer was transferred to another vessel to which an additional amount of ethyl acetate (350 mL) was charged. This back extraction of the aqueous layer was carried out for 30 min. after which the phases were allowed to settle and the ethyl acetate layers combined. To the combined ethyl acetate layers, saturated sodium chloride solution (600 mL) was charged and stirring carried out for 30 min. The phases were then allowed to settle. The aqueous layer was removed. An additional sodium chloride (600 mL) wash was carried out. The organic phase was separated from the second spent wash liquor. The organic phase was then washed with 1 N sodium hydroxid e (600 mL) under stirring for 30 mi. The phases were settled for 30 mmin. to remove the aqueous layer. The pH of the aqueous layer was checked and it found to be >7. A further wash was carried out with saturated sodium chloride (600 mL) for 15 min. The organic phase was finally concentrated under 26" mercury vacuum at 50° C. and the product recovered by filtration. The final product was a foamy brown solid when dried. Further drying at 45° C. under reduced pressure for 24 hrs. yielded 95.4 g of the enester product which assayed at 68.8%. The molar yield was 74.4% corrected for both the starting hydroxy ester and the final enester.

EXMAPLE 38

The procedure of Example 37 was repeated except that the multiple washing steps were avoided by treating the reaction solution with an ion exchange resin. Basic alumina or basic silica. Condit ions for treatment with basic silica are set forth in Table 38. Each of the se treatments was found effective for removal of impurities without the multiple washes of Example 44.

TABLE 38

| Factor | Set point | Purpose of Experiment | Key results |
| --- | --- | --- | --- |
| Basic alumina | 2 g/125 g product | Treating the reaction mixture with basic alumina to remove $Et_3N.HCl$ salt and to eliminate the 1N NaOH and 1N HCl washes | The yield was 93% |
| Basic silica | 2 g/125 g product | Treating the reaction mixture with basic silica which is cheaper to remove $Et_3N.HCl$ salt and eliminate 1N NaOH and 1N HCl washes | The yield was 95% |

EXAMPLE 39

Potassium acetate (4 g) and trifluoroacetic acid (42.5 mL) were mixed in a 100 mL reactor. trifluoroacetic anhydride (9.5 mL) was added to the mixture at a rate controlled to maintain temperature during addition below 30° C. The solution was then heated to 30° C. for 30 min. to provide an elimination reagent useful for converting the mesylate of Formula IV to the enester of Formula II.

The preformed TFA/TFA anhydride elimination reagent was added to a previously prepared solution of the mesylate of Formula IV. The resulting mixture was heated at 40° C. for 4½ hrs., the degree of conversion being periodically checked by TLC or HPLC. When the reaction was complete, the mixture was transferred to 1-neck flask and concentrated to dryness under reduced pressure at room temperature (22° C.). Ethyl acetate (137 mL) was added to the mixture to obtain complete dissolution of solid phase material after which a water/brine mixture (137 mL) was added and the resulting two phase mixture stirred for 10 min. The phases were then allowed to separate for 20 min. Brine strength was 24% by weight. The aqueous phase was contacted with an additional amount of ethyl acetate (68 mL) and the two phase mixture thus prepared was stirred for 10 min. after which it was allowed to stand for 15 min. for phase separation. The ethyl acetate layers from the two extractions were combined and washed with 24% by weight brine (120 mL), another aliquot of 24% by weight brine (60 mL), 1 N sodium hydroxide solution (150 mL) and another portion of brine (60 mL). After each aqueous phase addition, the mixture was stirred for 10 min. and allowed to stand for 15 min. for separation. The resulting solution was concentrated to dryness under reduced pressure at 45° C. using a water aspirator. The solid product (8.09 g) was analyzed by HPLC and found to include 83.4 area % of the enester, 2.45 area % of the 11,12-olefin, 1.5% of the 7,9-lactone, and 1.1% of unreacted mesylate.

EXAMPLE 40

The mesylate having the structure prepared per Example 23 (1.0 g), isopropenyl acetate (10 g) and p-toluenesulfonic acid (5 mg) were placed in a 50 ml flask and heated to 90° C. with stirring. After 5 hours the mixture was cooled to 25° C. and concentrated in vacuo at 10 mm of Hg. The residue was dissolved in $CH_2Cl_2$ (20 ml) and washed with 5% aqueous $NaHCO_3$. The $CH_2Cl_2$ layer was concentrated in vacuo to give 1.47 g of a tan oil. This material was recrystallized from $CH_2Cl_2/Et_2O$ to give 0.50 g of enol acetate of Formula IV(Z).

This material was added to a mixture of sodium acetate (0.12 g) and acetic acid (2.0 ml) that had been previously heated to 100° C. with stirring. After 60 minutes the mixture was cooled to 25° C. and diluted with $CH_2Cl_2$ (20 ml). The solution was washed with water (20 ml) and dried over $MgSO_4$. The drying agent was removed by filtration and the filtrate was concentrated in vacuo to give 0.4 g of the desired 9,11-olefin, IV(Y). The crude product contained less than 2% of the 7,9-lactone impurity.

EXAMPLE 41
Thermo Elimination of Mesvlate in DMSO.

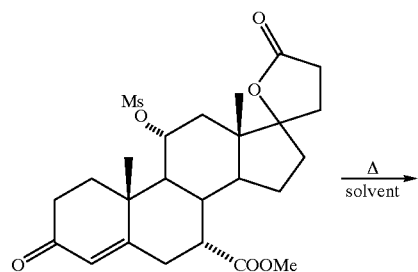

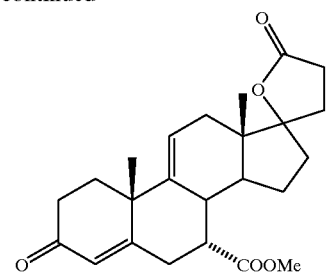

A mixture of 2 g of mesylate and 5 ml of DMSO in a flask was heated at 80° C. for 22.4 hours. HPLC analysis of the reaction mixture indicated no starting material was detected. To the reaction was added water (10 ml) and the precipitate was extracted with methylene chloride three times. The combined methylene chloride layers were washed with water, dried over magnesium sulfate, and concentrated to give the enester.

EXAMPLE 42

In a 50 mL pear-shaped flask under stirring the enester of Formula IIA (1.07 g assaying 74.4% enester), trichloroacetamide (0.32 g), dipotassium hydrogen phosphate (0.70 g) as solid were mixed with methylene chloride (15.0 mL). A clear solution was obtained. Hydrogen peroxide (30% by weight; 5.0 mL) was added via a pipet over a 1 min. period. The resulting mixture was stirred for 6 hrs. at room temperature at which point HPLC analysis showed that the ratio of epoxymexrenone to enester in the reaction mixture was approximately 1:1. Additional trichloroacetamide (0.32 g) was added to the reaction mixture and reaction continued under agitation for 8 more hours after which time the remaining proportion of enester was shown to have been reduced to 10%. Additional trichloroacetamide (0.08 g) was added and the reaction mixture was allowed to stand overnight at which point only 5% of unreacted enester remained relative to epoxymexrenone in the mixture.

EXAMPLE 43

Enester of Formula IIA (5.4 g, assaying 74.4% enester) was added to a 100 mL reactor. Trichloroacetamide (4.9 g) and dipotassium hydrogen phosphate (3.5 g) both in solid form were added to the enester followed by methylene chloride (50 mL). The mixture was cooled to 15° C. and a 30% hydrogen peroxide (25 g) was added over a ten min. period. The reaction mixture was allowed to come to 20° C. and stirred at that temperature for 6 hrs., at which point conversion was checked by HPLC. Remaining enester was determined to be less than 1% by weight.

The reaction mixture was added to water (100 mL), the phases were allowed to separate, and the methylene chloride layer was removed. Sodium hydroxide (0.5 N; 50 mL) was added to the methylene chloride layer. After 20 min. the phases were allowed to separate HCl (0.5 N; 50 mL) was added to the methylene chloride layer after which the phases were allowed to separate and the organic phase was washed with saturated brine (50 mL). The methylene chloride layer was dried over anhydrous magnesium sulfate and the. solvent removed. A white solid (5.7 g) was obtained. The aqueous sodium hydroxide layer was acidified and extracted and the extract worked up to yield an additional 0.2 g of product. Yield of epoxymexrenone was 90.2%.

EXAMPLE 44

Enester of Formula IIA was converted to epoxymexrenone in the manner described in Example 43 with the following differences: the initial charge comprised of enester (5.4 g assaying 74.4% enester), trichloroacetamide (3.3 g), and dipotassium hydrogen phosphate (3.5 g). Hydrogen peroxide solution (12.5 mL) was added. The reaction was conducted overnight at 20° C. after which HPLC showed a 90% conversion of enester to epoxymexrenone. Additional trichloroacetamide (3.3 g) and 30% hydrogen peroxide (5.0 mL) was added and the reaction carried out for an additional 6 hrs. at which point the residual enester was only 2% based on the enester charge. After work up as described in Example 43, 5.71 g of epoxymexrenone resulted.

EXAMPLE 45

The enester of Formula IIA was converted to epoxymexrenone in the manner generally described in Example 43. In the reaction of this Example, enester charge was 5.4 g (assaying 74.4% enester), the trichloroacetamide charge was 4.9 g, hydrogen peroxide charge was 25 g, dipotassium hydrogen phosphate charge was 3.5 g. The reaction was run at 20° C. for 18 hrs. The residual enester was less than 2%. After work up, 5.71 g of epoxymexrenone resulted.

EXAMPLE 46

Enester of Formula IIA was converted to epoxymexrenone in the manner described in Example 43 except that the reaction temperature in this Example was 28° C. The materials charged in the reactor included enester (2.7 g), trichloroacetamide (2.5 g), dipotassium hydrogen phosphate (1.7 g), hydrogen peroxide (17.0 g) and methylene chloride (50 mL). After 4 hrs. reaction, unreacted enester was only 2% based on the enester charge. After work up as described in Example 43, 3.0 g of epoxymexrenone was obtained.

EXAMPLE 47

Enester of Formula IIA (17 g assaying 72% enester) was dissolved in methylene chloride (150 mL) after which trichloroacetamide (14.9 g) was added under slow agitation. The temperature of the mixture was adjusted to 25° C. and the solution of dipotassium hydrogen phosphate (10.6 g) in water (10.6 mL) was stirred into the enester substrate solution under 400 rpm agitation. Hydrogen peroxide (30% by weight solution; 69.4 mL) was added to the substrate/phosphate/ trichloroacetamide solution over a 3–5 min. period. No exotherm or oxygen evolution was observed. The reaction mixture thus prepared was stirred at 400 rpm and 25° C. for 18.5 hrs. No oxygen evolution was observed throughout the course of the reaction. The reaction mixture was diluted with water (69.4 mL) and the mixture stirred at about 250 rpm for 15 min. No temperature control was necessary for this operation and it was conducted essentially at room temperature (any temperature in the range of 5–25° C. being acceptable). The aqueous and organic layers were allowed to separate and the lower methylene chloride layer was removed.

The aqueous layer was back extracted with methylene chloride (69.4 mL) for 15 min. under agitation of 250 rpm. The layers were allowed to separate and the lower methylene chloride layer was removed. The aqueous layer (177 g; pH=7) was submitted for hydrogen peroxide determination. The result (12.2%) indicating that only 0.0434 mol of hydrogen peroxide were consumed in the reaction was 0.0307 mol of olefin. Back extraction with a small amount of methylene chloride volume was sufficient to insure no loss of epoxymexrenone in the aqueous layer. This result was confirmed with the application of a second large methylene chloride extraction in which only trichloroacetamide was recovered.

The combined methylene chloride solutions from the above described extractions were combined and washed with 3% by weight sodium sulfite solution (122 mL) for at least 15 min. at about 250 rpm. A negative starch iodide test (KI paper; no color observed; in a positive test a purple coloration indicates the presence of peroxide) was observed at the end of the stir period.

The aqueous and organic layers were allowed to separate and the lower methylene chloride layer removed. The aqueous layer (pH=6) was discarded. Note that addition of sodium sulfite solution can cause a slight exotherm so that such addition should be carried out under temperature control.

The methylene chloride phase was washed with 0.5 N sodium hydroxide (61 mL) for 45 min. at about 250 rpm and a temperature in the range of 15–25° C. (pH=12–13). Impurities derived from trichloroacetamide were removed in this process. Acidification of the alkaline aqueous fraction followed by extraction of the methylene chloride confirmed that very little epoxymexrenone was lost in this operation.

The methylene chloride phase was washed once with 0.1 N hydrochloric acid (61 mL) for 15 min. under 250 rpm agitation at a temperature in the range 15–25° C. The layers were then allowed to separate and the lower methylene chloride layer removed and washed again with 10% by weight aqueous sodium chloride (61 mL) for 15 min at 250 rpm at a temperature in the range of 15–25° C. Again the layers were allowed to separate and the organic layer removed. The organic layer was filtered through a pad of Solkafloc and then evaporated to dryness under reduced pressure. Drying was completed with a water bath temperature of 65° C. An off-white solid (17.95 g) was obtained and submitted for HPLC assay. Epoxymexrenone assay was 66.05%. An adjusted molar yield for the reaction was 93.1%.

The product was dissolved in hot methyl ethyl ketone (189 mL) and the resulting solution was distilled at atmospheric pressure until 95 mL of the ketone solvent had been removed. The temperature was lowered to 50° C. as the product crystallized. Stirring was continued at 50° C. for 1 hr. The temperature was then lowered to 20–25° C. and stirring continued for another 2 hrs. The solid was filtered and rinsed with MEK (24 mL) and the solid dried to a constant weight of 9.98 g, which by HPLC assay contain 93.63% epoxymexrenone. This product was re-dissolved in hot MEK (106 mL) and the hot solution filtered through a 10 micron line filter under pressure. Another 18 mL of MEK was applied as a rinse and the filtered MEK solution distilled at atmospheric pressure until 53 mL of solvent had been removed. The temperature was lowered to 50° C. as the product crystallized; and stirring was continued at 50° C. for 1 hr. The temperature was then lowered to 20–25° C. and held at that temperature while stirring was continued for another 2 hrs. The solid product was filtered and rinsed with MEK (18 mL). The solid product was dried to a constant weight of 8.32 g which contained 99.6% epoxymexrenone per quantitative HPLC assay. The final loss on drying was less than 1.0%. Overall yield of epoxymexrenone in accordance with the reaction and work up of this Example is 65.8%. This overall yield reflected a reaction yield of 93%, an initial crystallization recovery of 78.9%, and a recrystallization recovery of 89.5%.

EXAMPLE 48
Epoxidation of Formula IIA Using Toluene

The enester of Formula IIA was converted to eplerenone in the method generally described in Example 46 except that toulene was used as the solvent. The materials charged to the reactor included enester (2.7 g) trichloroacetamide (2.5 g), dipotassium hydrogen phosphate (1.7 g), hydrogen peroxide (17.0 g) and toulene (50 ml). The reaction was allowed to exotherm to 28° C. and was complete in 4 hours. The resulting three phase mixture was cooled to 15° C., filtered, washed with water and dried in vacuo to yield 2.5 g of product.

EXAMPLE 49
Epoxidation of 9,11-Dienone

A compound designated XVIIA (compound XVII wherein —A—A— and —B—B— are both —CH$_2$—CH$_2$—) (40.67 g) was dissolved in methylene chloride (250 mL) in a one liter 3 necked flask and cooled by ice salt mixture externally. Dipotassium phosphate (22.5 g), and trichloroacetonitrile (83.5 g) were added and mixture cooled to 2° C. after which 30% Hydrogen peroxide (200 g) was slowly added over a period of 1 hour. The reaction mixture was stirred at 12° for 8 hours and 14 hours at room temperature. A drop of the organic layer was taken and checked for any starting enone and was found to be <0.5%. Water (400 mL) was added, stirred for 15 min. and layers separated. The organic layer was washed successively with 200 mL of potassium iodide (10%), 200 mL of sodium thiosulfate (10%) and 100 mL of saturated sodium bicarbonate solution separating layers each time. The organic layer was dried over anhydrous magnesium sulfate and concentrated to yield crude epoxide (41 g). The product crystallized from ethyl acetate:methylene chloride to give 14.9 g of pure material.

EXAMPLE 50
Epoxidation of Compound XVIIA Using m-chloroperbenzoic Acid

Compound XVIIA (18.0 g) was dissolved in 250 mL of methylene chloride and cooled to 10° C. Under stirring solid m-chloroperbenzoic acid, (50–60% pure, 21.86 g) was added during 15 min. No rise in temperature was observed. The reaction mixture was stirred for 3 hours and checked for the presence of the dienone. The reaction mixture was treated successively with sodium sulfite solution (10%), sodium hydroxide solution (0.5N), hydrochloric acid solution (5%) and finally with 50 mL of saturated brine solution. After drying with anhydrous magnesium sulfate and evaporation, 17.64 g of the epoxide resulted and was used directly in the next step. The product was found to contain Baeyer-Villiger oxidation product that had to be removed by trituration from ethyl acetate followed by crystallization from methylene chloride. On a 500 g scale, the precipitated m-chlorobenzoic acid was filtered followed by the usual work up.

EXAMPLE 51
Epoxidation of Compound XVIIA Using Trichloroacetamide

Compound XVIIA (2 g) was dissolved in 25 mL of methylene chloride. Trichloroacetamide (2 g), dipotassium phosphate (2 g) were added. Under stirring at room temperature 30% hydrogen peroxide (10 mL) was added and stirring continued for 18 hours to yield the epoxide (1.63 g). Baeyer-Villiger product was not formed.

EXAMPLE 52

Potassium hydroxide (56.39 g; 1005.03 mmol; 3.00 eq.) was charged to a 2000 mL flask and slurried with dimethylsulfoxide (750.0 mL) at ambient temperature. A trienone corresponding to Formula XX (wherein R$^3$ is H and —A—A— and —B—B— are each —CH$_2$—CH$_2$—) (100.00 g; 335.01 mmol; 1.00 eq.) was charged to the flask together with THF (956.0 mL). Trimethylsulfonium methylsulfate (126.14 g; 670.02 mmol; 2.00 eq.) was charged to the flask and the resulting mixture heated at reflux, 80 to 85° C. for 1 hr. Conversion to the 17-spirooxymethylene was checked by HPLC. THF approximately 1 L was stripped from the reaction mixture under vacuum after which water (460 mL) was charged over a 30 min. period while the reaction mixture was cooled to 15° C. The resulting mixture was filtered and the solid oxirane product washed twice with 200 mL aliquots of water. The product was observed to be highly crystalline and filtration was readily carried out. The product was thereafter dried under vacuum at 40° C. 104.6 g of the 3-methyl enol ether Δ-5,6,9,11,-17-oxirane steroid product was isolated.

EXAMPLE 53

Sodium ethoxide (41.94 g; 616.25 mmol; 1.90 eq.) was charged to a dry 500 mL reactor under a nitrogen blanket. Ethanol (270.9 mL) was charged to the reactor and the sodium methoxide slurried in the ethanol. Diethyl malonate (103.90 g; 648.68 mmol; 2.00 eq.) was charged to the slurry after which the oxirane steroid prepared in the manner described in Example 52 (104.60 g; 324.34 mmol; 1.00 eq.) was added and the resulting mixture heated to reflux, i.e., 80 to 85° C. Heating was continued for 4 hrs. after which completion of the reaction was checked by HPLC. Water (337.86 mL) was charged to the reaction mixture over a 30 min. period while the mixture was being cooled to 15° C. Stirring was continued for 30 min. and then the reaction slurry filtered producing a filter cake comprising a fine amorphous powder. The filter cake was washed twice with water (200 mL each) and thereafter dried at ambient temperature under vacuum. 133.8 g of the 3-methyl enolether-Δ5,6,9,11,-17-spirolactone-21-methoxycarbonyl intermediate was isolated.

EXAMPLE 54

The 3-methyl enolether-Δ5,6,9,11,-17-spirolactone-21-methoxycarbonyl intermediate (Formula XVIII where R$^3$ is H and —A—A— and —B—B— are each —CH$_2$—CH$_2$—; 133.80 g; 313.68 mmol; 1.00 eq., as produced in Example 53, was charged to the reactor together with sodium chloride (27.50 g; 470.52 mmol; 1.50 eq.) dimethyl formamide (709 mL) and water (5 mL) were charged to a 2000 mL reactor under agitation. The resulting mixture was heated to reflux, 138 to 142° C. for 3 hrs. after which the reaction mixture was checked for completion of the reaction by HPLC. Water was thereafter added to the mixture over a 30 min. period while the mixture was being cooled to 15° C. Agitation was continued for 30 min. after which the reaction slurry was filtered recovering amorphous solid reaction product as a filter cake. The filter cake was washed twice (200 mL aliquots of water) after which it was dried. The product 3-methylenolether-17-spirolactone was dried yielding 91.6 g (82.3% yield; 96 area % assay).

EXAMPLE 55

The enol ether produced in accordance with Example 54 (91.60 g; 258.36 mmol; 1.00 eq.) ethanol (250 mL) acetic acid (250 mL) and water (250 mL) were charged to a 2000 mL reactor and the resulting slurry heated to reflux for 2 hrs. Water (600 mL) was charged over a 30 min. period while the reaction mixture was being cooled to 15° C. The reaction slurry was thereafter filtered and the filter cake washed twice with water (200 mL aliquots). The filter cake was then dried; 84.4 g of product 3-keto Δ4,5,9,11,-17-spirolactone was isolated (compound of Formula XVII where $R^3$ is H and —A—A— and —B—B— are —$CH_2$—$CH_2$—; 95.9% yield).

EXAMPLE 56

Compound XVIIA (1 kg; 2.81 moles) was charged together with carbon tetrachloride (3.2 L) to a 22 L 4-neck flask. N-bromo-succinamide (538 g) was added to the mixture followed by acetonitrile (3.2 L). The resulting mixture was heated to reflux and maintained at the 68° C. reflux temperature for approximately 3 hrs. producing a lear orange solution. After 5 hrs. of heating, the olution turned dark. After 6 hrs. the heat was removed nd the reaction mixture was sampled. The solvent was stripped under vacuum and ethyl acetate (6 L) added to the residue in the bottom of the still. The resultant mixture was stirred after which a 5% sodium bicarbonate solution (4 L) was added and the mixture stirred for 15 min. after which the phases were allowed to settle. The aqueous layer was removed and saturated brine solution (4 L) introduced into the mixture which was then stirred for 15 min. The phases were again separated and the organic layer stripped under vacuum producing a thick slurry. Dimethylformamide (4 L) was then added and stripping continued to a pot temperature of 55° C. The still bottoms were allowed to stand overnight and DABCO (330 g) and lithium bromide (243 g) added. The mixture was then heated to 70° C. After one and one-half hrs. heating, a liquid chromatography sample was taken and after 3.50 hrs. heating, additional DABCO (40 g) was added. After 4.5 hrs. heating, water (4 L) was introduced and the resulting mixture was cooled to 15° C. The slurry was filtered and the cake washed with water (3 L) and dried on the filter overnight. The wet cake (978 g) was charged back into the 22 L flask and dimethylformamide (7 L) added. The mixture thus produced was heated to 105° C. at which point the cake had been entirely taken up into solution. The heat was removed and the mixture in the flask was stirred and cooled. Ice water was applied to the reactor jacket and the mixture within the reactor cooled to 14° C. and held for two hours. The resulting slurry was filtered and washed twice with 2.5 L aliquots of water. The filter cake was dried under vacuum overnight. A light brown solid product 510 g was obtained.

EXAMPLE 57

To a 2 L 4-neck flask were charged: 9,11-epoxy anrenone as produced in Example 49, 50, or 51 (100.00 g; 282.1 mmol; 1.00 eq.), dimethylformamide (650.0 mL), lithium chloride (30.00 g; 707.7 mmol; 2.51 eq.), and acetone cyanohydrin (72.04 g; 77.3 mL; 846.4 mmol; 3.00 eq.). The resulting suspension was mechanically stirred and treated with tetramethyl guanidine (45.49 g; 49.6 mL; 395.0 mmol; 1.40 eq.). The system was then filtered with a water cooled condenser and a dry ice condenser (filled with dry ice in acetone) to prevent escape of HCN. The vent line from the dry ice condenser passed into a scrubber filled with a large excess of chlorine bleach. The mixture was heated to 80° C.

After 18 hrs., a dark reddish-brown solution was obtained which was cooled to room temperature with stirring. During the cooling process, nitrogen was sparged into the solution to remove residual HCN with the vent line being passed into bleach in the scrubber. After two hrs. the solution was treated with acetic acid (72 g) and stirred for 30 min. The crude mixture was then poured into ice water (2 L) with stirring. The stirred suspension was further treated with 10% aqueous HCl (400 mL) and stirred for 1 hr. Then the mixture was filtered to give a dark brick-red solid (73 g). The filtrate was placed in a 4 L separatory funnel and extracted with methylene chloride (3×800 mL); and the organic layers were combined and back extracted with water (2×2 L). The methylene chloride solution was concentrated in vacuo to give 61 g of a dark red oil.

After the aqueous wash fractions were allowed to sit overnight, a considerable precipitate developed. This precipitate was collected by filtration and determined to be pure product enamine (14.8 g).

After drying the original red solid (73 g) was analyzed by HPLC and it was determined that the major component was the 9,11-epoxyenamine. HPLC further showed that enamine was the major component of the red oil obtained from methylene chloride workup. Calculated molar yield of enamine was 46%.

EXAMPLE 58

9,11-epoxyenamine (4.600 g; 0.011261 mol; 1.00 eq.) as prepared in accordance with Example 57 was introduced into a 1000 mL round bottom flask. Methanol (300 mL) and 0.5% by weight aqueous HCl (192 mL) were added to the mixture which was thereafter refluxed for 17 hrs. Methanol was thereafter removed under vacuum reducing the amount of material in the still pot to 50 mL and causing a white precipitate to be formed. Water (100 mL) was added to the slurry which was thereafter filtered producing a white solid cake which was washed three times with water. Yield of solid 9,11-epoxydiketone product was 3.747 g (81.3%).

EXAMPLE 59

The epoxydiketone prepared in accordance with Example 58 (200 mg; 0.49 mmol) was suspended in methanol (3 mL) and 1,8-diazabicyclo[5.4.0]undec-7-ene(DBU) added to the mixture. Upon heating under reflux for 24 hrs. the mixture became homogeneous. It was then concentrated to dryness at 30° C. on a rotary evaporator and the residue partitioned between methylene chloride and 3.0 N HCl. Concentration of the organic phase yielded a yellow solid (193 mg) which was determined to be 22% by weight epoxy mexrenone. The yield was 20%.

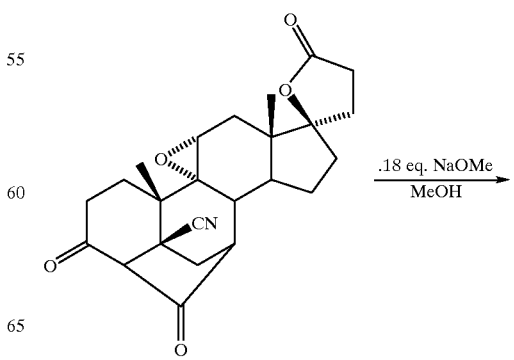

-continued

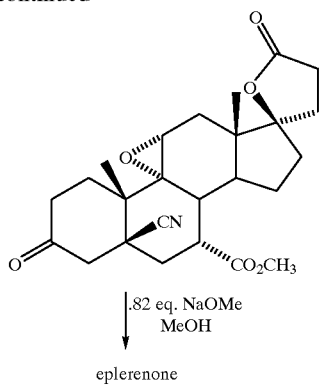

↓ .82 eq. NaOMe
MeOH eplerenone

EXAMPLE 60

To 100 mg of the diketone suspended in 1.5 mL of methanol was added 10 microliters (0.18 eq) of a 25% (w/w) solution of sodium methoxide in methanol. The solution was heated to reflux. After 30 min. no diketone remained and the 5-cyanoester was present. To the mixture was added 46 microliters of 25% (w/w) sodium methanol solution in methanol. The mixture was heated at reflux for 23 hours at which time the major product was eplerenone as judged by HPLC.

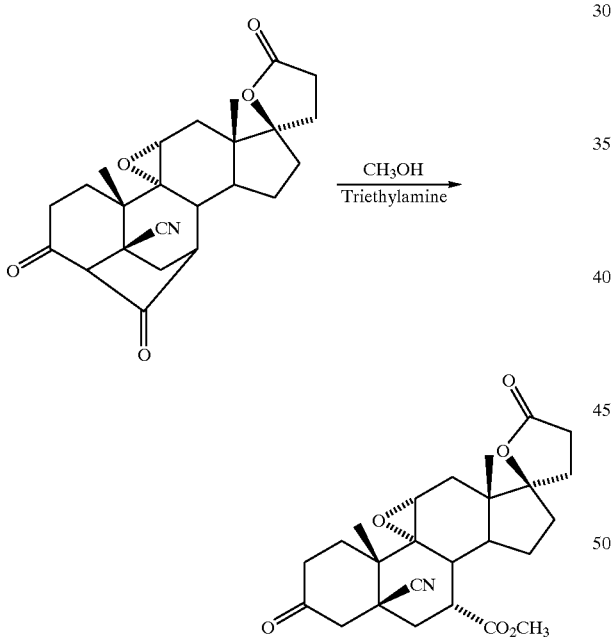

EXAMPLE 61

To 2 g of the diketone suspended in 30 ml of dry methanol was added 0.34 mL of triethylamine. The suspension was heated at reflux for 4.5 hours. The mixture was stirred at 25° C. for 16 hours. The resulting suspension was filtered to give 1.3 g of the 5-cyanoester as a white solid.

To 6.6 g of the diketone suspended in 80 mL of methanol was added 2.8 mL of triethylamine. The mixture was heated at reflux for 4 hours and was stirred at 25×for 88 hours during which time the product crystallized from solution. Filtration followed by a methanol wash gave 5.8 g of the cyanoester as a white powder. The material was recrystallized from chloroform/methanol to give 3.1 g of crystalline material which was homogeneous by HPLC.

In view of the above, it will be seen that the several objects of the invention are achieved and other advantageous results attained.

As various changes could be made in the above compositions and processes without departing from the scope of the invention, it is intended that all matter contained in the above description and shown in the accompanying drawings shall be interpreted as illustrative and not in a limiting sense.

What is claimed is:

1. A compound of Formula VII:

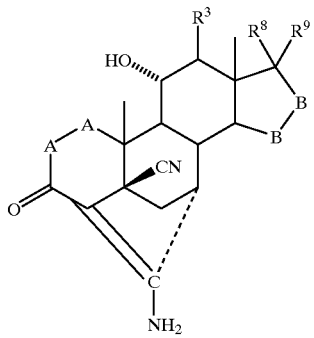

VII wherein

—A—A— represents the group —CHR$^4$—CHR$^5$— or —CR$^4$=CR$^5$—,

R$^3$, R$^4$ and R$^5$ are independently selected from the group consisting of hydrogen, halo, hydroxy, lower alkyl, lower alkoxy, hydroxyalkyl, alkoxyalkyl, hydroxycarbonyl, cyano, and aryloxy, —B—B— represents the group —CHR$^6$—CHR$^7$— or an alpha- or beta-oriented group:

III $$\begin{array}{c} R^6 \diagdown \quad \diagup R^7 \\ CH \text{———} CH \\ | \qquad \qquad | \\ \text{——}CH\text{—}CH_2\text{—}CH\text{——} \end{array}$$

where R$^6$ and R$^7$ are independently selected from the group consisting of hydrogen, halo, lower alkoxy, acyl, hydroxyalkyl, alkoxyalkyl, hydroxycarbonyl, alkyl, alkoxycarbonyl, acyloxyalkyl, cyano, and aryloxy, and R$^8$ and R$^9$ are independently selected from the group consisting of hydrogen, hydroxy, halo, lower alkoxy, acyl, hydroxyalkyl, alkoxyalkyl, hydroxycarbonylalkyl, alkoxycarbonylalkyl, acyloxyalkyl, cyano, and aryloxy, or R$^8$ and R$^9$ together comprise a carbocyclic or heterocyclic ring structure, or R$^8$ or R$^9$ together with R$^6$ or R$^7$ comprise a carbocyclic or heterocyclic ring structure fused to the pentacyclic D ring.

2. A compound of Formula VII as set forth in claim 1 wherein:

—A—A— represents the group —CH$_2$—CH$_2$— or —CH=CH—, and

—B—B— represents the group —CH$_2$—CH$_2$— or an alpha- or beta-oriented group:

IIIA

—CH—CH$_2$—CH—.

3. A compound of Formula VII as set forth in claim 2 wherein said compound corresponds to Formula VIIA:

VIIA wherein:
- —A—A— represents the group —CH$_2$—CH$_2$— or —CH═CH—,
- —B—B— represents the group —CH$_2$—CH$_2$— or an alpha- or beta-oriented group:

IIIA

—CH—CH$_2$—CH— wherein:
- X represents two hydrogen atoms or oxo,
- Y$^1$ and Y$^2$ together represent the oxygen bridge —O—, or
- Y$^1$ represents hydroxy, and
- Y$^2$ represents hydroxy, lower alkoxy or, if X represents H$_2$, also lower alkanoyloxy, or salts of compounds in which X represents oxo and Y$^2$ represents hydroxy.

4. A compound of Formula VII as set forth in claim 3 wherein said compound is 5. A compound correspound corresponding to Formula XV:

XV where
- —A—A— represents the group —CHR$^4$—CHR$^5$— or —CR$^4$═CR$^5$—,
- R$^3$, R$^4$ and R$^5$ are independently selected from the group consisting of hydrogen, halo, hydroxy, lower alkyl, lower alkoxy, hydroxyalkyl, alkoxyalkyl, hydroxycarbonyl, cyano, and aryloxy, and
- —B— represents the group —CHR$^6$—CHR$^7$— or an alpha- or beta-oriented group:

III where R$^6$ and R$^7$ are independently selected from the group consisting of hydrogen, halo, lower alkoxy, acyl, hydroxyalkyl, alkoxyalkyl, hydroxycarbonyl, alkyl, alkoxycarbonyl, acyloxyalkyl, cyano, and aryloxy.

6. A compound of Formula XV as set forth in claim 5 wherein said compound is 7. A compound of Formula XV as set forth in claim 5 wherein:
- —A—A— represents the group —CH$_2$—CH$_2$— or —CH═CH—, and
- —B— represents the group —CH$_2$—CH$_2$— or an alpha- or beta-oriented group:

$$-\text{CH}-\text{CH}_2-\text{CH}-\quad\text{IIIA.}$$

8. A compound corresponding to Formula XXII:

XXII wherein

—A—A— represents the group —CHR⁴—CHR⁵— or —CR⁴=CR⁵—,

R⁴ and R⁵ are independently selected from the group consisting of hydrogen, halo hydroxy, lower alkyl, lower alkoxy, hydroxyalkyl, alkoxyalkyl, hydroxycarbonyl, cyano, and aryloxy, and —B—B— represents the group —CHR⁶—CHR⁷— or an alpha- or beta-oriented group:

III $$\begin{array}{c} R^6 \diagdown \quad \diagup R^7 \\ \text{CH}\text{———}\text{CH} \\ -\text{CH}-\text{CH}_2-\text{CH}- \end{array}$$

where R⁶ and R⁷ are independently selected from the group consisting of hydrogen, halo, lower alkoxy, acyl, hydroxyalkyl, alkoxyalkyl, hydroxycarbonyl, alkyl, alkoxycarbonyl, acyloxyalkyl, cyano, and aryloxy.

9. A compound of Formula XXII as set forth in claim 8 wherein said compound is 10. A compound of Formula XXII as set forth in claim 8 wherein:

—A—A— represents the group —CH₂—CH₂— or —CH=CH—, and

—B—B— represents the group —CH₂—CH₂— or an alpha- or beta-oriented group:

$$-\text{CH}-\text{CH}_2-\text{CH}-\quad\text{IIIA.}$$

11. A compound corresponding Formula XXV:

XXV

—A—A— represents the group —CHR⁴—CHR⁵— or —CR⁴=CR⁵—,

R⁴ and R⁵ are independently selected from the group consisting of hydrogen, halo, hydroxy, lower alkyl, lower alkoxy, hydroxyalkyl, alkoxyalkyl, hydroxycarbonyl, cyano, and aryloxy, —B—B— represents the group —CHR⁶—CHR⁷— or an alpha- or beta-oriented group:

III $$\begin{array}{c} R^6 \diagdown \quad \diagup R^7 \\ \text{CH}\text{———}\text{CH} \\ -\text{CH}-\text{CH}_2-\text{CH}- \end{array}$$

where R⁶ and R⁷ are independently selected from the group consisting of hydrogen, halo, lower alkoxy, acyl, hydroxyalkyl, alkoxyalkyl, hydroxycarbonyl, alkyl, alkoxycarbonyl, acyloxyalkyl, cyano, and aryloxy, and Rˣ is selected from the group consisting of hydrogen or a hydroxy protecting group.

12. A compound of Formula XXV as set forth in claim 11 wherein said compound is wherein Et is ethyl.

13. A compound of Formula XXV as set forth in claim 11 wherein:
—A—A— represents the group —CH$_2$—CH$_2$— or —CH=CH—, and
—B—B— represents the group —CHR$_2$—CHR$_2$— or an alpha- or beta-oriented group:
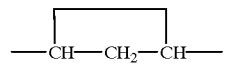
IIIA.
* * * * *